US011291176B2

(12) United States Patent
Sirizzotti et al.

(10) Patent No.: US 11,291,176 B2
(45) Date of Patent: Apr. 5, 2022

(54) SEEDLESS WATERMELON PLANTS COMPRISING MODIFICATIONS IN AN ABC TRANSPORTER GENE

(71) Applicant: NUNHEMS B.V., Nunhem (NL)

(72) Inventors: Alberto Sirizzotti, Sant Agata Bolognese (IT); Richard Bernard Berentsen, Paterna (ES); Wim Vriezen, Nunhem (NL); Lieke Mertens, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 17/252,176

(22) PCT Filed: Jun. 13, 2019

(86) PCT No.: PCT/EP2019/065524
§ 371 (c)(1),
(2) Date: Dec. 14, 2020

(87) PCT Pub. No.: WO2019/238832
PCT Pub. Date: Dec. 19, 2019

(65) Prior Publication Data
US 2021/0267154 A1    Sep. 2, 2021

(30) Foreign Application Priority Data
Jun. 15, 2018  (EP) .................................. 18178078

(51) Int. Cl.
C12Q 1/6895    (2018.01)
A01H 6/34      (2018.01)
C07K 14/415    (2006.01)
A01H 5/08      (2018.01)

(52) U.S. Cl.
CPC .............. *A01H 6/342* (2018.05); *A01H 5/08* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| WO | 2010049897 A2 | 5/2010 |
|----|---------------|--------|
| WO | 2012069539 A1 | 5/2012 |
| WO | 2017202715 A1 | 11/2017 |
| WO | 2018060444 A1 | 4/2018 |

OTHER PUBLICATIONS

Solanum tuberosum p-glycoprotein, UniProt accession No. M1BH80, published Apr. 3, 2013.*
The Potato Genome Sequencing Consortium, 2011, Genome Sequence and Analysis of the Tuber Crop Potato, Nature 475: 189-197.*
Sánchez-Fernández et al., 2001, The Arabidopsis thaliana ABC Protein Superfamily, a Complete Inventory, J. Biol. Chem. 276: 30231-30244.*
"PREDICTED: Cucumis sativus ABC transporter B family member 2 (LOC101219304), mRNA", Database Genbank [Online] NCBI, retrieved from Database accession No. XM_011654341, XP002785040, Mar. 23, 2015, pp. 1-2.
Acciarri, et al., "Genetically modified parthenocarpic eggplants: improved fruit productivity under both greenhouse and open field cultivation", BMC Biotechnology, vol. 2, Issue 1, Article No. 4, Apr. 4, 2002, pp. 1-7.
Allen, et al., "Transcript-specific, single-nucleotide polymorphism discovery and linkage analysis in hexaploid bread wheat (*Triticum aestivum* L.)", Plant Biotechnology Journal, vol. 9, Issue 9, Jun. 1, 2011, pp. 1086-1099.
Azumi, et al., "Homolog interaction during meiotic prophase I in Arabidopsis requires the SOLO DANCERS gene encoding a novel cyclin-like protein", The EMBO journal, vol. 21, Issue 12, Jun. 17, 2002, pp. 3081-3095.
De Muyt, et al., "A High Throughput Genetic Screen Identifies New Early Meiotic Recombination Functions in *Arabidopsis thaliana*", PLoS Genetics, vol. 5, Issue 9 Sep. 18, 2009, pp. 1-14.
European Search Report for EP Patent Application No. 18178078.4, dated Jan. 14, 2019, pp. 1-4.
Guner, et al., "The Genes of Watermelon", HortScience, vol. 39, Issue 6, Jan. 1, 2004, pp. 1175-1182.
Hwang, et al., "Plant ABC Transporters Enable Many Unique Aspects of a Terrestrial Plant's Lifestyle", Molecular Plant, vol. 9, Issue 3, Mar. 7, 2016, pp. 338-355.
International Search Report for PCT Patent Application No. PCT/EP2019/065524, dated Oct. 21, 2019, pp. 1-6.
Jasinski, et al., "The ATP-Binding Cassette Transporters: Structure, Function, and Gene Family Comparison between Rice and *Arabidopsis*", Plant Physiology, vol. 131, Issue 3, Mar. 2003, pp. 1169-1177.
McCallum, et al., "Targeting Induced Local Lesions IN Genomes (TILLING) for Plant Functional Genomics", Plant Physiology, vol. 123, Issue 2, Jun. 2000, pp. 439-442.
Meru, et al., "A non-destructive genotyping system from a single seed for marker-assisted selection in watermelon", Genetics and Molecular Research, vol. 12, Issue 1, Mar. 11, 2013, pp. 702-709.
Mette, et al., "Transcriptional silencing and promoter methylation triggered by double-stranded RNA", The EMBO Journal, vol. 19, Issue 19, Oct. 2, 2000, pp. 5194-5201.
Michael J. Thomson, "High-Throughput SNP Genotyping to Accelerate Crop Improvement", Plant Breeding and Biotechnology, vol. 2, Issue 3, Sep. 30, 2014, pp. 195-212.
N. A. Kazi, "Polyploidy in vegetables", Journal of Global Biosciences, vol. 4, Issue 3, 2015, pp. 1774-1779.
Pradillo, et al., "On the role of AtDMCI, AtRAD51 and its paralogs during *Arabidopsis meiosis*", Frontiers in Plant Science, vol. 5, Article No. 23, Feb. 17, 2014, pp. 1-13.
Ren, et al., "SlTIR1 is involved in crosstalk of phytohormones, regulates auxin-induced root growth and stimulates stenospermocarpic fruit formation in tomato", Plant Science, vol. 253, Dec. 2016, pp. 13-20.

(Continued)

*Primary Examiner* — Bratislav Stankovic
(74) *Attorney, Agent, or Firm* — Arent Fox LLP

(57) ABSTRACT

The present invention is directed to seedless fruit producing plants. The present invention also comprises methods for production of said plants and the use of nucleic acids encoding ABCB transporter proteins for the production of seedless fruits.

11 Claims, 5 Drawing Sheets

Specification includes a Sequence Listing.

(56) References Cited

OTHER PUBLICATIONS

Rodríguez-Leal, et al., "Engineering Quantitative Trait Variation for Crop Improvement by Genome Editing", Cell, vol. 171, Issue 2, Oct. 5, 2017, pp. 470-480.

Rotino, et al., "Open field trial of genetically modified parthenocarpic tomato: seedlessness and fruit quality", BMC Biotechnology, vol. 5, Issue 1, Article No. 32, Dec. 21, 2005, pp. 1-8.

Ruan, et al., "Molecular regulation of seed and fruit set", Trends in Plant Science, vol. 17, Issue 11, Nov. 2012, pp. 656-665.

Tang, et al., "Gene cloning and expression analyses of WBC genes in the developing grapevine seeds", Journal of Integrative Agriculture, vol. 17, Issue 6, Jun. 2018, pp. 1348-1359.

Thorneycroft, et al., "Using gene knockouts to investigate plant metabolism", Journal of Experimental Botany, vol. 52, Issue 361, Aug. 1, 2001, pp. 1593-1601.

Xu, et al., "The B subfamily of plant ATP binding cassette transporters and their roles in auxin transport", Biologia Plantarum, vol. 58, Issue 3, May 21, 2014, pp. 401-410.

Yin, et al., "The Defl-l9-iaaM-containing construct efficiently induces parthenocarpy in cucumber", Cellular & Molecular Biology Letters, vol. 11, Issue 2, Apr. 22, 2006, pp. 279-290.

Zhang, et al., "Characteristics of a novel male-female sterile watermelon (*Citrullus lanatus*) mutant", Scientia Horticulturae, vol. 140, Jun. 1, 2012, pp. 107-114.

Zhang, et al., "Tissue culture-induced heritable genomic variation in rice, and their phenotypic implications", PloS one, vol. 9, Issue 5, May 7, 2014, pp. 1-10.

\* cited by examiner

Figure 1

```
SEQ ID: 1 (WMW)    MRNHGNTVSY-DHEEENEDEVSMKKRKNDEEEEEDDGK--KKKKKKKEQQNKVAFYKLFA
SEQ ID: 4 (CUC)    MRNHGSSISYHEHREEENEEHDKKKRKNDEEEEEEDGKEMKKKKKKEEKNNKVAFYKLFA
SEQ ID: 5 (MEM)    ------------------------MKTKK--------------KKKKKQEKNNNKVAFYKLFA

SEQ ID: 1 (WMW)    FADFYDYFLMSFGSIGACIHGASVPVFFIFFGKLINIIGMAYLFPEDAAPKVAKYSLDFL    TMD1
SEQ ID: 4 (CUC)    FADFYDYVLMSIGSIGACIHGASVPVFFIFFGKLINIIGMAYLFPEAAAPKVAKYSLDFL
SEQ ID: 5 (MEM)    FADFYDYILMSIGSIGACIHGASVPVFFIFFGKLINIIGMAYLFPEAAAPKVAKYSLDFL

SEQ ID: 1 (WMW)    YLSVAILFSSWAEVACWMHSGERQAAKMRMAYLKSMLNQDISLFDTEASTGEVIAAITSD
SEQ ID: 4 (CUC)    YLSVAILFSSWAEVACWMHSGERQAAKMRMAYLRSMLNQDISLFDTEASTGEVIAAITSD
SEQ ID: 5 (MEM)    YLSVAILFSSWAEVACWMHSGERQAAKMRMAYLKSMLNQDISLFDTEASTGEVIAAITSD

SEQ ID: 1 (WMW)    IVIVQDAISEKVGNFLHYISRFISRFIIGFVRVWQISLVTLSIVPLIALAGGLYAFVTIG
SEQ ID: 4 (CUC)    IVVVQDAISEKVGNFLHYISRFISGFIIGFVRVWQISLVTLSIVPLIALAGGLYAFVTIG
SEQ ID: 5 (MEM)    IVVVQDAISEKVGNFLHYISRFISGFIIGFVRVWQISLVTLSIVPLIALAGGLYAFVTIG

SEQ ID: 1 (WMW)    LIAKVRKSYVKAGEIAEEILGNVRTVQAFAGEERAVNLYKGALKNTYKYGRKAGLAKGLG
SEQ ID: 4 (CUC)    LIAKVRKSYVKAGEIAEEILGNVRTVQAFAGEERAVNLYKGALKNTYKYGRKAGLAKGLG
SEQ ID: 5 (MEM)    LIAKVRKSYVKAGEIAEEILGNVRTVQAFAGEERAVNLYKGALKNTYKYGRKAGLAKGLG

SEQ ID: 1 (WMW)    LGSMHCVLFLSWALLVWFTSIVVHKGIANGGDSFTTMLNVVISGLSLGQAAPDISAFVRA
SEQ ID: 4 (CUC)    LGSMHCVLFLSWALLVWFTSIVVHKGIANGGDSFTTMLNVVISGLSLGQAAPDISAFVRA
SEQ ID: 5 (MEM)    LGSMHCVLFLSWALLVWFTSIVVHKGIANGGDSFTTMLNVVISGLSLGQAAPDISAFVRA

SEQ ID: 1 (WMW)    KAAAYPIFQMIERNTVSKSSSKTGRKLNKLDGHIQFKDVNFSYPSRLDVIIFNKLSLDIP    NBD1
SEQ ID: 4 (CUC)    KAAAYPIFQMIERNTVSKSSSKTGWKLNKLDGFIQFKDVNFSYPSRQDVIIFNKLSLDIP
SEQ ID: 5 (MEM)    KAAAYPIFQMIERNTVSKSSSKTGRKLNKLDGYIQFKDVNFSYPSRPDVIIFNKLSLDIP

SEQ ID: 1 (WMW)    AGKIVALVGGSGSGKSTVISLIERFYEPLSGEILLDGNNIKELDLKWLRQQIGLVNQEPA
SEQ ID: 4 (CUC)    AGKIVALVGGSGSGKSTVISLIERFYEPLSGEILLDGHNIKDLDLKWFRQQIGLVNQEPA
SEQ ID: 5 (MEM)    AGKIVALVGGSGSGKSTVISLIERFYEPLSGEILLDGHNIKELDLKWFRQQIGLVNQEPA

SEQ ID: 1 (WMW)    LFATSIRENILYGKDDATLEDITPAAKLSEALSFINNLPERFETQVGERGVQLSGGQKQR
SEQ ID: 4 (CUC)    LFATSIRENILYGKDDATLEDITRAAKLSEALSFINNLPERFETQVGERGVQLSGGQKQR
SEQ ID: 5 (MEM)    LFATSIRENILYGKDDATLEDITRAAKLSEALSFINNLPERFETQVGERGVQLSGGQKQR

SEQ ID: 1 (WMW)    IAISRAIVKNPSILLLDEATSALDAESEKSVQEALDRVMVGRTTVVVAHRLSTIRNADVI
SEQ ID: 4 (CUC)    IAISRAIVKNPSILLLDEATSALDAESEKSVQEALDRVMVGRTTVVVAHRLSTIRNADVI
SEQ ID: 5 (MEM)    IAISRAIVKNPSVLLLDEATSALDAESEKSVQEALDRVMVGRTTVVVAHRLSTIRNADVI

SEQ ID: 1 (WMW)    AVVQEGKIVETGSHDELISKPDSVYASLVQFQETSSLQHHPSIGQLGRPPSIKYSRELSR
SEQ ID: 4 (CUC)    AVVQEGKIVETGSHDELISRPDSVYASLVQFQETASLQRHPSIGQLGRPPSIKYSRELSR
SEQ ID: 5 (MEM)    AVVQEGKIVETGSHDELISRPDSVYASLVQFQETASLQRHPSFGQLGRPPSIKYSRELSR

SEQ ID: 1 (WMW)    TTTSFGASFRSEKESLGRIGVDGMEMEKPKHVSARRLYSMVGPDWMYGIVGVIGAFVTGS    TMD2
SEQ ID: 4 (CUC)    TTTSFGASFRSEKESLGRIGVDGMEMEKPRHVSAKRLYSMVGPDWMYGIVGVIGAFVTGS
SEQ ID: 5 (MEM)    TTTSFGASFRSEKESLGRIGVDGMEMEKPRHVSAKRLYSMVGPDWMYGIVGVIGAFVTGS

SEQ ID: 1 (WMW)    QMPLFALGVSQALVAFYMDWNTTQHEIKKISLLFCGGAVLTVIFHAVEHLCFGIMGERLT
SEQ ID: 4 (CUC)    QMPLFALGVSQALVAFYMDWDTTQHEIKKISLLFCGGAVLTVIFHAVEHLCFGIMGERLT
SEQ ID: 5 (MEM)    QMPLFALGVSQALVAFYMDWDTTQHEIKKISLLFCGGAVLTVIFHAVEHLCFGIMGERLT

SEQ ID: 1 (WMW)    LRVREKMFHAILRNEIGWFDDMNNTSSMLSSRLETDATLLRTIVVDRSTILLQNLALVVA
SEQ ID: 4 (CUC)    LRVREMMFHAILRNEIGWFDDMNNTSAMLSSRLETDATLLRTIVVDRSTILLQNLALVVA
SEQ ID: 5 (MEM)    LRVREMMFHAILRNEIGWFDDMNNTSAMLSSRLETDATLLRTIVVDRSTILLQNLALVVA
```

Figure 1 (Continued)

```
SEQ ID: 1 (WMW)    SFIIAFILNWRITLVVLATYPLIISGHISEKLFMQGYGGNLSKAYLKANTLAGEAVGNIR
SEQ ID: 4 (CUC)    SFIIAFILNWRITLVVLATYPLIISGHISEKLFMQGYGGNLSKAYLKANTLAGEAVGNIR
SEQ ID: 5 (MEM)    SFIIAFILNWRITLVVLATYPLIISGHISEKLFMQGYGGNLSKAYLKANTLAGEAVGNIR

SEQ ID: 1 (WMW)    TVAAFCSEQKVLDLYAKELVEPSRRSLKRGQIAGIFYGVSQFFIFSSYGLALWYGSVLMG
SEQ ID: 4 (CUC)    TVAAFCSEEKVLDLYAKELVEPSRRSLKRGQIAGIFYGVSQFFIFSSYGLALWYGSVLMG
SEQ ID: 5 (MEM)    TVAAFCSEEKVLDLYAKELVEPSRRSLKRGQIAGIFYGVSQFFIFSSYGLALWYGSVLMG

SEQ ID: 1 (WMW)    QGLASFKSVMKSFMVLIVTALAMGETLALAPDLLKGNQMVASVFEVMDRQTEVSGDVGEE
SEQ ID: 4 (CUC)    HGLASFKSVMKSFMVLIVTALAMGETLALAPDLLKGNQMVASVFEVMDRQTEVSGDVGEE
SEQ ID: 5 (MEM)    QGLASFKSVMKSFMVLIVTALAMGETLALAPDLLKGNQMVASVFEVMDRQTEVPGDVGEE

SEQ ID: 1 (WMW)    LNVVEGTIELRSVEFSYPSRPDVLIFKDFNLKVRAGKSIALVGQSGSGKSSVLALILRFY    NBD2
SEQ ID: 4 (CUC)    LNVVEGTIELRNVEFVYPSRPDVMIFKDFNLKVRAGKSIALVGQSGSGKSSVLALILRFY
SEQ ID: 5 (MEM)    LNVVEGTIELRNVEFVYPSRPDVMIFKDFNLKVRAGKSIALVGQSGSGKSSVLALILRFY

SEQ ID: 1 (WMW)    DPIAGKVMIDGKDIKKLKLKSLRKHIGLVQQEPALFATSIYENILYGKEGASEAEVFEAA
SEQ ID: 4 (CUC)    DPIAGKVMIDGKDIKKLKLKSLRKHIGLVQQEPALFATSIYENILYGKEGASEAEVFEAA
SEQ ID: 5 (MEM)    DPIAGKVMIDGKDIKKLKLKSLRKHIGLVQQEPALFATTIYENILYGKEGASEAEVFEAA

SEQ ID: 1 (WMW)    KLANAHNFISALPEGYSTKVGERGIQLSGGQRQRIAIARAVLKNPEILLLDEATSALDVE
SEQ ID: 4 (CUC)    KLANAHNFISALPEGYSTKVGERGIQLSGGQRQRIAIARAVLKNPEILLLDEATSALDVE
SEQ ID: 5 (MEM)    KLANAHNFISALPEGYSTKVGERGIQLSGGQRQRIAIARAVLKNPEILLLDEATSALDVE

SEQ ID: 1 (WMW)    SERVVQQALDRLMMNRTTVVVAHRLSTIKNCDQISVIQDGKIVEQGTHSSLSDNKNGAYY
SEQ ID: 4 (CUC)    SERVVQQALDRLMMNRTTVVVAHRLSTIKNCDQISVIQDGKIVEQGTHSSLSENKNGAYY
SEQ ID: 5 (MEM)    SERVVQQALDRLMMNRTTVVVAHRLSTIKNCDQISVIQDGKIVEQGTHSSLSENKNGAYY

SEQ ID: 1 (WMW)    KLINIQQQQRQ
SEQ ID: 4 (CUC)    KLINIQQQQRQ
SEQ ID: 5 (MEM)    KLINIQQQQRQ
```

Figure 2
A
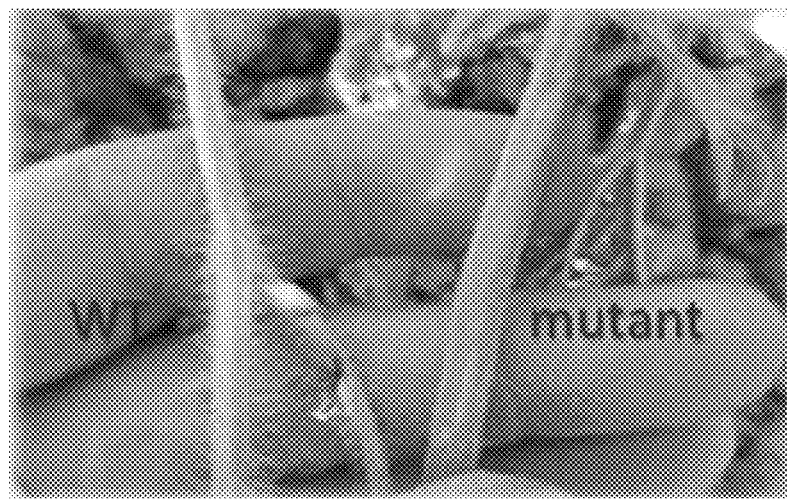
B

Figure 3

```
SEQ ID: 1  (WMW)     -MRNHGNTVSYDHEEENEDEVSMKKRKNDEEEEEDDGKKKKKKKKEQQNKVAFYKLFAFA
SEQ ID: 9  (tomato) MSQQQSHALSVD-----SSKISKMNQKNNEEEEE--------RKKKTHKKVSLLKLFSFA
SEQ ID:10  (Pepper) MSHQQSHALSVD-----SSGISKMKQKNIGDEE-----------RKKPKKVSLLKLFSFA
SEQ ID:11  (Pepper) MSHQQSHALSVD-----SSGISKMKQKNTGDEE-----------RKKPKKVSLLKLFSFA SEQ ID: 1  (WMW)    DFYDYFLMSFGSIGACLHGASVPVFFIFFGKLINIIGMAYLFPEDAAPKVAKYSLDFLYL    TMD1
SEQ ID: 9  (tomato) DSYDYLLMFLGSIGACLHGASVPVFFIFFGKMINIAGLAYLFPAQTSHKIAKYSLDFVYL
SEQ ID:10  (Pepper) DSYDYLLMFLGSIGACLHGASVPVFFIFFGKLINIAGLAYLFPALASHKVAKYSLDFVYL
SEQ ID:11  (Pepper) DSYDYLLMFLGSIGACLHGASVPVFFIFFGKLINIAGLAYLFPALASHKVAKYSLDFVYL SEQ ID: 1  (WMW)    SVVILFSSWAEVACWMHSGERQAAKMRMAYLKSMLNQDISLFDTEASTGEVIAAITSDIV
SEQ ID: 9  (tomato) SVVILFASWIEVACWMHSGERQAAKIRMAYLKSMLNQDISLFDTEASTGEVIAAITSDII
SEQ ID:10  (Pepper) SVVILFASWIEVACWMHSGERQAAKIRMAYLKSMLNQDISLFDTEASTGEVISAITSDII
SEQ ID:11  (Pepper) SVVILFASWIEVACWMHSGERQAAKIRMAYLKSMLNQDISLFDTEASTGEVISAITSDII SEQ ID: 1  (WMW)    IVQDAISEKVGNFLHYISRFISRFTIGFVRMWQISLVTLSIVPLIALAGGIYAFVTIGLI
SEQ ID: 9  (tomato) IVQDAISEKAGNFLHYISRFLAGFTIGFIRVWQISLVTLSIVPLIALAGGIYAYVTIGLI
SEQ ID:10  (Pepper) VVQDAISEKAGNFMHYISRFLAGFTIGFIRVWQISLVTLSIVPLIALAGGIYAFVTIGLI
SEQ ID:11  (Pepper) VVQDAISEKAGNFMHYISRFLAGFTIGFIRVWQISLVTLSIVPLIALAGGIYAFVTIGLI SEQ ID: 1  (WMW)    ARVRKSYVKAGEIAEEILGNVRTVQAFAGEERAVNLYKGALKNTYKYGRKAGLAKGLGLG
SEQ ID: 9  (tomato) ARVRKSYIKAGEIAEEVVANIRTVQAFTGEENAVKSYKGALLNTYKYGRKAGFAKGLGLG
SEQ ID:10  (Pepper) ARVRKSYINAGEVAEEVIANIRTVQAFAGEEKAVKSYKGVLLNTYQYGKKAGLAKGLGLG
SEQ ID:11  (Pepper) ARVRKSYINAGEVAEEVIANIRTVQAFAGEEKAVKAYKGALLNTYQYGKKAGLAKGLGLG SEQ ID: 1  (WMW)    SMHCVLFLSWALLVWFTSIVVHKGIANGGDSFTTMLNVVISGLSLGQAAPDISAFVRAKA
SEQ ID: 9  (tomato) TLHCILFLSWSLLVWFTSIVVHKNIANGGDSFTTMLNVVIAGLSLGQAAPDITAFLRAKS
SEQ ID:10  (Pepper) TLHCVLFLSWSLLVWFTSIVVHKNIANGGESFTTMLNVVIAGLSLGQAAPDITAFLRAKS
SEQ ID:11  (Pepper) TLHCVLFLSWSLLVWFTSIVVHKNIANGGESFTTMLNVVIAGLSLGQAAPDITAFLRAKS SEQ ID: 1  (WMW)    AAYPIFQMIERNTVSKSSSKTGRKLNKLDGHIQFKDVNFSYPSKLDVIIFNKLSLDIPAG    NBD1
SEQ ID: 9  (tomato) AAYPIFEMIERDTISKTSSKSGQKLSKVDGHIQFKDVCFSYPSRPDVVIFDKLSLDIPSG
SEQ ID:10  (Pepper) AAYPIFEMIERDTISKISSKSGHQLSEVDGHIQFKDVCFSYPSRPDVVIFDKFSLDIPSG
SEQ ID:11  (Pepper) AAYPIFEMIERDTISKISSKSGHQLSEVDGHIQFKDVCFSYPSRPDVVIFDKFSLDIPSG SEQ ID: 1  (WMW)    KIVALVGGSGSGKSTVISLIERFYEPLSGEILLDGNIIKELDLKWLRQQIGLVNQEPALF
SEQ ID: 9  (tomato) KIVALVGGSGSGKSTVISLIERFYEPLSGQILLDGFDIRHLDLKWLRQQIGLVNQEPALF
SEQ ID:10  (Pepper) KIVALVGGSGSGKSTVISLIERFYEPLSGHILLDGSDIRHLDLKWLRQQIGLVNQEPALF
SEQ ID:11  (Pepper) KIVALVGGSGSGKSTVISLIERFYEPLSGHILLDGSDIRHLDLKWLRQQIGLVNQEPALF SEQ ID: 1  (WMW)    ATSIRENILYGKDDATLEDIRAAKLSEALGFINNLPDRFETQVGERGVQLSGGQKQRIA
SEQ ID: 9  (tomato) ATTIRENILYGKSDASLEDIARAAKLSEAMTFINNLPDRFETQVGERGVQLSGGQKQRIA
SEQ ID:10  (Pepper) ATTIRENILYGKSDASLEDIARAAKLSEAMTFINNLPDRLETQVGERGVQLSGGQKQRIA
SEQ ID:11  (Pepper) ATTIRENILYGKSDASLEDIARAAKLSEAMTFINNLPDRLETQVGERGVQLSGGQKQRIA SEQ ID: 1  (WMW)    ISRAIVKNPSILLLDEATSALDAESEKSVQEALDRVMGRTTVVAHRLSTIRNADYIAV
SEQ ID: 9  (tomato) ISRAIVKNPSILLLDEATSALDAESEKSVQDALDRVMVGRTTVIVAHRLSTIRNADIIAV
SEQ ID:10  (Pepper) ISRAIVKNPSILLLDEATSALDAESEKSVQDALDRVMVGRTTVIVAHRLSTIRNVDIIAV
SEQ ID:11  (Pepper) ISRAIVKNPSILLLDEATSALDAESEKSVQDALDRVMVGRTTVIVAHRLSTIRNVDIIAV SEQ ID: 1  (WMW)    VQEGKIVETGSHDELISKPDSYYASLVQRQETSSLQHHP-SIGQLGRFPPSIKYSRELSRT
SEQ ID: 9  (tomato) VNNGKIVETGSHEELISKPNSAYASLVQLQQAASSHLPSQEPTMGRPHSIRYSRELSRT
SEQ ID:10  (Pepper) VNNGKIVETGSHEELISKPNGAYASLVQLQQAASSHL---QEPTMGRPLSIRYSRELSRT
SEQ ID:11  (Pepper) VNNGKIVETRSHEELISKPNGAYASLVQLQQAASSHL---QEPTMGRPLSIRYSRELSRT
```

Figure 3 (continued)

```
SEQ ID: 1  (WMW)      TTSF-GASFRSEKESLGRIGVDGMEMEKPKHVSARRLYSMVGPDWMYGIVGVIGAFVTGS
SEQ ID: 9  (tomato)   TTRSRGASFRSEK-SVSGIGAGDVEDVKSPNVSAGRLYSMIRPEWHYGVIGTICAFIAGA    TMD2
SEQ ID:10  (Pepper)   RTQSHGASFRSEK-SVSGIGDAGVEDVKEPNISLRRLYSMIRPEWHYGVIGTISAFIAGS
SEQ ID:11  (Pepper)   RTQSHGASFRSEK-SVSGIGDAGVEDVKEPNISLRRLYSMIRPEWHYGVIGTISAFIAGS SEQ ID: 1  (WMW)      QMPLFALGVSQALVAFYMDWNTTQHEIKKISLLFCGGAVLTVIFHAVEHLCFGIMGERLT
SEQ ID: 9  (tomato)   QMPLFALGVSQALVSYYMDWDTTRHEVKKICFLFCVGAVLTVVVHAIAHTCFGIIGERLT
SEQ ID:10  (Pepper)   QMPLFALGVSQALVSYYMDWDTTRHEVKKISILFCIGAVLSVIVYAIAHTCFGIIGARLT
SEQ ID:11  (Pepper    QMPLFALGVSQALVSYYMDWDTTRHEVKKISILFCIGAVLSVIVYAIAHTCFGIIGARLT SEQ ID: 1  (WMW)      LRVREKMFHAILRNEIGWFDDMNNTSSMLSSRLETDATLLRTIVVDRSTILLQNLALVVA
SEQ ID: 9  (tomato)   LRVREMMFSAMLRNEIGWFDEVNNSSSTLASRLESDATLLRTVVVDRSTILLQNVGLVAT
SEQ ID:10  (Pepper)   LRVREMMFSAMLRNEIGWFDEMNNSSSSLASRLESDATLLRTVVVDRSTILLQNVGLVFT
SEQ ID:11  (Pepper)   LRVREMMFSAMLRNEIGWFDEMNNSSSSLASRLESDATLLRTVVVDRSTILLQNVGLVFT SEQ ID: 1  (WMW)      SFIIAFILNWRITLVVLATYPLIISGHISEKLFMQGYGGNLSKAYLKANTIAGEAVGNIR
SEQ ID: 9  (tomato)   SFIIAFILNWRLTLVVMAMYPLIVSGHISEKLFMSGFGGDLSKAYLRANMFAGEAVSNIR
SEQ ID:10  (Pepper)   SFVIAFMLNWRLTLIVMAMYPLIISGHISEKLFMAGFGGDLSKAYLRANMFAGEAVSNIR
SEQ ID:11  (Pepper)   SFVIAFMLNWRLTLIVMAMYPLIISGHISEKLFMAGFGGDLSKAYLRANMFAGEAVSNIR SEQ ID: 1  (WMW)      TVAAFCSEQKVLDLYAKELVEPSRRSLKRGQIAGIFYGVSQFFIFSSYGLALWYGSVLMG
SEQ ID: 9  (tomato)   TVAAFCAEEKVTDLYARELVEPAKHSFRRGQTAGILYGVSQFFIFSSYALALWYGSVLMG
SEQ ID:10  (Pepper)   TVAAFCAEEKVTDLYARELVEPAKRSFSRGQIAGIFYGVSQFFIFSSYGLALWYGSVLMG
SEQ ID:11  (Pepper)   TVAAFCAEEKVTDLYARELVEPAKRSFSRGQIAGIFYGVSQFFIFSSYGLALWYGSVLMG SEQ ID: 1  (WMW)      QGLASFKSVMKSFMVLIVTALAMGETLALAPDLLKGNQMVASVFEVMDRQTEVSGDVGEE
SEQ ID: 9  (tomato)   KELTSFKAVMKSFMVLIVTALAMGETLAMAPDLIKGNQMVASVFEVLDRKTEIVTDSGEE
SEQ ID:10  (Pepper)   KELTSFKAVMKSFMVLIVTALAMGETLAMAPDLIKGNQMVASVFEVLDRRTEILADTGEE
SEQ ID:11  (Pepper)   KELTSFKAVMKSFMVLIVTALAMGETLAMAPDLIKGNQMVASVFEVLDRRTEILADTGEE SEQ ID: 1  (WMW)      LNVVEGTIELRSVEFSYPSRPDVLIFKDFNLKVRAGKSIALVGQSGSGKSSVLALILRFY
SEQ ID: 9  (tomato)   LTVVEGTIEFKDVEFCYPARPDVHIFRDFNMRVHAGKSMAIVGQSGSGKSSVLALILRFY    NBD2
SEQ ID:10  (Pepper)   VTEVEGTIEFKDVEFCYPARPDVHIFKDFNMRVHAGESMAIVGQSGSGKSSVLALILRFY
SEQ ID:11  (Pepper)   VTEVEGTIEFKDVEFCYPARPDVHIFKDFNMRVHAGESMAIVGQSGSGKSSVLALILRFY SEQ ID: 1  (WMW)      DPIAGKVMIDGKDIKKLKLKSLRKHIGLVQQEPALFATSIYENILYGKEGASEAEVFEAA
SEQ ID: 9  (tomato)   DPISGKVIIDGKDIRKLKLNSLRKHIGLVQQEPALFATTIYENILYGKEGASEAEVIQAA
SEQ ID:10  (Pepper)   DPISGKVIIDGKDIRKLKLKSLRKHIGLVQQEPALFATSIYENILYGKEGASEAEVIDAA
SEQ ID:11  (Pepper)   DPISGKVIIDGKDIRKLKLKSLRKHIGLVQQEPALFATSIYENILYGKEGASEAEVIDAA SEQ ID: 1  (WMW)      KLANAHNFISALPEGYSTKVGERGIQLSGGQRQRIAIARAVLKNPEILLDEATSALDVE
SEQ ID: 9  (tomato)   KLANAHSFISALPDGYSTQVGERGVQLSGGQKQRVAIARAVLKNPEILLLDEATSALDVE
SEQ ID:10  (Pepper)   KLANAHNFISALPDGYSTQVGERGVQLSGGQKQRVAIARAVLKNPEILLLDEATSALDVE
SEQ ID:11  (Pepper)   KLANAHNFISALPDGYSTQVGERGVQLSGGQKQRVAIARAVLKNPEILLLDEATSALDVE SEQ ID: 1  (WMW)      SERVVQQALDRLMMNRTTVVVAHRLSTIIKNCDQISVIQDGKIVFQGTHSSLSDNKNGAYY
SEQ ID: 9  (tomato)   SERIVQQALDRLMRNRTTVIVAHRLSTIKDADQISVLQDGKIVDQGTHSALIENRDGAYF
SEQ ID:10  (Pepper)   SERIVQQALDRLMQNRTTVIVAHRLSTIRNADQISVLQDGKIMEQGTHSALVENNDGAYH
SEQ ID:11  (Pepper)   SERIVQQALDRLMQNRTTVIVAHRLSTIRNADQISVLQDGKIMEQGTHSALVENNDGAYH SEQ ID: 1  (WMW)      KLINIQQQQQRQ
SEQ ID: 9  (tomato)   KLIHLQQQQQ-
SEQ ID:10  (Pepper)   KLINLQQQQQ-
SEQ ID:11  (Pepper)   KLINLQQQQQ-
```

SEEDLESS WATERMELON PLANTS COMPRISING MODIFICATIONS IN AN ABC TRANSPORTER GENE

CROSS-REFERENCE TO RELATED APPLICATIONS

This application is a National Stage Entry of PCT/EP2019/065524, filed Jun. 13, 2019, which claims priority to EP application No. 18178078.4, filed Jun. 15, 2018, the disclosures of each of which are hereby incorporated by reference in their entireties.

The present invention is directed to seedless fruit producing plants. The present invention also comprises methods for production of said plants and the use of nucleic acids encoding ABC transporter proteins for the production of seedless fruits.

Most commercial seedless fruits have been developed from plants whose fruits normally contain numerous relatively large hard seeds distributed throughout the flesh of the fruit. Seedless fruits are e.g. known for watermelon, tomato, cucumber, eggplant, grapes, banana, citrus fruits, such as orange, lemon and lime. As consumption of seedless fruits is generally easier and more convenient, they are considered valuable.

Fruit development normally begins when one or more egg cells in the ovular compartment of the flower are fertilized by sperm nuclei from pollen.

Seedless fruits can result from two different phenomena. In some cases fruit develops without fertilization of the ovule by pollen, a phenomenon known as parthenocarpy. In other cases seedless fruits occur after pollination when seed (embryo and/or endosperm) growth is inhibited or the seed dies early, while the remainder of the fruit continues to grow (stenospermocarpy). In contrast to parthenocarpy, stenospermocarpy requires pollination for initiation of fruit growth.

Seedless orange fruits are an example for parthenocarpy. Some orange varieties (e.g. Navel) do not produce viable pollen. They however can be cross-pollinated with pollen from other varieties. In case only the male sterile variety is grown in an orchard, there will be no pollination and parthenocarp seedless fruits will be produced. Propagation of the respective orange trees is commonly done by cuttings followed by grafting to another rootstock.

Seedless bananas are triploid. Although pollination in some cases can be normal and, the vast majority of fruits is seedless. This is explained by the uneven sets of chromosomes (3×) leading to improper division of chromosomes during meiosis and as a consequence to the production of non-viable pollen. Without fertilization, triploid bananas are also able to set and develop seedless fruits. Even when pollination takes place, at most one in three hundred fruits comprises a few seeds. This may be due to the triploid pollen being non-viable, for the reasons explained. Therefore, banana plants can in general be seen to be parthenocarpic. Banana plants are commonly propagated asexually from side shoots or suckers at the base of the main stalk, which can be removed and replanted to continue the cultivar. Growers also propagate bananas by means of tissue culture, in particular for producing disease free material.

Seedless cucumber, seedless squash and seedless eggplant are examples for crops which can produce seedless fruits without pollination (parthenocarpy), e.g. under conditions where pollination is impaired (e.g. low temperatures). Nevertheless, commercial quality fruit can be produced under these conditions. All these crops however can produce seed bearing fruits upon pollination. Therefore, these crops are facultative parthenocarpic. Propagation of the crops can be done by self- or cross pollination, in vitro propagation, and grafting.

From tomato mutants it is also known that they can produce seedless fruits under conditions where normal pollination/fertilization is impaired (e.g. under circumstances of low temperature). Thus, these mutants are also facultative parthenocarpic. Mutants known for showing this phenotype are pat, pat-2 and the pat-3/pat-4 system. The genes underlying these mutations are not known and the pat-3/pat-4 system seems to depend on multiple loci.

Parthenocarpy has also been introduced into several plant species by means of genetic modification. Expression of a bacterial tryptophan monooxygenase (iaaM) conferring auxin synthesis under control of the ovule and placenta specific DefH9 promoter did induce parthenocarpy in cucumbers (Yin et al., 2006, Clular & molecular Biotech. Letters 11, 279-290), eggplant (Acciarri et al., 2002, BMC Biotech. 2(4)), tomato (Rotino et al., 2005, BMC Biotech. 5(32)) and tobacco.

These transgenic plants demonstrate the importance of plant hormones in seed and fruit development. That seed and fruit development are besides other factors strongly under control of several plant hormones is well known in the art. Parthenocarpy, including the logical consequence of fruit's seedlessness, can also be induced e.g. by exogenous application of plant hormones, in particular auxin or gibberellin (Ruan et al., Trends in Plant Sci. 17(11), 1360-1385).

Seedless watermelons produced by breeders are examples for stenospermocarp crops. Normal watermelon plants are diploid (2n). Seedless fruit producing watermelons are hybrids produced by crossing a male diploid (2n) watermelon plant with a female tetraploid (4n) watermelon plant. The resulting F1 hybrid seeds are triploid (3n). Induction of fruit setting in the F1 hybrid plants requires pollination. As the triploid (3n) F1 hybrid plants do not produce fertile pollen, so called pollinator or polliniser plants have to be planted in the same field. The pollinator plants are diploid (2n). Generally a ratio of pollinator to hybrid plants of around 1 to 3 must be planted in a given scheme for providing sufficient pollen for pollinating all the F1 hybrid plants. The cross-pollination between the diploid (2n) pollinator and the flowers of the female triploid (3n) hybrid plant induces fruit set and leads to the production of seedless triploid fruits on the triploid hybrid plant. The diploid (2n) and tetraploid (4n) parents of the F1 hybrid each produce seed bearing fruits and can both be propagated independently from each other by self-pollination.

Seedless grapes can be produced from plants being either parthenocarp or stenospermocarp. The variety Black Corinth is parthenocarp, whereas Sultanina is stenospermocarp. Vine plants are in general propagated by cuttings and successive grafting to another rootstock.

Irregularities in meiosis can be a factor leading to plants producing seedless fruit. An example for plants producing seedless fruits is given in Zhang et al. (2012, Scientia Horticulture 140, 107-114), disclosing seedless watermelons. A male and female sterile (MFS) mutant was obtained from the progeny of a F1-hybrid after irradiation of its seeds with gamma-rays. Pollen from the MFS mutant was not viable at all. Seedless fruits are produced by the MFS plants, when pollinated with pollen from male fertile plants. The MFS watermelon plant therefore can be classified as being stenospermocarpic. Ovules were also nearly entirely non-viable, as almost no seeds were produced upon cross-pollination of MFS mutants with pollen from different male fertile plants. Incomplete synapsis and abnormal separation of chromatids during meiosis were observed in the MFS mutant and seen to be the cause of male and female sterility. The genes responsible for the effects present in the MFS mutant have not been identified but it seems likely that the phenotype in the MFS mutant is due to a single recessive gene.

Pradillo et al. (2014, Frontiers in Plant Sci. 5, Article 23, do: 10.3389/fpls.2014.00023) reviews the knowledge in the art about genes which are involved in homologous recombination during meiosis in *Arabidospsis*.

Azumi et al. (2002, EMBO J. 21(12), 3081-3095) describe the isolation of an *Arabidopsis* mutant having defects in synapsis and bivalent formation in male meiosis and similar defects, although to a lesser extent, in female meiosis. The mutation was designated "Solo Dancers" (sds) and shown to originate from a single recessive gene. SDS mutants are male sterile and strongly impaired in female fertility. Plants homozygous for the sds mutation are male sterile but at least to a minor extend female fertile, which was demonstrated by cross-pollination of the sds mutant plant with pollen from male fertile plants. SDS mutants therefore are male sterile and strongly impaired in female fertility. The sds gene was identified to belong to the cyclin type protein encoding genes and has been demonstrated to interact with *Arabidopsis* CDKs, Cdc2a and Ccdc2b proteins. SDS however has been identified to be a new, beforehand unknown cyclin type protein. De Muyt et al. (2009, PLOS genet. 5(9) e1000654, doi: 10.1371/journal.pgen.1000654) confirms that the sds *Arabidopsis* mutant has a recombination defect in meiosis and suggest that the defect is caused by a misallocation of another protein (AtDMC1) in the cells during meiosis.

WO2017/202715 describes a recessive mutation in the emb1 gene which results in seedless fruits being produced upon pollination of a plant which is homozygous for the mutant allele. The mutation was found to be in a gene encoding a "cyclin SDS like protein" located on chromosome 7 of the watermelon genome. As pollination is required to induce fruit set and development, the plants are referred to as stenospermocarpic plants. Plants homozygous for the emb1 mutation are male fertile and pollination induces fruit set and development, with seedless fruits developing.

From above discussion it is evident, that the factors determining if plants produce seedless fruits are multiple in nature and can reside in several, e.g. morphologic, physiologic and/or genetic causes.

For producing seedless fruits in stenospermocarpic crops, a female flower part of a plant must be pollinated. The stenospermocarpic crops grown today are male sterile and the only male fertile stenospermocarpy plant described to date is the emb1 mutant of WO2017/202715 above. In the case of male sterile stenospermocarpy besides the female plant, a different male fertile plant (pollinator or polliniser) has to be grown in addition in the same field. As the area used for the pollinator plants is at the expense of the area which is available for the seedless fruit producing female plants, the yield per area under cultivation is reduced. In general, the pollinator plants are normal plants which can also be self-pollinated. Fruits produced by pollinator plants however do produce seeds. In watermelon, the pollinator plants are normally diploid (2n), which upon self-pollination produce seeded fruits, which may in some instances also be harvested and sold separately (see WO2012069539). For commercial reasons these seeded fruits from the pollinator plants must not be mixed with the seedless fruits. Therefore, it has to be ensured, that seedless fruits and seeded fruits are separated upon or after harvest, which may make machine harvesting difficult or impossible or require a further processing step after harvesting. Those additional precautions to be taken increase the input costs in seedless fruit production. In addition, pollinator plants are developed so that they flower and produce sufficient viable pollen at the same time the female plant flowers and its stigma can accept pollen for the induction of fruit set. Thus, the pollinator plant has to fit with the female plant producing seedless fruit in respect to flowering and fertilisation time. If flowering time of the pollinator pant and the respective female plant is not sufficiently synchronised, pollination will not take place or only take place in an insufficient amount of cases. As a result fewer fruits are produced by the stenospermocarpic female plant. Furthermore, it is well known in the art that climate conditions, like rain, heat etc., may influence pollen production of a polliniser plant differently than stigma fertility time of the genotypic different female plant. Therefore, climate conditions can also lead to asynchrony of fertility time of pollinator and female plant with the effect of lowering the yield.

Respective disadvantages are not applicable to the plants of the invention described herein below, as the instant invention also relates to a male fertile stenospermocarpic plant and methods for producing such plants. For the emb1 mutant of WO2017/202715 one major disadvantage is that, when producing seeds which contain the mutant in homozygous form always a mix of seeds containing the homozygous mutant (emb1/emb1) with seeds containing the dominant wild type (WT) allele (emb1/WT; or WT/WT) is produced (due to segregation), while only the homozygous mutant seeds will grow into plants that produce seedless fruits upon pollination. Thus, if one wants to produce a field with only plants which produce seedless fruits, a pre-selection at the DNA level would be needed, to select only those seeds or seedlings which contain the mutant in homozygous form. This would for example involve seed-chipping or other non-destructive genotyping methods for single seeds, or growing seedlings and analysing their DNA for the presence of the mutant allele in homozygous form.

The instant invention, on the other hand, has the advantage that in one aspect (e.g. at least for the mutant emb2 allele present in the deposited watermelon seeds and preferably in progeny thereof comprising the mutant emb2 allele) the presence of the mutant allele can be seen phenotypically already in seedlings, as the recessive mutation, which results in seedless fruits being produced after pollination of the flowers, is associated with a reduction of trichomes on the stem of the plants (referred to as "semi-glabrous" or "less hairy" herein). Selection of seedlings comprising the mutant allele of the invention in homozygous form can, therefore, be carried out by simple visual selection of the semi-glabrous seedlings (comprising the mutant emb2 allele in homozygous form), and discarding the seedlings having a normal pubescent (or "hairy") stem. The semi-glabrous seedlings can then be transplanted into the field and the plants will all produce seedless fruits following pollination.

It is, therefore, an object of the invention to overcome the disadvantages of seedless fruit producing plants currently cultivated or described in e.g. WO2017/202715. It is also an object to provide alternative ways for generating stenospermocarpic plants.

In a population of mutagenized M2 diploid watermelon plants a plant producing seedless or seed defective fruits was observed. The mutant plant was designated EMB2. Surprisingly, pollen of said plant could be used to make backcrosses. Thus, the plants disclosed herein are male fertile.

The back-crosses were self-pollinated and 25% of the plants obtained therefrom produced seedless fruits. A mutant allele (emb2) was identified which caused the seedless fruit phenotype, i.e. when diploid plants homozygous for emb2 (emb2/emb2) were either self-pollinated or pollinated by pollen from another plant, they produced seedless, diploid fruits. Thus, the seedless fruit phenotype occurs in plants being homozygous for a recessive mutation in the emb2 allele (emb2/emb2 genotype in diploid watermelons). "Seedless" or "seed-defective" are used synonymously herein and encompasses that very small, non-viable seeds may be present as e.g. shown in FIG. 2. When referring herein to emb2/emb2 plants being male fertile and/or producing fertile pollen, this does in one aspect not exclude plants having a somewhat reduced fertility compared to a plants comprising the functional wild type Emb2 alleles in homozygous form.

The mutation was mapped to chromosome 9 of the watermelon genome and the causal gene was found to be a ATP-binding cassette transporter family B gene (abbreviated as "ABC transporter" or "ABCB transporter" or Emb2 gene).

ABC transporters are members of a very large superfamily of genes, one of the largest and most ancient family of genes found in all kingdoms, from prokaryotes to protists, fungi, plants and animals. The encoded enzymes are transmembrane proteins, which transport a wide variety of substances across a wide variety of membranes, whereby the transport is coupled to ATP binding and ATP-hydrolysis. Plants have a large number of ABC transporter genes, for example *Arabidopsis thaliana* has 130 ABC transporter genes, and rice has 125 ABC transporter genes. ABC transporters are suggested to have multiplied and diversified during evolution of plants and allowed plants to adapt to terrestrial environment conditions (Jae-Ung Hwang et al. 2016, Molecular Plant 9, 338-355). Although ABC transporter genes are characterized and grouped based on their gene structure, very little is known about most ABC transporters functionally, and no ABC transporter protein has been crystallized so far. Also the substrates of most ABC transporters are not known and difficult to identify.

ABC transporter proteins have a modular structure consisting of two elements, each having a hydrophobic transmembrane domain (TMD), which is usually made up of six membrane-spanning alpha-helices, and a cytosolic domain which is involved in ATB binding, known as the nucleotide binding domain (NBD). In the majority of eukaryotic ABC transporters all four domains are present in one single protein (referred to as full-length transporters), either in "forward" orientation, TMD1-NBD1-TMD2-NBD2, or in "reverse" orientation, NBD1-TMD1-NBD2-TMD2. The two TMD domains are embedded in a membrane to form a transmembrane channel, while the two NBD domains are cytosolic. In a catalytic model ATP binding and hydrolysis likely results in a structural rearrangement of the channel to allow a substrate to move across the membrane (Jasinski et al. 2003, Plant Physiology 131(3):1169-77, FIG. 1).

Based on the NBD domain and other structural features, the proteins are classified into eight subfamilies, ABCA to ABCH. The ABCB subfamily is the second largest ABC protein subfamily in plants. The B subfamily of plant ATP binding cassette transporters is reviewed in Xu et al. 2014 (Biologica Plantarum 58(3): 401-410).

The Emb2 gene of the instant invention encodes an ABCB family protein (also referred to as Emb2 protein herein, or also referred to as ABCB transporter protein), having a TMD1-NBD1-TMB2-NBD2 structure, see e.g. FIG. 1 and FIG. 3. A single nucleotide replacement in the mutant emb2 allele (generated in the EMB2 watermelon plant) results in an amino acid substitution in the conserved TMD1 domain of the encoded protein, whereby the neutral amino acid Glycine at position 202 of the wild type protein (SEQ ID NO: 6) is replaced by the positively charged amino acid Arginine, i.e. the mutant emb2 allele encodes a mutant protein comprising a Gly202Arg amino acid substitution. SEQ ID NO: 1 shows the mutant emb2 protein comprising the amino acid Arginine at position 202, while SEQ ID NO: 6 depicts the wild type protein. SEQ ID NO: 2 depicts the cDNA encoding the mutant emb2 protein of SEQ ID NO: 1, comprising an Adenine at nucleotide 604, instead of a Guanine in the wild type cDNA (SEQ ID NO: 7). Thus, codon GGG (encoding the amino acid Glycine) in the wild type genomic sequence (SEQ ID NO: 8 at nucleotides 3331 to 3333) and wild type cDNA (SEQ ID NO: 7 at nucleotides 604 to 606) is changed into codon AGG (encoding the amino acid Arginine) in the mutant genomic sequence (SEQ ID NO: 3 at nucleotide 3331 to 3333) and in the mutant cDNA (SEQ ID NO: 2 at nucleotides 604 to 606).

The Emb2 gene has twelve exons (these can be visualized by pairwise alignment of the genomic DNA of SEQ ID NO: 3 with the cDNA of SEQ ID NO:2), and the mutation is found in exon 4.

As mentioned, the mutation in the watermelon Emb2 gene (as in the EMB2 plant) is in the conserved TMB1 domain, and actually it is in one of the alpha-helices of the conserved TMB1 domain, shown in FIG. 1, and FIG. 3, as a box (amino acids KVGNFLHYISRFISRFIIGFVR, with the Arginine, R, of the mutant protein in bold).

FIG. 1 also shows that both cucumber (*Cucumis sativus*) and melon (*Cucumis melo*) have genes encoding proteins which are very similar in structure and sequence to the watermelon Emb2 protein. The wild type watermelon Emb2 protein of SEQ ID NO: 6 has 96.5% amino acid sequence identity to the cucumber protein of SEQ ID NO: 4 and 94.9% amino acid sequence identity to the melon protein of SEQ ID NO:5. The domains TMD1, NBD1, TMD2 and NBD2 are highly conserved between these three species of Cucurbitaceae. The alpha-helix domain within TMD1, in which the mutation was found in the watermelon Emb2 protein, is even 100% identical between the three species. It is therefore highly likely that the cucumber and melon ABCB transporter proteins are orthologs of the watermelon Emb2 protein.

Also Solanaceae appear to comprise orthologs of the watermelon Emb2 protein. FIG. 3 shows an alignment of the watermelon emb2 protein of SEQ ID NO: 1 with a tomato (*Solanum lycopersicum*) protein (SEQ ID NO: 9) and with two pepper (*Capsicum annuum*) proteins (SEQ ID NO: 10 and 11). Although the sequence identity to the watermelon protein is 78.8% for the tomato protein and 78.1% for the pepper proteins, the sequence identity of the Solanaceae proteins to each other is much higher, namely 92.2% and 92.1% between tomato a pepper, and the two pepper sequences have a sequence identity of 99.7%. Still, the Solanaceae proteins have the same primary protein structure and also comprise the four conserved domains TMD1, NBD1, TMD2 and NBD2. The Solanaceae Emb2 proteins also comprise an alpha-helix domain in the TMD1 domain which is almost identical (95.5% identity) between the two species, tomato and pepper and comprises the amino acid sequence, being KAGNFLHYISRFLAGFTIGFIR in tomato and KAGNFMHYISRFLAGFTIGFIR in pepper.

The invention relates to plants and plant parts, especially watermelon, cucumber and melon, and optionally other Cucurbitaceae species, comprising a mutation in the ABCB transporter gene (or Emb2 gene) resulting in stenospermocarpy, i.e. seedless fruit development when the mutant allele is in homozygous form. Thus, the invention relates to plants or plant parts comprising at least one mutant emb2 allele, which allele results in seedless fruit production when the plant comprises the allele in homozygous form.

The invention also relates to plants and plant parts, especially tomato and pepper, and optionally other Solanaceae species, comprising a mutation in the ABCB transporter gene (or Emb2 gene) resulting in stenospermocarpy, i.e. seedless fruit development when the mutant allele is in homozygous form.

The "mutant allele of the Emb2 gene" or "mutant emb2 allele" refers herein either to an "induced mutant allele" or a "natural mutant allele" of any Emb2 gene. An induced mutant allele is produced by human intervention, such as gene targeted modification (e.g. through Crispr-Cas9 or other methods) or mutagenesis in e.g. cultivated plants, such as breeding lines. "Natural mutant" alleles are mutant alleles in which the mutation(s) have evolved in wild plants or wild relatives of a species or landraces. Such natural mutant alleles can be introgressed into cultivated plants according to the invention by crossing and selection (e.g. backcrossing). For example an allele comprising a transposable element (TE) insertion is a natural mutant allele. Cultivated plants comprising such natural mutant emb2 alleles are encompassed herein.

A plant endogenous Emb2 gene (or an Emb2 allele thereof) is a gene (or allele) encoding a (wild type, functional) Emb2 protein which comprises at least 60%, 70%, 80%, 90%, 95%, 96%, 97%, 98% or more sequence identity to the watermelon Emb2 protein of SEQ ID NO: 6 and which preferably comprises the four conserved domains in this order: TMD1-NBD1-TMD2-NBD2. A endogenous Emb2 gene or allele of a Cucurbitaceae plant is an a gene (or allele) encoding a (wild type, functional) Emb2 protein which comprises at least 75%, 80%, 85%, 90%, 95%, 96%, 97%, 98%, or more, sequence identity to the watermelon Emb2 protein of SEQ ID NO: 6 and which preferably comprises the four conserved domains in this order: TMD1-NBD1-TMD2-NBD2. A endogenous Emb2 gene or allele of a Solanaceae plant is an a gene (or allele) encoding a (wild type, functional) Emb2 protein which comprises at least 75%, 80%, 85%, 90%, 95%, 96%, 97%, 98%, or more, sequence identity to the tomato Emb2 protein of SEQ ID NO: 9 and which preferably comprises the four conserved domains in this order: TMD1-NBD1-TMD2-NBD2.

In particular encompassed is a plant or plant part of the family Cucurbitaceae (especially watermelon, melon or cucumber) or Solanaceae (especially tomato or pepper) comprising at least one copy of a mutant allele of a gene named Emb2, said gene encodes a Cucurbitaceae Emb2 protein of SEQ ID NO: 6 or a protein comprising at least 75%, 80%, 85%, 90%, 95%, 97% or more sequence identity to SEQ ID NO: 6, or a Solanaceae Emb2 protein of SEQ ID NO: 9 or a protein comprising at least 75% 80%, 85%, 90%, 95%, 97% sequence identity to SEQ ID NO: 9, said mutant allele conferring stenospermocarpy when the mutant allele is in homozygous form. In the plant or plant part comprising said mutant allele of an Emb2 gene, said mutant emb2 allele results in reduced expression or no expression of the (endogenous, wild type) Emb2 gene or said mutant allele encodes a emb2 protein having a decreased function or a loss-of-function compared to the wild type Emb2 protein, i.e. said mutant allele encodes a mutant emb2 protein.

As a result of the mutation in the endogenous Emb2 allele, there is either less or even no wild type Emb2 protein being produced by the mutant allele (e.g. if the mutation is in a regulatory sequence of the endogenous Emb2 allele) in the plant cell and plant, or as a result of the mutation a mutant emb2 protein is produced by the mutant allele, e.g. comprising one or more amino acids replaced, deleted or inserted compared to the functional wild type protein, thereby leading to a reduced function or loss of function of the (mutant) emb2 protein. And consequently, when the mutant allele is in homozygous form in the genome of the plant, the plant will produce seedless fruits upon pollination.

A first embodiment of the present invention concerns plant cells, plant parts and plants, characterized in that the plant cells or plants comprise a mutant emb2 allele which encodes a mutant Emb2 protein which has reduced function/reduced activity or no function/no activity compared to the plant cells and plants comprising a functional wild type Emb2 protein.

A "wild type (WT) Emb2 allele encoding a wild type Emb2 protein" shall be understood to mean a functional allele encoding a functional protein which, when its activity is decreased (see below "decreased activity"), e.g. its gene expression is knocked-down or is entirely knocked-out in a plant or the protein comprises one or more amino acid insertions, replacements or deletions, leads (e.g. in a plant homozygous for a mutant emb2 allele) to male fertile pollen produced by that plant but at the same time leads to the production of seedless fruits of said plant, e.g. when self-pollinated. Likewise, a mutant emb2 allele therefore refers to an allele which comprises one or more mutations in the wild type Emb2 allele, thereby resulting in the stenospermocarpic phenotype, when the mutant emb2 allele is in homozygous form.

In context of the present invention, "decreased activity" of a protein shall mean a decrease in activity of an Emb2 protein when compared to a corresponding wild type plant cell or a corresponding wild type plant. Decrease shall in one aspect comprise an entire knock-out of gene expression, or the production of a loss-of-function or of a decreased function Emb2 protein, e.g. a truncated Emb2 protein may have lost function or decreased function, but also an Emb2 protein comprising one or more amino acids replaced, deleted or inserted, especially in one or several of the conserved domains (TMD1, NBD1, TMD1 and/or NBD2) may have lost function or decreased function. A decrease in activity can be a decrease in the expression of a gene encoding a Emb2 protein (also referred to as knock-down), or a knock-out of the expression of a gene encoding a Emb2 protein and/or a decrease in the quantity of a Emb2 protein in the cells or a decrease of function or a loss-of-function in the enzymatic activity of a Emb2 protein in the cells.

"Knock-out" or "entire knock-out" shall be understood that expression of the respective gene is not detectable anymore.

"Loss of function (in the enzymatic activity)" shall mean in context of the present invention that the protein, although e.g. present in amounts equal or similar to a corresponding wild type protein, does not evoke its effect anymore, i.e. mutant alleles when present in homozygous form in a diploid plant, the plant is male fertile but produces seedless (or seed defective) fruits upon pollination. The terms "non-functional" and "lost activity" shall have the same meaning as "loss of function". All three terms are used herein interchangeably. Thus, when referring to a Emb2 gene encoding a non-functional protein, the gene may be expressed, but the encoded protein is not functional, e.g. due to the protein being truncated or comprising one or more amino acid replacements, insertions or deletions compared to the wild Emb2 protein.

"Decrease of function (in the enzymatic activity)" or "reduced function" shall mean in context of the present invention that the protein although e.g. present in amounts equal or similar to a corresponding wild type protein, does not evoke its effect anymore, i.e. when present in homozygous form in a diploid plant, the plant is male fertile but produces seedless fruits upon pollination.

"Conserved domain" refer to conserved protein domains of the ABCB transporter/Emb2 protein, especially the two transmembrane domains (TMD1 and TMD2) and the two Nucleotide Binding Domains (NBD1 and NBD2) as a whole, or subdomains thereof, e.g. an alpha helix domain in TMD1 or TMD2. Transmembrane domain 1 (TMD1) of Cucurbitaceae refers to the amino acids starting at amino acid number 76 to (and including) amino acid number 339 of SEQ ID NO: 1 or of SEQ ID NO: 6, or an amino acid domain comprising at least 95%, 96%, 97%, 98%, 99% or 100% sequence identity to TMD1 of SEQ ID NO: 1 or SEQ ID NO: 6. Transmembrane domain 1 (TMD1) of Solanaceae refers to the amino acids starting at amino acid number 64 to (and including) amino acid number 327 of SEQ ID NO: 9, or an amino acid domain comprising at least 95%, 96%, 97%, 98%, 99% or 100% sequence identity to TMD1 of SEQ ID NO: 9. Nucleotide Binding Domain 1 (NBD1) of Cucurbitaceae refers to the amino acids starting at amino acid number 391 to (and including) amino acid number 629 of SEQ ID NO: 1 or of SEQ ID NO: 6, or an amino acid domain comprising at least 95%, 96%, 97%, 98%, 99% or 100% sequence identity to NBD1 of SEQ ID NO: 1 or SEQ ID NO: 6. Nucleotide Binding Domain 1 (NBD1) of Solanaceae refers to the amino acids starting at amino acid number 379 to (and including) amino acid number 617 of SEQ ID NO: 9, or an amino acid domain comprising at least 95%, 96%, 97%, 98%, 99% or 100% sequence identity to NBD1 of SEQ ID NO: 9. Transmembrane domain 2 (TMD2) of Cucurbitaceae refers to the amino acids starting at amino acid number 709 to (and including) amino acid number 978 of SEQ ID NO: 1 or of SEQ ID NO: 6, or an amino acid domain comprising at least 95%, 96%, 97%, 98%, 99% or 100% sequence identity to TMD2 of SEQ ID NO: 1 or SEQ ID NO: 6. Transmembrane domain 2 (TMD2) of Solanaceae refers to the amino acids starting at amino acid number 698 to (and including) amino acid number 967 of SEQ ID NO: 9, or an amino acid domain comprising at least 95%, 96%, 97%, 98%, 99% or 100% sequence identity to TMD2 of SEQ ID NO: 9. Nucleotide Binding Domain 2 (NBD2) of Cucurbitaceae refers to the amino acids starting at amino acid number 1025 to (and including) amino acid number 1260 of SEQ ID NO: 1 or of SEQ ID NO: 6, or an amino acid domain comprising at least 95%, 96%, 97%, 98%, 99% or 100% sequence identity to NBD2 of SEQ ID NO: 1 or SEQ ID NO: 6. Nucleotide Binding Domain 2 (NBD2) of Solanaceae refers to the amino acids starting at amino acid number 1014 to (and including) amino acid number 1249 of SEQ ID NO: 9, or an amino acid domain comprising at least 95%, 96%, 97%, 98%, 99% or 100% sequence identity to NBD2 of SEQ ID NO: 9. Sequence identity of two whole proteins, or of a protein domain of two proteins, is determined by pairwise alignment of the whole protein, or of the two protein domains only, e.g. using Emboss Needle pairwise protein alignment. It is noted that when amino acid regions are referred to herein (e.g. starting at amino acid x to/ending at amino acid y), the first mention amino acid and the last mentioned amino acid are included.

"M1 generation" or "M1 plants" in context with the present invention shall refer to the first generation that is produced directly from the mutagenic treatment. A plant grown from seeds treated with a mutagen e.g. is a representative of an M1 generation.

"M2 generation" or "M2 plant" shall refer herein to the generation obtained from self-pollination of the M1 generation. A plant grown from seeds obtained from a self-pollinated M1 plant represents a M2 plant.

The decrease in the expression of an emb2 gene or emb2 allele can, for example, be determined by measuring the quantity of RNA transcripts encoding Emb2 proteins (e.g. mRNA), e.g. using Northern blot analysis or RT-PCR. Here, a reduction preferably means a reduction in the amount of transcripts by at least 50%, in particular by at least 70%, preferably by at least 85% and particularly preferably by at least 95%, compared to the wild type allele. If the decrease is 100% this is a knock-out of the emb2 allele, otherwise it is referred to as a knock-down.

The decrease in the amount of an Emb2 protein, which results in a reduced activity of these proteins in the plant cells or plants concerned, can, for example, be determined by immunological methods such as Western blot analysis, ELISA (Enzyme Linked Immuno Sorbent Assay) or RIA (Radio Immune Assay). Here, a decrease preferably means a reduction in the amount of Emb2 proteins by at least 50%, in particular by at least 70%, preferably by at least 85% and particularly preferably by at least 95%.

Methods for the manufacture of antibodies that react specifically with a designated protein, i.e. that bind specifically to the said protein, are known to the person skilled in the art (see, for example, Lottspeich and Zorbas (Eds.), 1998, Bioanalytik, Spektrum akad, Verlag, Heidelberg, Berlin, ISBN 3-8274-0041-4). The manufacture of such antibodies is offered as a contractual service by several firms.

Concerning the present invention, a decrease of activity of an Emb2 protein in a plant according to the invention can also be determined by the plant phenotype. Plants homozygous for a mutant allele encoding the Emb2 protein or having a decreased activity of an Emb2 protein, produce seedless fruits and are male fertile (produce viable pollen).

In one embodiment the decreased activity of a protein having an ABCB (Emb2) function is decreased in the plant cells or plants according to the invention compared to corresponding wild type plant cells or wild type plants.

In context with the present invention, the term "wild type plant cell" or "wild type plant" means that the plant cells or plants concerned were used as starting material for the production of the plant cells or plants according to the invention, i.e. their genetic information, apart from the introduced (genetic) modification(s) or mutation(s), corresponds to that of a plant cell or plant according to the invention. Thus, it e.g. in a diploid comprises two copies of wild type, fully functional Emb2 alleles. Thus, in one aspect the wild type plant or wild type plant cell is a plant comprising fully functional Emb2 proteins, e.g. regarding watermelon plants or plant cells a diploid watermelon plant producing the protein of e.g. SEQ ID NO: 6 (or a functional variant thereof) and producing seeded fruits upon self-pollination. Or regarding melon plants or cells a diploid melon plant producing the protein of e.g. SEQ ID NO: 5 (or a functional variant thereof), or regarding cucumber plants or cells a diploid cucumber plant producing the protein of e.g. SEQ ID NO: 4 (or a functional variant thereof), or regarding tomato plants or cells a diploid tomato plant producing the protein of e.g. SEQ ID NO: 9 (or a functional variant thereof), or regarding pepper plants or cells a diploid plant producing the protein of e.g. SEQ ID NO: 10 (or a functional variant thereof) or SEQ ID NO: 11 (or a functional variant thereof) and produces seeded fruits upon pollination.

In conjunction with the present invention, the term "corresponding" means that, in the comparison of several objects, the objects concerned that are compared with one another have been kept under the same conditions. In conjunction with the present invention, the term "corresponding" in conjunction with wild type plant cell or wild type plant means that the plant cells or plants, which are compared with one another, have been raised under the same cultivation conditions, that they have the same (cultivation) age and that their genetic information, apart from the introduced (genetic) modification(s) or mutation(s), corresponds to that of a plant cell or plant according to the invention. In case nucleic acid sequences of RNA and DNA molecules are compared with each other or said to correspond to each other, it is well understood in the art that a thymine (T) in a DNA molecule is equivalent with uridine (U) in an RNA molecule. Thus, a T in a DNA sequence is to be understood to be replaced by a U in an RNA sequence and vice versa, when such molecules are compared with each other.

In one embodiment according to the invention, the (wild type, functional) Emb2 protein of a wild type plant cell, plant part or wild type plant is encoded by nucleic acid molecules selected from the group consisting of:
a) nucleic acid molecules, which encode a protein with the amino acid sequence given under SEQ ID NO: 6 (watermelon Emb2 protein) or SEQ ID NO: 4 (cucumber Emb2 protein) or SEQ ID NO: 5 (melon Emb2 protein) or SEQ ID NO: 9 (*Solanum lycopersicum* Emb2 protein) or SEQ ID NO: 10 or 11 (*Capsicum annuum* Emb2 protein);
b) nucleic acid molecules, which encode a protein, the sequence of which has an identity of at least 70%, 75%, more preferably at least 80%, even further preferred at least 90%, or particularly preferred at least 95%, 96%, 97%, 98% or 99% with the amino acid sequence given under SEQ ID NO: 6 or SEQ ID NO: 4 or SEQ ID NO: 5 or SEQ ID NO: 9 or SEQ ID NO: 10 or SEQ ID NO: 11;
c) nucleic acid molecules, which comprise the nucleotide sequence shown under SEQ ID NO: 7 or SEQ ID NO: 8 or a complimentary sequence thereof;
d) nucleic acid molecules, which have an identity of at least 70%, 75%, more preferably at least 80%, even further preferred at least 90% or particularly preferred at least 95% with the nucleotide sequences described under c);
e) nucleic acid molecules, which hybridise with at least one strand of the nucleic acid molecules described under a), b), c), or d) under stringent conditions;
f) nucleic acid molecules, the nucleotide sequence of which deviates from the sequence of the nucleic acid molecules identified under a), b), c) or d) due to the degeneration of the genetic code; and
g) nucleic acid molecules, which represent fragments, allelic variants and/or derivatives of the nucleic acid molecules identified under a), b), c) or d).

The genomic nucleotide sequence shown under SEQ ID NO:8, and the coding sequence as indicated in SEQ ID NO:7, encodes a wild type Emb2 protein of *Citrullus lanatus* (watermelon) having the amino acid sequence as shown under SEQ ID NO: 6.

SEQ ID NO: 6 (watermelon), SEQ ID NO: 4 (cucumber) and SEQ ID NO: 5 (melon) encode wild type Emb2 proteins of Cucurbitaceae species. Functional allelic variants of these wild type Emb2 proteins may exist, e.g. functional Emb2 proteins (ABCB transporter proteins) which comprise the four conserved domains TMD1, NBD1, TMD2 and NBD2 in this order. The nucleic acid molecules (i.e. wild type Emb2 alleles) encoding such functional ABCB transporter proteins may, thus, encode a Emb2 protein, the sequence of which has an identity of at least 75%, more preferably at least 80%, even further preferred at least 90%, or particularly preferred at least 95%, 96%, 97%, 98% or 99% sequence identity with the amino acid sequence given under SEQ ID NO: 6 or SEQ ID NO: 4 or SEQ ID NO: 5. Preferably the amino acid sequences of the conserved domains TMD1, NBD1, TMD2 and NBD2 are highly conserved in the functional variants, i.e. preferably the functional protein variants comprise a TMD1 of Cucurbitaceae (as defined above), a NBD1 of Cucurbitaceae (as defined above), a TMD2 of Cucurbitaceae (as defined above) and a NBD2 of Cucurbitaceae (as defined above).

SEQ ID NO: 9 (tomato), SEQ ID NO: 10 (pepper) and SEQ ID NO: 11 (pepper) encode wild type Emb2 proteins of Solanaceae species. Functional variants of these wild type Emb2 proteins may exist, e.g. functional Emb2 proteins (ABCB transporter proteins) which comprise the four conserved domains TMD1, NBD1, TMD2 and NBD2 in this order. The nucleic acid molecules (i.e. wild type Emb2 alleles) encoding such functional ABCB transporter proteins may, thus, encode a Emb2 protein, the sequence of which has an identity of at least 75%, more preferably at least 80%, even further preferred at least 90%, or particularly preferred at least 95%, 96%, 97%, 98% or 99% sequence identity with the amino acid sequence given under SEQ ID NO: 9 or SEQ ID NO:10 or SEQ ID NO:11. Preferably the amino acid sequences of the conserved domains TMD1, NBD1, TMD2 and NBD2 are highly conserved in the functional variants, i.e. preferably the functional protein variants comprise a TMD1 of Solanaceae (as defined above), a NBD1 of Solanaceae (as defined above), a TMD2 of Solanaceae (as defined above) and a NBD2 of Solanaceae (as defined above).

The plant cells, plant parts or plants according to the invention, which comprise at least one mutant allele of an Emb2 gene, can be plant cells from any species or plants of any species. The plant cells according to the invention can be monocotyledonous and dicotyledonous plant cells, the plants according to the invention can be monocotyledonous and dicotyledonous plants. Preferably the plant cells, plant parts, plants or seeds comprising the mutant allele of the Emb2 gene as described herein are cultivated plants, having good agronomic characteristics, such as inbred lines, breeding lines, varieties or cultivars. Preferably the plant cells according to the invention are plant cells of vegetables (vegetable plant cells) or the plants are vegetable plants, in particular vegetables like tomato, onion, leek, garlic, carrots, pepper, asparagus, artichoke, celeriac, cucumber, melon, gourd, squash, lettuce, watermelon, spinach, cabbage (*Brassica oleracea*), corn salad, aubergine and okra. More preferred are plant cells from vegetables (vegetable plant cells) or vegetable plants from the Cucurbitaceae family or Solanaceae family. Cucurbitaceae plant cells and plants according to the invention comprise squash (*Cucurbita pepo, Cucurbtia maxima, Cucurbita moschata, Lagenaria siceraria*), melon (*Cucumis melo*), cucumber (*Cucumis sativus*), watermelon (*Citrullus lanatus*). Solanaceae plant cells and plants comprise tomato (*Solanum lycopersicum*) or pepper (*Capsicum annuum*) plant cells or plants. In particular preferred are plant cells from watermelon (*Citrullus lanatus*) or melon (*Cucumis melo*), or watermelon (*Citrullus lanatus*)

or melon (*Cucumis melo*) plants. In one embodiment the plants and plant cells are cultivated plants of these species, such as inbred lines or varieties having good agronomic characteristics, especially producing marketable produce (e.g. fruits) of good quality and uniformity.

Another embodiment of the present invention concerns plants and plant parts comprising plant cells according to the invention.

A further embodiment of the present invention is a plant cell or plant, characterised in that the plant cell or plant has a 'decreased activity' of a Emb2 protein compared to a corresponding wild type plant cell or wild type plant, wherein the (wild type, functional) Emb2 protein of a corresponding wild type plant cell or wild type plant (i.e. a wild type Emb2 allele) is encoded by nucleic acid molecules selected from the group consisting of:
  a) Nucleic acid molecules, which encode a protein with the amino acid sequence given under SEQ ID NO: 6 (watermelon Emb2 protein) or SEQ ID NO: 4 (cucumber Emb2 protein) or SEQ ID NO: 5 (melon Emb2 protein) or SEQ ID NO: 9 (*Solanum lycopersicum* Emb2 protein) or SEQ ID NO: 10 or SEQ ID NO: 11 (*Capsicum annuum* Emb2 protein);
  b) Nucleic acid molecules, which encode a protein, the sequence of which has an identity of at least at least 70%, 75%, more preferably at least 80%, even further preferred at least 90% or particularly preferred at least 95%, 96%, 97%, 98% or 99% with the amino acid sequence given under SEQ ID NO: 6 or SEQ ID NO: 4 or SEQ ID NO: 5 or SEQ ID NO: 9 or SEQ ID NO: 10 or SEQ ID NO: 11;
  c) Nucleic acid molecules, which comprise the nucleotide sequence shown under SEQ ID NO: 7 or SEQ ID NO: 8 or a complimentary sequence thereof;
  d) Nucleic acid molecules, which have an identity of at least 70%, 75%, more preferably at least 80%, even further preferred at least 90% or particularly preferred at least 95% with the nucleotide sequences described under c);
  e) Nucleic acid molecules, which hybridise with at least one strand of the nucleic acid molecules described under a), b), c), or d) under stringent conditions;
  f) Nucleic acid molecules, the nucleotide sequence of which deviates from the sequence of the nucleic acid molecules identified under a), b), c) or d) due to the degeneration of the genetic code; and
  g) Nucleic acid molecules, which represent fragments, allelic variants and/or derivatives of the nucleic acid molecules identified under a), b), c) or d).

"Sequence identity" and "sequence similarity" can be determined by alignment of two peptide (protein, amino acid) or two nucleotide sequences using global or local alignment algorithms. Sequences may then be referred to as "substantially identical" or "substantial identity" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm for aligning two sequences, over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS, accessible at world wide web under ebi.ac.uk/Tools/emboss/. Alternatively sequence similarity or identity may be determined by searching against databases (e.g. EMBL, GenBank) by using commonly known algorithms and output formats such as FASTA, BLAST®, etc., but hits should be retrieved and aligned pairwise to compare sequence identity. Two proteins or two protein domains, or two nucleic acid sequences have "substantial sequence identity" if the percentage sequence identity is at least 60%, 70%, 75%, 80%, 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as "variants" or "allelic variants" or "derivatives" herein. Other allelic variants of the Emb2 protein encoding genes/alleles and Emb2 proteins than the specific nucleic acid and protein sequences disclosed herein can be identified. So for example Emb2 proteins having substantial sequence identity to the protein of SEQ ID NO: 6 (watermelon), or to the protein of SEQ ID NO: 4 (cucumber) or to the protein of SEQ ID NO: 5 (melon), or to the protein of SEQ ID NO: 9 (tomato), or to the protein of SEQ ID NO: 10 (pepper), or to the protein of SEQ ID NO: 11 (pepper) are variants of the provided proteins.

As mentioned, allelic variants of the Emb2 gene may exist in other vegetable plant cells or plants, either in cultivated plants or in wild plants or wild relatives, in particular vegetables like tomato, onion, leek, garlic, carrots, pepper, asparagus, artichoke, gourd, squash, celeriac, cucumber, melon, lettuce, watermelon, spinach, cabbage (*Brassica*) species, corn salad and okra. Mutations in such allelic variants of the Emb2 protein-encoding gene have the same effect on male and female fertility and/or seedless fruit production in other vegetable plants. Particularly allelic variants of a Emb2 gene may exist in plant cells or plants from the Cucurbitaceae family, like melon (*Cucumis melo*), cucumber (*Cucumis sativus*), watermelon (*Citrullus lanatus*), squash (*Cucurbita pepo, Cucurbtita maxima, Cucurbita moschata, Lagenaria siceraria*), or wild plants or wild relatives of these species; particular preferred allelic variants of a Emb2 gene may exist in plant cells of watermelon (*Citrullus lanatus*), melon (*Cucumis melo*) or cucumber (*Cucumis sativus*) or watermelon (*Citrullus lanatus*) or melon (*Cucumis melo*) or cucumber (*Cucumis sativus*) plants, or wild plants or wild relatives of these. Additionally allelic variants of a Emb2 gene may also exist in plant cells or plants from the Solanaceae family, like tomato (*Solanum lycopersicum*) or wild relatives of tomato (*S. pimpinelli, S. cheesmaniae, S. galapagense, S. pimpinellifolium, S. chmielewskii, S. habrochaites, S. neorickii, and S. pennelli, S. arcanum, S. chilense, S. corneliomulleri, S. huaylasense, and S. peruvianum*), pepper (*Capsicum annuum*), *Solanum melongena* (aubergine), *Solanum tuberosum* (potato), etc.

Allelic variants may also exist in other cultivated crop plants, such as filed crops (e.g. *Brassica* species, maize, rice, soybean, wheat, barley, cotton, tobacco, coffee, etc.) or fruit crops (e.g. grape, apple, plum, citrus fruits, strawberry, etc.).

It is noted that the Emb2 proteins of the Cucurbitaceae have a very high sequence identity to each other (at least 94% for the provided sequences) and the Emb2 proteins of the Solanaceae also have a high sequence identity to each other (at least 92% for the provided sequences). The sequence identity between Cucurbitaceae and Solanaceae sequences is also quite high, at least 78%, see Table A below.

TABLE A

Emb2 protein sequence identity (pairwise alignment using the Emboss program Needle)

| | Watermelon (SEQ ID NO: 6) | Cucumber (SEQ ID NO: 4) | Melon (SEQ ID NO: 5) | Tomato (SEQ ID NO: 9) | Pepper (SEQ ID NO: 10) |
|---|---|---|---|---|---|
| Watermelon (SEQ ID NO: 6) | 100% | 96.5% | 94.9% | 78.8% | 78.1% |
| Cucumber (SEQ ID NO: 4) | | 100% | 95.9% | 78.6% | 78.1% |
| Melon (SEQ ID NO: 5) | | | 100% | 79.0% | 78.9% |
| Tomato (SEQ ID NO: 9) | | | | 100% | 92.2% |
| Pepper (SEQ ID NO: 10) | | | | | 100% |

This high amino acid sequence identity of the entire Emb2 proteins is also reflected in the high sequence identity of the conserved domains. Within the Cucurbitaceae (watermelon, melon, cucumber) and within the Solanaceae (tomato, pepper) each domain (TMD1, NBD1, TMD2 and NBD2) is highly conserved, with at least 90% amino acid identity. But also the Cucurbitaceae domains and the Solanaceae domains have a relatively high sequence identity to each other. For example TMD1 of watermelon of SEQ ID: 6 is 84.8% identical to the tomato TMD1 domain of SEQ ID NO: 9 and 84.1% to the pepper TMD1 of SEQ ID NO: 10; NBD1 of watermelon of SEQ ID: 6 is 89.1% identical to the tomato NBD1 domain of SEQ ID NO:9 and 87.4% to the pepper NBD1 of SEQ ID NO: 10; TMD2 of watermelon of SEQ ID: 6 is 77.8% identical to the tomato TMD2 domain of SEQ ID NO:9 and 78.9% to the pepper TMD2 of SEQ ID NO: 10; and NBD2 of watermelon of SEQ ID: 6 is 83.9% identical to the tomato TMD2 domain of SEQ ID NO:9 and 85.2% to the pepper NBD2 of SEQ ID NO: 10.

"Stringent hybridisation conditions" can be used to identify nucleotide sequences, which are substantially identical to a given nucleotide sequence. Stringent conditions are sequence dependent and will be different under different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridise to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually two) in 0.2×SSC at a temperature of at least 50° C., usually about 55° C., for 20 min, or equivalent conditions. See also Sambrook et al. (1989) and Sambrook and Russell (2001).

A decrease in the activity of a Emb2 protein in plant cells or plants according to the invention can also be achieved by a gene silencing effect.

In a further embodiment of the invention the decreased activity of a Emb2 protein in plant cells or plants according to the invention is caused by a gene silencing effect.

The plant cells according to the invention and plants according to the invention having a decreased activity of a Emb2 protein can be produced by different methods causing a gene silencing effect known to the person skilled in the art. These include, for example, the expression of a corresponding antisense RNA or of a double-stranded RNA construct (RNAi technology), the provision of nucleic acid molecules or vectors, which impart a co-suppression effect, the expression of a correspondingly constructed ribozyme that splits specific transcripts, which code a Emb2 protein.

The decrease of the Emb2 protein activity in plant cells and plants according to the invention can be brought about by expressing an antisense sequence in respective plant cells or plants.

The decrease of the Emb2 protein activity in plant cells and plants according to the invention can be brought about by the simultaneous expression of sense and antisense RNA molecules (RNAi technology) of the respective target gene to be repressed, preferably of the Emb2 protein encoding gene or allele.

In addition to this, it is known that in planta the formation of double-stranded RNA molecules of promoter sequences can lead in trans to methylation and transcriptional inactivation of homologous copies of this promoter (Mette et al., EMBO J. 19, (2000), 5194-5201). The decrease of the Emb2 protein activity in plant cells and plants according to the invention can be brought about by the simultaneous expression of sense and antisense RNA molecules (RNAi technology) of promoter sequences initiating transcription of the respective target gene to be repressed, preferably of the Emb2 protein encoding gene or allele.

Ribozymes have also been described in the art to decrease the expression of proteins by cleaving RNA molecules encoding the target gene.

Additional discussion of the respective gene silencing technologies known to a person skilled in the art will be provided herein further below and are applicable to the plant cells or plants according to the invention accordingly.

"Gene silencing effect" refers to a down-regulation or complete inhibition of gene expression of the target gene or gene family. Silenced plant cells or plants produce lower amounts of translation eligible transcripts (including mRNA) for a respective target gene or allele, compared to corresponding wild type plant cells or corresponding wild type plants. The lower amounts of translation eligible transcripts (including mRNA) may be due to targeted degradation of respective transcripts.

A "target gene or allele" shall be understood to be the gene or allele or gene family (or one or more specific alleles of the gene) which has to be modulated for conferring an organism (e.g. plant cell or plant) to produce a desired phenotype. Concerning male sterile seedless fruit producing plants e.g. (a) target gene(s) or (a) target allele(s) is/are the Emb2 protein encoding gene(s).

In a further embodiment of the invention the decreased activity of a Emb2 protein in plant cells or plants according to the invention is caused by immunomodulation methods.

A further possible way in which to reduce the enzymatic activity of proteins in plant cells or plants is the so-called immunomodulation method. It is known that an in planta expression of antibodies, which specifically recognize a plant protein, results in a decrease of the activity of the proteins concerned. Additional discussion of the respective technology known to a person skilled in the art will be provided herein further below.

A further embodiment of the invention, are plant cells or plants characterised in that they comprise a mutant allele of a Emb2 protein-encoding gene. The mutant allele of a Emb2 protein-encoding gene can be present in homozygous or heterozygous state. In one aspect, the mutant allele encodes a Emb2 protein having decreased function or loss of function of the encoded mutant protein. The mutant allele may encode a protein with one or more amino acids replaced, inserted or deleted, resulting in a protein having decreased function or loss of function compared to the wild type (functional) Emb2 protein. In another aspect the mutant allele is an allele which results in a reduced expression of the Emb2 allele or no expression of the Emb2 allele, e.g. through a mutation in a regulatory region, such as the promoter of the Emb2 allele.

Thus, in one aspect of the invention the plant cells or plants comprise a mutant allele of a Emb2 protein-encoding gene, which wild type Emb2 protein-encoding gene encodes a protein with the amino acid sequence given under SEQ ID NO: 6 (watermelon Emb2 protein) or SEQ ID NO: 4 (cucumber Emb2 protein) or SEQ ID NO: 5 (melon Emb2 protein) or SEQ ID NO: 9 (*Solanum lycopersicum* Emb2 protein) or SEQ ID NO: 10 or 11 (*Capsicum annuum* Emb2 protein), or which encode a protein, the sequence of which has an identity of at least 70%, 75%, 78%, more preferably at least 80%, even further preferred at least 90%, or particularly preferred at least 95%, 96%, 97% or 98% or 99% with the amino acid sequence given under SEQ ID NO: 6, or SEQ ID NO:4, or SEQ ID NO:5, or SEQ ID NO: 9, or SEQ ID NO: 10, or SEQ ID NO: 11.

Especially a plant or plant part of the family Cucurbitaceae is provided comprising at least one copy of a mutant allele of a gene named Emb2, said (wild type) gene encodes a Cucurbitaceae Emb2 protein of SEQ ID NO: 6 or a protein comprising at least 75% sequence identity to SEQ ID NO: 6, said mutant allele conferring stenospermocarpy when the mutant allele is in homozygous form.

Also a plant or plant part of the family Solanaceae is provided comprising at least one copy of a mutant allele of a gene named Emb2, said (wild type) gene encodes a Solanaceae Emb2 protein of SEQ ID NO: 9 or a protein comprising at least 75% sequence identity to SEQ ID NO: 9, said mutant allele conferring stenospermocarpy when the mutant allele is in homozygous form.

Thus, in one aspect the mutant allele encodes an Emb2 protein which comprises one or more amino acids inserted, deleted or replaced compared to the functional wild type Emb2 protein. In principle any amino acid insertion, deletion and/or replacement compared to the functional wild type protein may lead to the mutant protein having reduced function or no function, i.e. resulting in seedless fruit development when the mutant allele is in homozygous form. In one aspect of the invention one or more amino acids are inserted, deleted or replaced in at least one of the conserved domains, such as the TMD1 domain, the NBD1 domain, the TMD2 domain and/or the NBD2 domain, resulting in the Emb2 protein having decreased function or loss-of-function. Optionally the mutant allele encodes a mutant Emb2 protein comprising one or more amino acids being inserted, replaced or deleted in the linker domain, i.e. the amino acids between the NBD1 and TMD2 domain is encompassed, as this can also result in a loss of function or reduced function Emb2 protein in the plant or plant cell.

In one aspect the mutation in an endogenous Emb2 allele is induced by e.g. mutagenesis or genome editing techniques, such as Crispr-Cas9, Crispr-Cpf1 or others. It is understood that any transgene or vector used to induce the mutation is preferably segregated out afterwards, resulting in a non-transgenic plant comprising only the endogenous mutant allele. "Induced mutant" alleles are thus mutant alleles in which the mutation(s) is/are/have been induced by human intervention, e.g. by mutagenesis via physical or chemical mutagenesis methods or via e.g. tissue culture (as described in e.g. Zhang et al, Plos 9(5) e96879), including also genome editing techniques.

The conserved domains of an Emb2 protein of Cucurbitaceae (TMD1, NBD1, TMD2 and NBD2 of Cucurbitaceae) can be identified by pairwise alignment of an Emb2 protein with e.g. the watermelon wild type protein of SEQ ID NO: 6 or with the mutant watermelon emb2 protein of SEQ ID NO: 1. See also FIG. 1.

The conserved domains of an Emb2 protein of Solanaceae (TMD1, NBD1, TMD2 and NBD2 of Solanaceae) can be identified by pairwise alignment of an Emb2 protein with e.g. the tomato wild type protein of SEQ ID NO: 9. See also FIG. 3.

TMD1 Domain:

A preferred mutant emb2 allele is a mutant allele of a Cucurbitaceae emb2 allele (especially an allele of watermelon, melon or cucumber) and comprises an (at least one) amino acid insertion, deletion and/or replacement in the TMD1 domain, i.e. in one aspect in a transmembrane domain 1 (TMD1) of Cucurbitaceae, i.e. in the amino acids starting at amino acid number 76 to (and including) amino acid number 339 of SEQ ID NO: 1 or of SEQ ID NO: 6, or in a TMD1 amino acid domain of another Emb2 protein (e.g. a protein comprising at least at least 70%, 75%, more preferably at least 80%, even further preferred at least 90%, or particularly preferred at least 95%, 96%, 97%, 98% or 99% with the amino acid sequence given under SEQ ID NO: 6 or SEQ ID NO:4 or SEQ ID NO:5), wherein said TMD1 domain comprises at least 95%, 96%, 97%, 98%, 99% or 100% sequence identity to TMD1 of SEQ ID NO: 1 or SEQ ID NO: 6. For example one or more amino acids may be inserted, deleted or replaced in the TMD1 domain of SEQ ID NO: 1 or SEQ ID NO: 6 (starting at amino acid 76 and ending at amino acid 339), or in the TMD1 domain of SEQ ID NO: 4 (starting at amino acid 79 and ending at amino acid 342), or in the TMD1 domain of SEQ ID NO: 5 (starting at amino acid 44 and ending at amino acid 307).

In one aspect the mutant allele comprising an amino acid insertion, deletion or replacement in a TMD1 domain, comprises said amino acid insertion, replacement or deletion in the conserved alpha-helix domain of the TMD1 domain of a Cucurbitaceae Emb2 protein. The alpha-helix domain of the TMD1 domain of Cucurbitaceae Emb2 proteins comprises amino acids KVGNFLHYISRFISGFIIGFVR of SEQ ID NO: 12 or an alpha helix domain comprising at least 90% sequence identity to SEQ ID NO: 12 (e.g. amino acids 188 to 209 of SEQ ID NO: 6; amino acids 191 to 212 of SEQ ID NO: 4; amino acids 156 to 177 of SEQ ID NO: 5, or the equivalent amino acids of another Cucurbitaceae Emb2 protein), thus in one aspect one or more amino acids of amino acids are inserted, replaced or deleted in this domain. In one aspect the mutant allele comprises one or more amino acids inserted, deleted or replaced in the alpha helix domain of a Cucurbitaceae Emb2 protein, wherein said alpha helix domain of said Cucurbitaceae Emb2 protein comprises the amino acid sequence of SEQ ID NO: 12 or an amino acid sequence which comprises at least 90%, 91%, 92%, 93%, 94%, 95%, 96%, 97%, 98% sequence identity to SEQ ID NO: 12.

In one aspect the second Glycine (G) of the alpha helix domain is replaced by a different amino acid, i.e. Glycine at amino acid 202 of SEQ ID NO: 6, Glycine at amino acid 205 of SEQ ID NO: 4 or the Glycine at amino acid 170 of SEQ ID NO: 5, or the equivalent Glycine of another Cucurbitacea Emb2 protein. In one aspect the amino acid number 15 of SEQ ID NO: 12, or of a sequence comprising at least 90% sequence identity to SEQ ID NO: 12, is replaced by a different amino acid. In one particular embodiment the second Glycine (G) of the alpha helix domain (e.g. the Glycine at amino acid number 15 of SEQ ID NO: 12 or of a sequence comprising at least 90% sequence identity to SEQ ID NO: 12) is replaced by a different amino acid, in one aspect by a polar (hydrophilic) amino acid, e.g. an Arginine (R), an Asparagine (N), Aspartate (D), Glutamate (E), Glutamine (Q), Histidine (H), Lysine (K), Serine (S), Threonine (T), Tyrosine (Y), preferably by an Arginine (R), especially by a charged amino acid (Arginine and Lysine are positively charged and Aspartic acid and Glutamic acid have a negatively charged side chain).

In a further embodiment any non-polar (comprising a hydrophobic side chain) amino acid of the TMD1 domain, or of the alpha-helix domain of the TMD1 domain, of the Cucurbitaceae Emb2 proteins is replaced by a polar amino acid (comprising a hydrophilic side chain). Non-polar amino acids are Alanine (A or Ala), Cysteine (C or Cys), Glycine (G or Gly), Isoleucine (I or Ile), Leucine (L or Leu), Methionine (M or Met), Phenylalanine (F or Phe), Proline (P or Pro), Tryptophan (W or Trp), Valine (V or Val). Polar amino acids are Arginine (R or Arg), Asparagine (N or Asn), Aspartate (D or Asp), Glutamate (E or Glu), Glutamine (Q or Gln), Histidine (H or His), Lysine (K or Lys), Serine (S or Ser), Threonine (T or Thr), Tyrosine (Y or Tyr).

In yet another aspect any Glycine and/or or Proline of the TMD1 domain, or of the alpha helix domain in the TMD1 domain referred to above, is replaced by another amino acid. Glycine and Proline are commonly highly conserved in protein families, and their replacement will likely affect the secondary structure of the protein and thereby lead to a reduced function or loss of function.

Thus, one particular mutant allele comprises a replacement of amino acid G (Glycine) 202 of SEQ ID NO: 6 by R (Arginine). This mutant allele is present in the watermelon seed deposit and can thus either be obtained from the deposit, or generated de novo. Without limiting the invention, it is thought that mutants in the TMD1 domain (and or in the TMD2 domain), optionally in the alpha helix domain of the TMD1 domain, result in proteins having reduced function or loss of in vivo function and thereby lead to stenospermocarpy.

Another particular mutant allele comprises a replacement of amino acid Aspartic acid (Asp or D) 183 of SEQ ID NO: 1 or 6, or of amino acid Asp186 of SEQ ID NO: 4, or of amino acid Asp151 of SEQ ID NO: 5 by another amino acid, or the equivalent amino acid in the TMD1 domain of another emb2 protein. For example the Asp (D) at that position is replaced by a Asparagine (Asn or N).

Another mutant emb2 allele is a mutant allele of a Solanaceae emb2 allele (especially an allele of tomato or pepper) and comprises an amino acid insertion, deletion or replacement in the TMD1 domain, i.e. in one aspect in a transmembrane domain 1 (TMD1) of Solanaceae, i.e. in the amino acids starting at amino acid number 64 to (and including) amino acid number 327 of SEQ ID NO: 9, or in a TMD1 amino acid domain of another Emb2 protein (e.g. a protein comprising at least at least 70%, more preferably at least 80%, even further preferred at least 90%, or particularly preferred at least 95% with the amino acid sequence given under SEQ ID NO: 9 or SEQ ID NO:10 or SEQ ID NO:11), wherein said TMD1 domain comprises at least 95%, 96%, 97%, 98%, 99% or 100% sequence identity to TMD1 of SEQ ID NO: 9. For example one or more amino acids may be inserted, deleted or replaced in the TMD1 domain of SEQ ID NO: 9 (starting at amino acid 64 and ending at amino acid 327), or in the TMD1 domain of SEQ ID NO: 10 (starting at amino acid 61 and ending at amino acid 324), or in the TMD1 domain of SEQ ID NO: 11 (starting at amino acid 61 and ending at amino acid 324).

In a different aspect the mutant allele comprising an amino acid insertion, deletion or replacement in a TMD1 domain, comprises said amino acid insertion, replacement or deletion in the conserved alpha-helix domain of the TMD1 domain of a Solanaceae Emb2 protein. The alpha-helix domain of the TMD1 domain of Solanaceae Emb2 proteins comprises amino acids of SEQ ID NO: 13 (amino acids KAGNFLHYISRFLAGFTIGFIR) or an alpha helix domain comprising at least 90% sequence identity to SEQ ID NO: 13, e.g. KAGNFMHYISRFLAGFTIGFIR (e.g. amino acids 176 to 197 of SEQ ID NO: 9; amino acids 173 to 194 of SEQ ID NO: 10; amino acids 173 to 194 of SEQ ID NO: 11, or the equivalent amino acids of another Solanaceae Emb2 protein), thus in one aspect one or more amino acids of amino acids are inserted, replaced or deleted in this domain. In one aspect the mutant allele comprises one or more amino acids inserted, deleted or replaced in the alpha helix domain of a Solanaceae Emb2 protein, wherein said alpha helix domain of said Solanaceae Emb2 protein comprises the amino acid sequence of SEQ ID NO: 13 or an amino acid sequence which comprises at least 90%, 91%, 92%, 93%, 94%, 95%, 96%, 97%, 98% sequence identity to SEQ ID NO: 13. For example, the alpha helix domain of tomato comprises 95.5% sequence identity with the alpha helix domain of pepper.

In one aspect the second Glycine (G) of the alpha helix domain is replaced by a different amino acid, i.e. Glycine at amino acid 190 of SEQ ID NO: 9, Glycine at amino acid 187 of SEQ ID NO: 10 or the Glycine at amino acid 187 of SEQ ID NO: 11, or the equivalent Glycine of another Solanaceae Emb2 protein. In one aspect the amino acid at position 15 of SEQ ID NO: 13 or an alpha helix domain sequence comprising at least 90% sequence identity to SEQ ID NO: 13, is replaced by a different amino acid. In one particular embodiment the second Glycine (G) of the alpha helix domain (e.g. the Glycine at amino acid 15 of SEQ ID NO: 13 or in a domain comprising at least 90% identity to SEQ ID NO: 13) is replaced by a polar (hydrophile) amino acid, e.g. an Arginine (R), an Asparagine (N), Aspartate (D), Glutamate (E), Glutamine (Q), Histidine (H), Lysine (K), Serine (S), Threonine (T), Tyrosine (Y), preferably by an Arginine (R).

In a further embodiment any non-polar (comprising a hydrophobic side chain) amino acid of the TMD1 domain, or of the alpha-helix domain of the TMD1 domain, of the Solanaceae Emb2 proteins is replaced by a polar amino acid (comprising a hydrophilic side chain). Non-polar amino acids are Alanine (A or Ala), Cysteine (C or Cys), Glycine (G or Gly), Isoleucine (I or Ile), Leucine (L or Leu), Methionine (M or Met), Phenylalanine (F or Phe), Proline (P or Pro), Tryptophan (W or Trp), Valine (V or Val). Polar amino acids are Arginine (R or Arg), Asparagine (N or Asn), Aspartate (D or Asp), Glutamate (E or Glu), Glutamine (Q or Gln), Histidine (H or His), Lysine (K or Lys), Serine (S or Ser), Threonine (T or Thr), Tyrosine (Y or Tyr).

In yet another aspect any Glycine and/or or Proline of the TMD1 domain, or of the alpha helix domain in the TMD1 domain referred to above, is replaced by another amino acid. Glycine and Proline are commonly highly conserved in protein families, and their replacement will likely affect the secondary structure of the protein and thereby lead to a reduced function or loss of function.

A particular mutant allele comprises a replacement of amino acid Aspartic acid (Asp) 171 of SEQ ID NO: 9, or of amino acid Asp168 of SE ID NO: 10, or of amino acid Asp 168 of SEQ ID NO: 11 by another amino acid, or the equivalent amino acid in the TMD1 domain of another emb2 protein. For example the Asp (D) at that position is replaced by a Asparagine (Asn or N).

NBD1 Domain:

Another mutant emb2 allele is a mutant allele of a Cucurbitaceae emb2 allele (especially an allele of watermelon, melon or cucumber) and comprises an (at least one) amino acid insertion, deletion and/or replacement in the NBD1 domain, i.e. in one aspect in a Nucleotide Binding Domain 1 (NBD1) of Cucurbitaceae, i.e. in the amino acids starting at amino acid number 391 to (and including) amino acid number 629 of SEQ ID NO: 1 or of SEQ ID NO: 6, or in a NBD1 amino acid domain of another Emb2 protein (e.g. a protein comprising at least at least 70%, 75%, more preferably at least 80%, even further preferred at least 90%, or particularly preferred at least 95%, 96%, 97%, 98% or 99% with the amino acid sequence given under SEQ ID NO: 6 or SEQ ID NO: 4 or SEQ ID NO:5), wherein said NBD1 domain comprises at least 95%, 96%, 97%, 98%, 99% or 100% sequence identity to NBD1 of SEQ ID NO: 1 or SEQ ID NO: 6. For example one or more amino acids may be inserted, deleted or replaced in the NBD1 domain of SEQ ID NO: 1 or SEQ ID NO: 6 (starting at amino acid 391 and ending at amino acid 629), or in the NBD1 domain of SEQ ID NO: 4 (starting at amino acid 394 and ending at amino acid 632), or in the NBD1 domain of SEQ ID NO: 5 (starting at amino acid 359 and ending at amino acid 597).

In one aspect the mutant allele comprises an amino acid insertion, deletion or replacement in the ATP-binding domain of the NBD1 domain of a Cucurbitaceae Emb2 protein. The ATP-binding domain of the NBD1 domain of Cucurbitaceae Emb2 proteins comprises amino acids GGSGSGKS (e.g. amino acids 426 to 433 of SEQ ID NO: 6; amino acids 429 to 436 of SEQ ID NO: 4; amino acids 394 to 401 of SEQ ID NO: 5, or the equivalent amino acids of another Cucurbitaceae Emb2 protein, thus in one aspect one or more amino acids of amino acids are inserted, replaced or deleted in this domain.

In one aspect any Glycine (G) of the ATP-binding domain is replaced by a different amino acid.

In yet another aspect any Glycine and/or any Proline of the NBD1 domain is replaced by another amino acid. Glycine and Proline are commonly highly conserved in protein families, and their replacement will likely affect the secondary structure of the protein and thereby lead to a reduced function or loss of function.

A particular mutant allele comprises a replacement of amino acid Leucine (Leu) 478 of SEQ ID NO: 1 or 6, or of amino acid Leu481 of SEQ ID NO: 4, or of amino acid Leu446 of SEQ ID NO: 5 by another amino acid, or the equivalent amino acid in the NBD1 domain of another emb2 protein. For example the Leucine at that position is replaced by a Phenylalanine.

A particular mutant allele comprises a replacement of amino acid Alanine508 of SEQ ID NO: 1 or 6, or of amino acid Ala511 of SEQ ID NO: 4, or of amino acid Ala476 of SEQ ID NO: 5 by another amino acid, or the equivalent amino acid in the NBD1 domain of another emb2 protein. For example the Alanine at that position is replaced by a Threonine.

A particular mutant allele comprises a replacement of amino acid Threonine 521 of SEQ ID NO: 1 or 6, or of amino acid Threonine 524 of SEQ ID NO: 4, or of amino acid Threonine 489 of SEQ ID NO: 5 by another amino acid, or the equivalent amino acid in the NBD1 domain of another emb2 protein. For example the Threonine at that position is replaced by a Isoleucine.

Another mutant emb2 allele is a mutant allele of a Solanaceae emb2 allele (especially an allele of tomato or pepper) and comprises an amino acid insertion, deletion or replacement in the NBD1 domain, i.e. in one aspect in a Nucleotide Binding domain 1 (NBD1) of Solanaceae, i.e. in the amino acids starting at amino acid number 379 to (and including) amino acid number 617 of SEQ ID NO: 9, or in a NBD1 amino acid domain of another Emb2 protein (e.g. a protein comprising at least at least 70%, 75%, more preferably at least 80%, even further preferred at least 90%, or particularly preferred at least 95% with the amino acid sequence given under SEQ ID NO: 9 or SEQ ID NO:10 or SEQ ID NO:11), wherein said NBD1 domain comprises at least 95%, 96%, 97%, 98%, 99% or 100% sequence identity to NBD1 of SEQ ID NO: 9. For example one or more amino acids may be inserted, deleted or replaced in the NBD1 domain of SEQ ID NO: 9 (starting at amino acid 379 and ending at amino acid 617), or in the NBD1 domain of SEQ ID NO: 10 (starting at amino acid 376 and ending at amino acid 614), or in the NBD1 domain of SEQ ID NO: 11 (starting at amino acid 376 and ending at amino acid 614).

In one aspect the mutant allele comprising an amino acid insertion, deletion or replacement in the ATP-binding domain of the NBD1 domain of a Solanaceae Emb2 protein. The ATP-binding domain of the NBD1 domain of Solanaceae Emb2 proteins comprises amino acids GGSGSGKS (e.g. amino acids 414 to 421 of SEQ ID NO: 9; amino acids 411 to 418 of SEQ ID NO: 10; amino acids 411 to 418 of SEQ ID NO: 11, or the equivalent amino acids of another Solanaceae Emb2 protein, thus in one aspect one or more amino acids of amino acids are inserted, replaced or deleted in this domain.

In one aspect any Glycine (G) of the ATP-binding domain is replaced by a different amino acid.

In yet another aspect any Glycine and/or any Proline of the NBD1 domain is replaced by another amino acid. Glycine and Proline are commonly highly conserved in protein families, and their replacement will likely affect the secondary structure of the protein and thereby lead to a reduced function or loss of function.

A particular mutant allele comprises a replacement of amino acid Leucine (Leu) 466 of SEQ ID NO: 9, or of amino acid Leu463 of SEQ ID NO: 10, or of amino acid Leu463 of SEQ ID NO: 11 by another amino acid, or the equivalent amino acid in the NBD1 domain of another emb2 protein. For example the Leucine at that position is replaced by a Phenylalanine.

A particular mutant allele comprises a replacement of amino acid Alanine 596 of SEQ ID NO: 9, or of amino acid Ala493 of SEQ ID NO: 10, or of amino acid Ala493 of SEQ ID NO: 11 by another amino acid, or the equivalent amino acid in the NBD1 domain of another emb2 protein. For example the Alanine at that position is replaced by a Threonine.

A particular mutant allele comprises a replacement of amino acid Threonine 509 of SEQ ID NO: 9, or of amino acid Thr506 of SEQ ID NO: 10, or of amino acid Thr506 of SEQ ID NO: 11 by another amino acid, or the equivalent amino acid in the NBD1 domain of another emb2 protein. For example the Threonine at that position is replaced by a Isoleucine.

TMD2 Domain:

Another mutant emb2 allele is a mutant allele of a Cucurbitaceae emb2 allele (especially an allele of watermelon, melon or cucumber) and comprises an (at least one) amino acid insertion, deletion and/or replacement in the TMD2 domain, i.e. in one aspect in a Transmembrane Domain 2 (TMD2) of Cucurbitaceae, i.e. in the amino acids starting at amino acid number 709 to (and including) amino acid number 978 of SEQ ID NO: 1 or of SEQ ID NO: 6, or in a TMD2 amino acid domain of another Emb2 protein (e.g. a protein comprising at least at least 70%, 75% more preferably at least 80%, even further preferred at least 90%, or particularly preferred at least 95%, 96%, 97%, 98% or 99% with the amino acid sequence given under SEQ ID NO: 6 or SEQ ID NO: 4 or SEQ ID NO: 5), wherein said TMD2 domain comprises at least 95%, 96%, 97%, 98%, 99% or 100% sequence identity to TMD2 of SEQ ID NO: 1 or SEQ ID NO: 6. For example one or more amino acids may be inserted, deleted or replaced in the TMD2 domain of SEQ ID NO: 1 or SEQ ID NO: 6 (starting at amino acid 709 and ending at amino acid 978), or in the TMD2 domain of SEQ ID NO: 4 (starting at amino acid 712 and ending at amino acid 981), or in the TMD2 domain of SEQ ID NO: 5 (starting at amino acid 677 and ending at amino acid 946).

Another mutant emb2 allele is a mutant allele of a Solanaceae emb2 allele (especially an allele of tomato or pepper) and comprises an amino acid insertion, deletion or replacement in the TMD2 domain, i.e. in one aspect in a Transmembrane Domain 2 (TMD2) of Solanaceae, i.e. in the amino acids starting at amino acid number 698 to (and including) amino acid number 967 of SEQ ID NO: 9, or in a TMD2 amino acid domain of another Emb2 protein (e.g. a protein comprising at least at least 70%, 75% more preferably at least 80%, even further preferred at least 90%, or particularly preferred at least 95% with the amino acid sequence given under SEQ ID NO: 9 or SEQ ID NO:10 or SEQ ID NO:11), wherein said TMD2 domain comprises at least 95%, 96%, 97%, 98%, 99% or 100% sequence identity to TMD2 of SEQ ID NO: 9. For example one or more amino acids may be inserted, deleted or replaced in the TMD2 domain of SEQ ID NO: 9 (starting at amino acid 698 and ending at amino acid 967), or in the TMD2 domain of SEQ ID NO: 10 (starting at amino acid 692 and ending at amino acid 961), or in the TMD2 domain of SEQ ID NO: 11 (starting at amino acid 692 and ending at amino acid 961).

In a further embodiment any non-polar (comprising a hydrophobic side chain) amino acid of the TMD2 domain of the Solanaceae Emb2 proteins is replaced by a polar amino acid (comprising a hydrophilic side chain). Non-polar amino acids are Alanine (A or Ala), Cysteine (C or Cys), Glycine (G or Gly), Isoleucine (I or Ile), Leucine (L or Leu), Methionine (M or Met), Phenylalanine (F or Phe), Proline (P or Pro), Tryptophan (W or Trp), Valine (V or Val). Polar amino acids are Arginine (R or Arg), Asparagine (N or Asn), Aspartate (D or Asp), Glutamate (E or Glu), Glutamine (Q or Gln), Histidine (H or His), Lysine (K or Lys), Serine (S or Ser), Threonine (T or Thr), Tyrosine (Y or Tyr).

In yet another aspect any Glycine and/or or Proline of the TMD2 domain is replaced by another amino acid. Glycine and Proline are commonly highly conserved in protein families, and their replacement will likely affect the secondary structure of the protein and thereby lead to a reduced function or loss of function.

NBD2 Domain:

Another mutant emb2 allele is a mutant allele of a Cucurbitaceae emb2 allele (especially an allele of watermelon, melon or cucumber) and comprises an (at least one) amino acid insertion, deletion and/or replacement in the NBD2 domain, i.e. in one aspect in a Nucleotide Binding Domain 2 (NBD2) of Cucurbitaceae, i.e. in the amino acids starting at amino acid number 1025 to (and including) amino acid number 1260 of SEQ ID NO: 1 or of SEQ ID NO: 6, or in a NBD2 amino acid domain of another Emb2 protein (e.g. a protein comprising at least at least 70%, 75%, more preferably at least 80%, even further preferred at least 90%, or particularly preferred at least 95%, 96%, 97%, 98% or 99% with the amino acid sequence given under SEQ ID NO: 6 or SEQ ID NO:4 or SEQ ID NO:5), wherein said NBD2 domain comprises at least 95%, 96%, 97%, 98%, 99% or 100% sequence identity to NBD2 of SEQ ID NO: 1 or SEQ ID NO: 6. For example one or more amino acids may be inserted, deleted or replaced in the NBD2 domain of SEQ ID NO: 1 or SEQ ID NO: 6 (starting at amino acid 1025 and ending at amino acid 1260), or in the NBD2 domain of SEQ ID NO: 4 (starting at amino acid 1028 and ending at amino acid 1263), or in the NBD2 domain of SEQ ID NO: 5 (starting at amino acid 993 and ending at amino acid 1228).

In one aspect the mutant allele comprising an amino acid insertion, deletion or replacement in the ATP-binding domain of the NBD2 domain of a Cucurbitaceae Emb2 protein. The ATP-binding domain of the NBD2 domain of Cucurbitaceae Emb2 proteins comprises amino acids GQSGSGKS (e.g. amino acids 1060 to 1066 of SEQ ID NO: 6; amino acids 1063 to 1070 of SEQ ID NO: 4; amino acids 1028 to 1035 of SEQ ID NO: 5, or the equivalent amino acids of another Cucurbitaceae Emb2 protein), thus in one aspect one or more amino acids of amino acids are inserted, replaced or deleted in this domain.

In one aspect any Glycine (G) of the ATP-binding domain is replaced by a different amino acid.

In yet another aspect any Glycine and/or any Proline of the NBD2 domain is replaced by another amino acid. Glycine and Proline are commonly highly conserved in protein families, and their replacement will likely affect the secondary structure of the protein and thereby lead to a reduced function or loss of function.

Another mutant emb2 allele is a mutant allele of a Solanaceae emb2 allele (especially an allele of tomato or pepper) and comprises an amino acid insertion, deletion or replacement in the NBD2 domain, i.e. in one aspect in a Nucleotide Binding Domain 2 (NBD2) of Solanaceae, i.e. in the amino acids starting at amino acid number 1014 to (and including) amino acid number 1249 of SEQ ID NO: 9, or in a NBD2 amino acid domain of another Emb2 protein (e.g. a protein comprising at least at least 70%, 75%, more preferably at least 80%, even further preferred at least 90%, or particularly preferred at least 95% with the amino acid sequence given under SEQ ID NO: 9 or SEQ ID NO:10 or SEQ ID NO:11), wherein said NBD2 domain comprises at least 95%, 96%, 97%, 98%, 99% or 100% sequence identity to NBD2 of SEQ ID NO: 9. For example one or more amino acids may be inserted, deleted or replaced in the NBD2 domain of SEQ ID NO: 9 (starting at amino acid 1014 and ending at amino acid 1249), or in the NBD2 domain of SEQ ID NO: 10 (starting at amino acid 1008 and ending at amino acid 1243), or in the NBD2 domain of SEQ ID NO: 11 (starting at amino acid 1008 and ending at amino acid 1243).

In one aspect the mutant allele comprising an amino acid insertion, deletion or replacement in the ATP-binding domain of the NBD2 domain of a Solanaceae Emb2 protein.

The ATP-binding domain of the NBD2 domain of Solanaceae Emb2 proteins comprises amino acids GQSGSGKS (e.g. amino acids 1049 to 1056 of SEQ ID NO: 9; amino acids 1043 to 1050 of SEQ ID NO: 10; amino acids 1043 to 1050 of SEQ ID NO: 11, or the equivalent amino acids of another Solanaceae Emb2 protein, thus in one aspect one or more amino acids of amino acids are inserted, replaced or deleted in this domain.

In one aspect any Glycine (G) of the ATP-binding domain is replaced by a different amino acid.

In yet another aspect any Glycine and/or any Proline of the NBD2 domain is replaced by another amino acid. Glycine and Proline are commonly highly conserved in protein families, and their replacement will likely affect the secondary structure of the protein and thereby lead to a reduced function or loss of function.

In another aspect the mutant allele results in a truncated Emb2 protein being produced, which truncated protein has decreased function or loss-of-function. A truncation may for example result in the loss of the C-terminal end (carboxyl terminal end) of the protein, whereby part or all of the NBD2 domain is absent. Optionally the truncation may be larger, so that not only the NBD2 domain is absent, but also part or all of the TMD2 domain, or even more amino acids may be missing. For example only the N-terminal part (amino terminal part) of the protein may still be present. Mutant alleles which express a truncated Emb2 protein can be induced whereby, for example, a codon in one of the exons is changed into a premature stop codon or splice-site mutations can also lead to premature stop codons and truncated proteins.

Plants in which the mutant allele of a Emb2 protein-encoding gene is present in a heterozygous state, will produce seeds and are male fertile. Thus, those plants can be used to introduce the mutant emb2 allele into other plants or they can be used to introduce further traits into the plant in which the mutant emb2 allele is present. These plants can also be used to propagate plants comprising a mutant allele.

50% of the self-pollinated offspring in each case will still carry the mutant allele in a heterozygous state. Therefore, plants in which the mutant allele is present are useful e.g. in breeding.

The mutant emb2 allele is designated as "emb2", while the wild type, functional Emb2 allele is designated as "Emb2" herein.

In addition, crossing a heterozygous plant (emb2/Emb2), e.g. as female parent, with a homozygous mutant plant (emb2/emb2), e.g. as male parent, results in 50% of seeds being homozygous for the recessive emb2 allele (genotype emb2/emb2) and 50% of seeds being heterozygous, i.e. comprise one mutant emb2 allele and one wild type allele (genotype emb2/Emb2). Only the homozygous mutant seeds will grow into plants which produce seedless fruits after pollination (e.g. self-pollination). As the semi-glabrous trait is linked to, or is an effect of, the mutant emb2 allele, at least in watermelon e.g. at least in the EMB2 plants deposited, the seedling mix can be grown and the 50% of seedlings which are homozygous for the mutant emb2 allele can be simply selected by selecting the seedlings which have less hairs on the stems, i.e. which comprise the semi-glabrous trait as shown in FIG. 2A. This method of propagating and/or selecting plants comprising the emb2 allele in homozygous form (emb2/emb2), and the use of such selected seedlings and plants to produce seedless watermelon fruits (by e.g. transplanting only the homozygous mutant seedlings into the watermelon production field) is also an aspect of the invention. In one aspect selection of seedlings is based on the semi-glabrous phenotype, but in another aspect selection of plants, seeds or seedlings is based on methods which can determine the plant or plant cell genotype, i.e. the presence of one or two copies of a mutant emb2 allele.

Therefore, one embodiment of the invention concerns plant cells or plants according to the invention which are heterozygous for a mutant emb2 allele (ABCB transporter encoding gene).

In a preferred embodiment of the invention, the decreased activity of a ABCB transporter protein (Emb2 protein) in plant cells or plants according to the invention is due to, or caused by, or is the effect of a mutant allele of a ABCB transporter protein-encoding gene (Emb2 protein-encoding gene) being present in plant cells or plants, respectively.

In one aspect, the plant cells or plants according to the invention are homozygous for the mutant emb2 allele of a Emb2 protein-encoding gene, encoding a decrease of function of a Emb2 protein or a loss of function of a Emb2 protein. Plants according to the invention being homozygous for a mutant allele of a Emb2-protein encoding gene (diploid genotype emb2/emb2) produce seedless fruits upon pollination with own pollen or pollen obtained from a different plant.

Another embodiment of the invention, therefore, concerns plant cells or plants according to the invention which are homozygous for a mutant allele of a Emb2 protein-encoding gene.

A mutant allele of a Emb2 protein-encoding gene causes a plant to be male fertile but producing seedless fruits, when the plant is homozygous for the mutant emb2 allele. Concerning the embodiments of the invention, the mutation in the mutant allele of a Emb2 protein-encoding gene (i.e. in the mutant emb2 allele) can be any mutation, including one or more deletions, truncations, insertions, point mutations, nonsense mutations, missense or non-synonymous mutations, splice-site mutations, frame shift mutations and/or mutations in regulatory sequences (for example in the promoter sequence). In one aspect the mutation in the mutant emb2 allele is a point mutation. The mutation can occur in a DNA sequence comprising the coding sequence of a Emb2 protein-encoding gene or in a RNA sequence encoding a Emb2 protein or it can occur in the amino acid molecule of Emb2 protein. Concerning a DNA sequence of Emb2 protein-encoding gene the mutation can occur in the coding sequence (cds, composed of the exons) or it can occur in non-coding sequences like 5'- and 3'-untranslated regions, introns, promoters, enhancers etc. of a Emb2 protein-encoding gene. In respect to RNA encoding a Emb2 protein the mutation can occur in the pre-mRNA or the mRNA. In one aspect the mutant allele results in the protein having a loss-of-function or decrease of function due to one or more amino acids being replaced, inserted and/or deleted, for example resulting in one or more amino acids being replaced, inserted or deleted in the conserved TMD1, NBD1, TMD2 and/or NBD2 domain, and/or optionally in the linker domain. For example, truncation of the protein to cause deletion of one or more or all conserved domains, or part thereof, will result in a loss of function or decrease of function of the protein.

A further embodiment of the invention therefore concerns plant cells or plants according to the invention comprising a mutant allele of a Emb2 protein-encoding gene characterized in that the mutant emb2 allele comprises or effects one or more of the mutations selected from the group consisting of a) a deletion, truncation, insertion, point mutation, nonsense mutation, missense or non-synonymous mutation, splice-site mutation, frame shift mutation in the genomic sequence; b) a mutation in one or more regulatory sequences;

c) a deletion, truncation, insertion, point mutation, nonsense mutation, missense or non-synonymous mutation, splice-site mutation, frame shift mutation in the coding sequence;

d) a deletion, truncation, insertion, point mutation, nonsense mutation, missense or non-synonymous mutation, splice-site mutation, frame shift mutation in the pre-mRNA or mRNA; and/or e) a deletion, truncation, insertion or replacement of one or more amino acids in the Emb2 protein.

In the mutant watermelon plant (EMB2 plant, and mutant allele is in the deposited seeds) created by the inventors through chemical mutagenesis, the genomic DNA has a point mutation (replacement of a G by an A) at nucleotide position 3331 of SEQ ID NO: 8 (wild type genomic DNA). The genomic DNA comprising this point mutation is depicted in SEQ ID NO: 3. The mRNA transcribed from this mutant emb2 allele of SEQ ID NO: 3 is shown under SEQ ID NO: 2, depicted as cDNA instead of mRNA. The mRNA/cDNA of SEQ ID NO: 2 comprises the point mutation (replacement of G by an A) at nucleotide position 604. The point mutation results in a change of the codon 'GGG' (codon for Glycine) into the codon 'AGG' (codon for Arginine). Thereby the mutant watermelon emb2 protein comprises a single amino acid substitution, i.e. the Glycine at amino acid 202 of SEQ ID NO: 6 (wild type Emb2 protein) is replaced in the mutant emb2 protein by an Arginine at amino acid 202, as depicted in SEQ ID NO: 1 (mutant emb2 protein).

The stenospermocarpy phenotype of the EMB2 plant is, therefore, caused by the presence of two copies of the mutant emb2 allele. As mentioned, the amino acid substitution in the EMB2 plant is in a highly conserved domain of the ABCB transporter protein, namely in one of the alpha helices of the TMD1 domain. Glycine is the smallest amino acid and rotates easily, adding flexibility to a protein. Glycine is frequently found in highly conserved domains of proteins. Replacing Glycine202 in the alpha helix of the TMD1 domain by an Arginine, which has a long, positively charged side chain and is a polar, results in change in the secondary structure of the alpha helix and in a reduced function or even loss of function of the protein.

Thus, specifically disclosed herein for exemplifying the application is in one aspect a nucleic acid sequence of a mutant emb2 allele comprising a point mutation (nucleotide replacement) compared to the nucleic acid sequence of the corresponding wild type Emb2 allele. The point mutation in the mutant emb2 allele results in an amino acid substation in a highly conserved domain of the Emb2 protein, rendering the Emb2 protein non-functional or having a reduced function.

In one aspect of the invention the mutant emb2 allele of a Emb2 protein encoding gene has a mutation leading to one or more or all of the amino acids encoding the TMD1, NBD1, TMD2 or NBD2 domain being deleted or being replaced by different amino acids than in the wild type. In one aspect the mutant allele results in a truncated protein lacking all or part of the wild type protein, especially one or more of the conserved domains TMD1, NBD1, TMD2 or NBD2. For example, the mutant allele contains a mutation leading to a premature stop codon, whereby all or part of the conserved domains are not present anymore in the resulting protein.

In one aspect the mutant allele is a mutant allele watermelon emb2 gene of SEQ ID NO: 3 (genomic DNA of the mutant emb2 allele, as present in the EMB2 plant) and leads to the protein of SEQ ID NO: 1 (mutant emb2 protein). This particular mutant allele is present in seeds deposited by Nunhems B.V. on 31 May 2018 under accession number NCIMB 43064.

In watermelon seed coat color is controlled by three genes, r, t and w (see Gunnar and Wehner 2004, HortScience39(6)1175-1182) producing 6 phenotypes of seed coat color. Black (RR TT WW), clump (RR TT ww), tan (RR tt WW), white (RR tt ww) or (rr tt ww) and red (rr tt WW). Thus in one aspect the mutant emb2 allele as described herein is combined in a watermelon plant in homozygous form with the genes for white seed coat color in homozygous form, thus either RR tt ww or rr tt ww. In one aspect the seeds produced in the seed defective fruits of a watermelon plant as described herein have a white seed coat. Thus in one aspect the watermelon plant is homozygous for the mutant emb2 allele and any seeds that may be produced in the seedless/seed-defective fruits on the plant have a white seed coat. Thus in diploid watermelons the mutant emb2 allele is combined with the genotype RR tt ww or rr tt ww for seed coat color. Likewise tetraploids and triploid watermelons comprising four or three copies of the mutant emb2 allele are encompassed herein, optionally in combination with the tetraploids comprising four copies, and the triploids comprising three copies, of the genes determining white seed coat color. Thus both diploid seedless/seed-defective fruits comprising small seeds with white seed coat and triploid seedless/seed-defective fruits comprising small seeds with white seed coat are provided.

It was found that the Emb2 protein is a ABCB transporter protein which comprises a highly conserved primary structure in Cucurbitaceae (e.g. watermelon, cucumber and melon) and Solanaceae (e.g. tomato and pepper), as the watermelon, cucumber and melon Emb2 proteins have a high percentage of sequence identity to each other, and the tomato and pepper Emb2 proteins also have a high percentage of amino acid sequence identity.

Thus, in one aspect a Cucurbitaceae (e.g. a watermelon, melon or cucumber) plant, plant part or cell comprising in its genome at least one copy of a mutant allele of an Emb2 gene is provided, wherein the Emb2 gene is a gene which encodes a protein comprising at least 70%, 75%, 78%, 80%, 90%, 94%, 95%, 96%, 97%, 98%, or more, sequence identity with the protein of SEQ ID NO: 6, SEQ ID NO: 4 or SEQ ID NO: 5, wherein the mutant allele causes stenospermocarpic fruit formation when the mutant allele is present in homozygous form. In one aspect the mutant allele of the Emb2 gene comprises a mutation which results in reduced expression or no expression of the wild type Emb2 gene. In another aspect the mutant allele of the Emb2 gene comprises a mutation which results in the expression of a mutant emb2 protein having reduced function or no function, compared to the wild type (functional) Emb2 protein.

In one aspect a Solanaceae (e.g. a tomato or pepper) plant, plant part or cell, or a plant, plant part or cell comprising in its genome at least one copy of a mutant allele of an Emb2 gene is provided, wherein the Emb2 gene is a gene which encodes a protein comprising at least 70%, 75%, 78%, 80%, 90%, 92%, 95%, 96%, 97%, 98%, or more, sequence identity with the protein of SEQ ID NO: 9, SEQ ID NO: 10 or SEQ ID NO: 11, wherein the mutant allele causes stenospermocarpic fruit formation when the mutant allele is present in homozygous form. In one aspect the mutant allele of the Emb2 gene comprises a mutation which results in reduced expression or no expression of the wild type Emb2 gene. In another aspect the mutant allele of the Emb2 gene comprises a mutation which results in the expression of a mutant emb2 protein having reduced function or no function, compared to the wild type (functional) Emb2 protein.

As described further above, also truncations wherein one or more of the conserved domains (or a part thereof) are absent compared to the wild type protein are a particular aspect of the invention. Likewise, mutant alleles resulting in one or more amino acids being replaced, deleted or inserted, especially in one or more of the conserved domains, are a preferred embodiment. Especially a replacement, insertion or deletion in the TMD1 domain, e.g. in the alpha helix region of the TMD1 domain.

A different embodiment of the invention concerns plant cells, plant parts or plants comprising or synthesising an mRNA encoding a Emb2 protein, wherein the mRNA encoding a Emb2 protein has one or more mutations selected from the group consisting of
 a) a deletion mutation
 b) a missense or non-synonymous mutation;
 c) a frame shift mutation; and/or
 d) a non-sense mutation.

In a preferred embodiment of the invention, plant cells, plant parts or plants according to the invention comprise or synthesise an mRNA encoding a Emb2 protein having one or more of the mutations selected from the group consisting of
 a) a deletion mutation
 b) a missense or non-synonymous mutation;
 c) a frame shift mutation; and/or
 d) a non-sense mutation.

In another embodiment of the invention, plant cells or plants according to the invention comprise or synthesise an mRNA encoding a Emb2 protein having one or more mutations, wherein the mRNA is transcribed from a mutant allele of a Emb2 protein-encoding gene. Comprised by these embodiments of the invention are plant cells, plant parts or plants according to the invention comprising or synthesising an mRNA transcribed from a mutant allele of a Emb2 protein-encoding gene, characterized in that the mRNA comprises a deletion mutation and/or a missense or non-synonymous mutation and/or a frame shift mutation and/or a non-sense mutation, compared to the corresponding (DNA) coding sequence of the mutant allele of the Emb2 protein-encoding gene from which the mRNA is transcribed. Thus, in one aspect any mutation which affects pre-mRNA splicing is encompassed, i.e. which modifies the normal pre-mRNA splicing process, thereby leading to a different mRNA molecule.

An "mRNA coding sequence" shall have the common meaning herein. An mRNA coding sequence corresponds to the respective DNA coding sequence of a gene/allele apart from that thymine (T) is replaced by uracil (U).

For any of the above described mutations or combinations of mutations, it is understood that they result in causing a decrease of function or a loss of function in activity of Emb2 protein in plant cells, plant parts or plants according to the invention.

Another embodiment of the invention concerns plant cells, plant parts or plants, comprising or synthesising a Emb2 protein, characterized in that the amino acid sequence of the Emb2 protein comprises a mutation compared to the corresponding wild type Emb2 protein. The mutation in the Emb2 protein causes a decrease or loss of function in activity of a Emb2 protein in plant cells, plant parts or plants according to the invention.

The mutation in the Emb2 protein can be an amino acid replacement, insertion, deletion and/or truncation compared to the amino acid sequence of a wild type Emb2 protein. In one embodiment of the invention the amino acid sequence of the Emb2 protein comprises a deletion or truncation, more preferred a truncation at the N-terminus and/or C-terminus, even more preferred a truncation at the C-terminus. Preferably at least 25, preferably at least 30, 40, 50, 60, 70, 80, 90 or 100, more preferably at least 150 and even more preferred at least 200, 250, 300 or 320 amino acids are missing from the N-terminal end or C-terminal end of the amino acid sequence compared to the corresponding wild type Emb2 protein.

Further provided are Cucurbitaceae plant cells, plant parts or plants according to the invention (e.g. watermelon, melon or cucumber) comprising or synthesising a reduced function or non-functional Emb2 protein (compared to the endogenous functional Emb2 protein), or comprises a knock-down or knock-out of the gene expression of the gene (at least one allele of the gene) encoding the endogenous wild type Emb2 protein, whereby the wild type Emb2 protein has at least 70%, 75%, more preferably at least 80%, even further preferred at least 90% or particularly preferred at least 95%, 96%, 97%, 98% sequence identity with the amino acid sequence shown under SEQ ID NO: 6 (a watermelon functional Emb2 protein), or with the amino acid sequence shown under SEQ ID NO: 4 (a cucumber functional Emb2 protein) or with the amino acid sequence shown under SEQ ID NO: 5 (a melon functional Emb2 protein). As mentioned further above, the reduced function or loss of function of the endogenous Emb2 protein may be due to one or more amino acids being inserted, deleted and/or replaced in the mutant protein compared to the wild type protein. Especially one or more amino acids being inserted, deleted and/or replaced in at least one of the conserved domains (TMD1, NBD1, TMD2, NBD2, or conserved subdomains of any of these) is encompassed herein.

Likewise provided are Solanaceae plant cells, plant parts or plants according to the invention (e.g. tomato or pepper) comprising or synthesising a reduced function or non-functional Emb2 protein (compared to the endogenous functional Emb2 protein), or comprises a knock-down or knock-out of the gene expression of the gene (at least one allele of the gene) encoding the endogenous wild type Emb2 protein, whereby the wild type Emb2 protein has at least 70%, 75%, more preferably at least 80%, even further preferred at least 90% or particularly preferred at least 95%, 96%, 97%, 98% sequence identity with the amino acid sequence shown under SEQ ID NO: 9 (a tomato functional Emb2 protein), or with the amino acid sequence shown under SEQ ID NO: 10 (a *Capsicum* functional Emb2 protein) or with the amino acid sequence shown under SEQ ID NO: 11 (a *Capsicum* functional Emb2 protein). As mentioned further above, the reduced function or loss of function of the endogenous Emb2 protein may be due to one or more amino acids being inserted, deleted and/or replaced in the mutant protein compared to the wild type protein. Especially one or more amino acids being inserted, deleted and/or replaced in at least one of the conserved domains (TMD1, NBD1, TMD2, NBD2, or conserved subdomains of any of these) is encompassed herein.

A further embodiment of the invention therefore concerns plant cells or plants selected from the family Cucurbitaceae, especially from the species watermelon, melon and cucumber, or from the family Solanaceae, especially from the species tomato and pepper, comprising a mutant allele of a Emb2 protein-encoding gene characterized in that the mutant allele comprises or effects one or more of the mutations selected from the group consisting of a) a deletion, truncation, insertion, point mutation, nonsense mutation, missense or non-synonymous mutation, splice-site mutation, frame shift mutation in the genomic sequence;

b) a mutation in one or more regulatory sequences;

c) a deletion, truncation, insertion, point mutation, nonsense mutation, missense or non-synonymous mutation, splice-site mutation, frame shift mutation in the coding sequence;

d) a deletion, truncation, insertion, point mutation, nonsense mutation, missense or non-synonymous mutation, splice-site mutation, frame shift mutation in the pre-mRNA or mRNA; and/or e) a deletion, truncation, insertion or replacement of one or more amino acids in the Emb2 protein.

The above mutant allele results in decreased activity of the mutant Emb2 protein compared to the wild type Emb2 protein. The decreased activity is due to a knock-out of expression of the Emb2 gene, a knock-down of expression of the gene, a loss of function of the encoded mutant Emb2 protein or a decrease of function of the mutant Emb2 protein.

In one aspect, wherein the plant cell or plant is watermelon, the mutant allele of the Emb2 protein is a mutant allele of the allele encoding the protein of SEQ ID NO: 6 or a protein comprising substantial sequence identity to SEQ ID NO: 6, preferably at least 70%, 75%, 80%, 90%, 91%, 92%, 93%, 94%, 95%, 96%, 97%, 98% sequence identity when the two full length sequences of the functional Emb2 protein are pairwise aligned (e.g. using the Emboss program Needle with default parameters).

In another aspect, wherein the plant cell or plant is melon, the mutant allele of the Emb2 protein is a mutant allele of the allele encoding the protein of SEQ ID NO: 5 or a protein comprising substantial sequence identity to SEQ ID NO: 5, preferably at least 70%, 80%, 90%, 91%, 92%, 93%, 94%, 95%, 96%, 97%, 98% sequence identity when the two full length sequences of the functional Emb2 protein are pairwise aligned (e.g. using the Emboss program Needle with default parameters).

In another aspect, wherein the plant cell or plant is cucumber, the mutant allele of the Emb2 protein is a mutant allele of the allele encoding the protein of SEQ ID NO: 4 or a protein comprising substantial sequence identity to SEQ ID NO: 4, preferably at least 70%, 80%, 90%, 91%, 92%, 93%, 94%, 95%, 96%, 97%, 98% sequence identity when the two full length sequences of the functional Emb2 protein are pairwise aligned (e.g. using the Emboss program Needle with default parameters).

In another aspect, wherein the plant cell or plant is tomato, the mutant allele of the Emb2 protein is a mutant allele of the allele encoding the protein of SEQ ID NO: 9 or a protein comprising substantial sequence identity to SEQ ID NO: 9, preferably at least 70%, 80%, 90%, 91%, 92%, 93%, 94%, 95%, 96%, 97%, 98% sequence identity when the two full length sequences of the functional Emb2 protein are pairwise aligned (e.g. using the Emboss program Needle with default parameters).

In another aspect, wherein the plant cell or plant is pepper, the mutant allele of the Emb2 protein is a mutant allele of the allele encoding the protein of SEQ ID NO: 10 or 11, or a protein comprising substantial sequence identity to SEQ ID NO: 10 or 11, preferably at least 70%, 80%, 90%, 91%, 92%, 93%, 94%, 95%, 96%, 97%, 98% sequence identity when the two full length sequences of the functional Emb2 protein are pairwise aligned (e.g. using the Emboss program Needle with default parameters).

In one aspect the Cucurbitaceae (e.g. watermelon, melon, cucumber) or Solanaceae (e.g. tomato or pepper) plant comprises the mutant Emb2 allele in heterozygous form. In another aspect the Cucurbitaceae (e.g. watermelon, melon, cucumber) or Solanaceae (e.g. tomato or pepper) plant comprises the mutant Emb2 allele in homozygous form, whereby the plant produces seedless fruits upon pollination with own or other pollen. In one aspect the mutant emb2 allele is a knock-out (i.e. the gene is not expressed) or the allele encodes a non-function Emb2 protein.

Seeds from which such plants can be grown are encompassed herein as well as the seedless fruits produced from said plants when the allele is in homozygous form or the seeded fruits produced from said plants when the allele is in heterozygous form. Also any plant parts, such as cuttings, vegetative propagations, cells, etc. comprising at least one mutant emb2 allele in their genome are provided. The seedless fruits may thus be e.g. seedless watermelon fruits, seedless melon fruits, seedless cucumber fruits, seedless tomato fruits, seedless pepper fruits (e.g. paprika or hot peppers), etc. The cells of the seedless fruits also comprise the mutant emb2 allele and can thus be distinguished from any other seedless fruits.

In one aspect also seedlings are encompassed comprising the mutant Emb2 allele in homozygous form, whereby the seedlings are distinguishable from seedlings comprising the mutant emb2 allele in heterozygous form and/or wild type (homozygous for the functional Emb2 allele) through e.g. the amount of hairs on the stem of the seedlings, i.e. the homozygous mutant comprises in one embodiment fewer hairs than the heterozygous and/or wild type (homozygous for the functional Emb2 allele) seedling, also referred to as semi-glabrous phenotype. The seedlings may be any Cucurbitaceae (e.g. watermelon, melon, cucumber) or Solanaceae (e.g. tomato or pepper) seedlings, as described. In one aspect the seedlings are watermelon seedlings. In one aspect the watermelon seedlings are seedlings comprising the mutant allele encoding the protein of SEQ ID NO: 1. It is not known yet if the semi-glabrous phenotype is associated with any mutant emb2 allele in any crop or is only associated with specific mutant alleles in specific crops, or is only associated with any mutant emb2 allele in watermelon, or is associated only with the specific mutant allele of the watermelon EMB1 plant (deposited). Still, the person skilled in the art will see, when generating a mutant emb2 allele in a crop plant, whether the allele results in/is associated with the semi-glabrous phenotype when the allele is in homozygous form. If this is the case, the skilled person can use the semi-glabrous phenotype in selection of homozygous mutant seedlings.

Also propagating and non-propagating cells comprising at least one copy of a mutant Emb2 allele are provided herein. It is understood that such propagating or non-propagating cells can be part of a plant organ or of an entire plant, or they can be isolated, e.g. in a cell culture or tissue culture.

In one aspect, the term plant part refers to plant cells, or plant tissues or plant organs that comprise one or more of the mutant alleles of the invention. In one aspect a plant part can grow into a plant and/or live on photosynthesis (i.e. synthesizing carbohydrate and protein from the inorganic substance, such as water, carbon dioxide and mineral salt). In another aspect, a plant part cannot grow into a plant and/or live on photosynthesis (i.e. synthesizing carbohydrate and protein from the inorganic substance, such as water, carbon dioxide and mineral salt). Thus, a plant part can be propagating or non-propagating.

The seed, plants and plant parts provided herein, comprising at least one mutant Emb2 allele in their genome, are preferably agronomically useful plants, e.g. inbred lines, breeding lines, varieties or cultivars or F1 hybrids. Preferably they having good agronomic characteristics, especially producing marketable fruits of good fruit quality and fruit uniformity.

As used herein, the term "variety" or "cultivar" means a plant grouping within a single botanical taxon of the lowest known rank, which can be defined by the expression of the characteristics resulting from a given genotype or combination of genotypes.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The watermelon Emb2 allele is located on chromosome 9 (between nucleotide 11940744 and 11949383) of the genome. The chromosome location can be determined by carrying out a BLAST® with e.g. the genomic sequence of SEQ ID NO: 3 (mutant genomic emb2 sequence) or SEQ ID NO: 8 (wild type genomic Emb2 sequence) against the whole genome, e.g. on world wide web at cucurbitgenomics.org against the "Watermelon (Charelston Grey) Genome". The point mutation present in the EMB2 plant (and in the seed deposit of NCIMB43064) is found at position 11944074 of the genome chromosome 9, corresponding to nucleotide 3331 of SEQ ID NO: 3 and SEQ ID NO: 8.

For watermelon, a mutant allele of a Emb2 protein-encoding gene present in the EMB2 plant (mutant genomic sequence of SEQ ID NO: 3, encoding the mutant Emb2 protein of SEQ ID NO: 1) can be obtained from the watermelon seeds being heterozygous or homozygous for the mutant allele of the Emb2 protein-encoding gene, deposited under NCIMB 43064. A wild type allele of a Emb2 protein-encoding gene can be obtained from the watermelon seeds being heterozygous or homozygous for the wild type Emb2 protein encoding gene, deposited under NCIMB 43064. The seeds homozygous for the mutant emb2 allele can be identified easily, as the seedlings will have the semi-glabrous phenotype. Other mutant alleles of a Emb2 protein-encoding gene can be generated de novo, e.g. by mutagenesis or by other methods known to the skilled person. This applies for any plant species. For example gene targeted modification methods, such as Crispr-Cas methods can be used to generate mutations in an endogenous Emb2 allele in a plant. Likewise, TILLING can be used to identify mutants in an endogenous Emb2 allele.

Plant cells, plant parts or plants or progeny thereof obtainable/obtained from seeds being heterozygous or homozygous for an allele of a Emb2 protein-encoding gene, deposited under NCIMB 43064 are also an embodiment of the invention, as is the mutant allele obtained from/obtainable from the deposited seeds. In one embodiment the plant cells, plant parts or plants or progeny thereof obtained from seeds deposited under NCIMB 43064 are homozygous for a mutant allele of a Emb2 protein-encoding gene. In one aspect of the invention a watermelon plant or plant part or plant cell is provided which comprises one or two copies of mutant emb2 allele as present in the deposited seeds. It may be that the semi-glabrous phenotype seen for seedlings of the deposit comprising the mutant allele in homozygous form, can be removed/dissociated from the mutant emb2 allele, e.g. when the allele is crossed into other watermelon plants.

It is understood that the invention encompasses the mutant emb2 allele as present in the deposited seeds (and also any other mutant emb2 allele described herein) also in the absence of any semi-glabrous phenotype.

A further comprised embodiment of the invention concerns plant cells, plant parts or plants, homozygous for a mutant allele of a Emb2 protein-encoding gene obtained/obtainable e.g. after crossing and/or selfing a watermelon plant obtained from seeds of deposit accession number NCIMB 43064 with another watermelon plant. Optionally the plants obtained/obtainable after crossing a plant obtained from seeds of deposit accession number NCIMB 43064 with another plant are subsequently self-pollinated. Optionally progeny seeds or plants are selected which are homozygous for a mutant allele of the mutant emb2 allele encoding gene as derived from/present in seeds deposited under accession number NCIMB 43064. Because the mutant emb2 allele present in the deposited seeds NCIMB 43064 results in a semi-glabrous phenotype of plants comprising the allele in homozygous form, this semi-glabrous phenotype can, in one aspect, be used to select progeny plants comprising two copies of the mutant emb2 allele. This may also be the case for other mutant emb2 alleles in watermelon, and optionally in other Cucurbitaceae species and optionally also in Solanaceae species, e.g. generated de novo. Obviously, seeds or plants comprising a mutant emb2 allele in homozygous form can also be selected or identified by other methods, as will be described, e.g. by genotyping, sequencing, etc.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

"Wild type allele" or "wild type Emb2 allele" refers herein to a version of a gene encoding a fully functional protein (wild type protein). A sequence of a gene encoding a fully functional Emb2 protein is, for example, the coding sequence of the wild type Emb2 protein sequences shown under SEQ ID NO: 7 (from cultivated watermelon), encoding the functional (wild type) protein of SEQ ID NO: 6. Other wild type Emb2 proteins are shown under SEQ ID NO: 4 (cucumber), SEQ ID NO: 5 (melon), SEQ ID NO: 9 (tomato) and SEQ ID NO: 10 and 11 (pepper). Other Emb2 protein-encoding nucleic acid sequences encoding fully functional Emb2 protein alleles (i.e. variant alleles, or allelic variants) may exist in these species and in other species, e.g. in other Cucurbitaceae and Solanaceae species. Such functional variants in Cucurbitacae species comprise substantial sequence identity to the Emb2 alleles encoding the Emb2 protein of SEQ ID NO: 6 and encode a functional Emb2 protein comprising at least 70%, 75%, 78%, 80%, 90%, 92%, 94%, 95%, 96%, 97%, 98% or 99% sequence identity to the Emb2 protein of SEQ ID NO: 6; and such functional variants in Solanaceae species comprise substantial sequence identity to the Emb2 alleles encoding the Emb2 protein of SEQ ID NO: 9 and encode a functional Emb2 protein comprising at least 70%, 75%, 78%, 80%, 90%, 92%, 94%, 95%, 96%, 97%, 98% or 99% sequence identity to the Emb2 protein of SEQ ID NO: 9.

A "mutant allele", e.g. "mutant emb2 allele", is to be understood in connection with the present invention to mean an allele which has a mutation compared to the corresponding wild type allele.

An example of a mRNA (depicted as cDNA) transcribed from a mutant emb2 allele is shown under SEQ ID NO: 2. The corresponding amino acid sequence encoded by the mRNA shown under SEQ ID NO: 2 is shown under SEQ ID NO: 1.

The term "locus" (loci plural) means a specific place or places or a site on a chromosome where for example a gene or genetic marker is found.

A "mutation" in a nucleic acid molecule (DNA or RNA) is a change of one or more nucleotides compared to the corresponding wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A "nucleic acid molecule" shall have the common understanding in the art. It is composed of nucleotides comprising either of the sugars deoxyribose (DNA) or ribose (RNA).

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a pre-mature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid at either the N-terminus or the C-terminus of the protein is missing compared to the amino acid sequence of the corresponding wild type protein, whereby in a 3'-end or C-terminal truncation at least the first nucleotide at the 5'-end or the first amino acid at the N-terminus, respectively, is still present and in a 5'-end or N-terminal truncation at least the last nucleotide at the 3'-end or the last amino acid at the C-terminus, respectively, is still present. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made.

"Homozygous" is referred herein to mean that all copies of a given gene or allele at a corresponding chromosomal locus in a cell or an organism are identical. "Homozygous for a mutant allele" means that all copies of the respective mutant allele at the corresponding chromosomal locus in a cell or an organism are identical.

"Heterozygous" is referred herein to mean that at least one copy of a given gene or allele at a specific chromosomal locus in a cell or an organism is different from the other copies of the gene(s) or allele(s) at the corresponding locus/loci in the other chromosome(s). "Heterozygous for a mutant allele" means that at least one allele at a specific chromosomal locus in a cell or an organism has a different sequence than the allele(s) at the corresponding locus/loci in the other chromosome(s).

A "mutation in a protein" or "mutant protein" is a change of one or more amino acid residues compared to the wild type amino acid sequence, e.g. by replacement, deletion, truncation or insertion of one or more amino acid residues.

Biotechnological methods for introducing mutations into a desired gene/allele of a plant cell or plant are known in the art. Therefore, mutant alleles of a Emb2 protein-encoding gene can be produced in plant cells or plants by using these methods. Examples for such technologies are in particular mutagenesis techniques or enzymes which induce double stranded DNA breaks (double stranded DNA break inducing enzyme (DSBI)) in the genome of plants. Known and practised technologies are rare-cleaving endonucleases and custom-tailored rare-cleaving endonucleases including but not limited to homing endonucleases, also called meganucleases, transcription activator-like effectors fused to the catalytic domain of a nuclease (TALENs) and so-called CRISPR/Cas systems. CRISPR/Cas systems is used broadly herein, and does not only encompass the use of the Cas9 nuclease (Crispr/Cas9 system), but also other Crispr systems e.g. using other nucleases, such as Cpf1. These techniques can also be referred to as genome editing techniques or gene editing techniques.

Thus, technologies such as mutagenesis or genome editing techniques are eligible for introducing a mutation into genes in plant cells or plants. Therefore, plant cells and plants according to the invention having a mutant allele of a Emb2 protein-encoding gene, wherein the mutation into the mutant allele was introduced by genome editing techniques, e.g. using rare-cleaving endonucleases or custom-tailored rare-cleaving endonucleases, are also an embodiment of the invention. Concerning custom-tailored rare-cleaving endonucleases the mutation in the mutant allele of Emb2 protein has preferably been introduced by a meganuclease, a TALENs or a CRISPR/Cas system.

As used herein, a "double stranded DNA break inducing enzyme (DSBI)" is an enzyme capable of inducing a double stranded DNA break at a particular nucleotide sequence, called the "recognition site". Rare-cleaving endonucleases are DSBI enzymes that have a recognition site of about 14 to 70 consecutive nucleotides, and therefore have a very low frequency of cleaving, even in larger genomes such as most plant genomes.

"Homing endonucleases, also called meganucleases", constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrasts the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level.

A list of other rare cleaving meganucleases and their respective recognition sites is provided in Table I of WO 03/004659 (pages 17 to 20) (incorporated herein by reference). These include I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-Dhal, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tho I or PI-Tsp I.

Furthermore, methods are available to design "custom-tailored rare-cleaving endonucleases" that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO94/18313 or WO95/09233 and in Isalan et al., 2001, Nature Biotechnology 19, 656-660; Liu et al. 1997, Proc. Natl. Acad. Sci. USA 94, 5525-5530). Custom-made meganucleases can be produced by selection from a library of variants, as described in WO2004/067736. Custom made meganucleases with altered sequence specificity and DNA-binding affinity may also be obtained through rational design as described in WO2007/047859.

Another example of custom-designed endonucleases include the so-called "TALE nucleases (TALENs)", which are based on transcription activator-like effectors (TALEs) from the bacterial genus *Xanthomonas* fused to the catalytic domain of a nuclease (e.g. FOKI). The DNA binding specificity of these TALEs is defined by repeat-variable diresidues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see e.g. Boch et al., 2009, Science 326:p 1509-1512; Moscou and Bogdanove, 2009, Science 326:p 1501; Christian et al., 2010, Genetics 186:p 757-761; and WO10/079430, WO11/072246, WO2011/154393, WO11/146121, WO2012/001527, WO2012/093833, WO2012/104729, WO2012/138927, WO2012/138939). WO2012/138927 further describes monomeric (compact) TALENs and TALENs with various catalytic domains and combinations thereof.

Recently, a new type of customizable endonuclease system has been described; the so-called "CRISPR/Cas system", which employs a special RNA molecule (crRNA) conferring sequence specificity to guide the cleavage of an associated nuclease, e.g. Cas9 (Jinek et al, 2012, Science 337:p 816-821). Such custom designed rare-cleaving endonucleases are also referred to as non-naturally occurring rare-cleaving endonucleases.

A further method known in the art for introducing mutations into a gene/allele of a plant cell or plant is the so-called "in vivo mutagenesis". Further discussion of the respective technology is given herein below.

Plant cells or plants according to the invention having a mutant allele of a Emb2 protein-encoding gene, wherein the mutation into the allele was introduced by in vivo mutagenesis are also an embodiment of the invention.

Various technologies commonly known in the art are suited to create insertion mutations in plant cells or plants.

Further embodiments of the invention are plant cells and plants according to the invention having a mutant allele of a Emb2 protein-encoding gene, wherein the mutation into the mutant allele was introduced by insertion mutagenesis.

The plant cells according to the invention and plants according to the invention having a mutant allele of a Emb2 protein-encoding gene can be produced by so-called insertion mutagenesis. In particular, insertion of transposons and transfer DNA (T-DNA) sequences into genes/alleles encoding Emb2 proteins are suitable for decreasing the expression and/or activity of the respective genes/alleles in which they are integrated (Thorneycroft et al., 2001, Journal of experimental Botany 52 (361), 1593-1601).

Additional discussion of the respective technologies known to a person skilled in the art will be provided herein further below.

"Insertion mutagenesis" is to be understood to mean particularly the insertion of transposons or so-called transfer DNA (T-DNA) into a gene coding for a Emb2 protein, whereby, as a result of which, the activity of a Emb2 protein in the cell concerned is decreased or a non-functional Emb2 protein is produced.

In a further preferred embodiment, the plants according to the invention are male fertile plants.

The plants according to the invention are male fertile and produce seedless fruits when the mutant emb2 allele is present in homozygous form. The advantage of male fertile plants over male sterile plants is that they will produce viable pollen and thus there is no need to plant a second, so called pollinator plant in the same field for inducing fruit set and development on the seedless fruit producing female plant. The whole area under cultivation thus can be planted with plants producing seedless fruits, leading to an increase of yield of seedless fruits per area cultivated. Also, synchrony of flowering and fertilisation time is given for the male and female plant parts, because ovules and pollen are produced by the same plant. This ensures sufficient pollination to take place for producing the most possible amounts of fruits.

In context with the present invention, "male fertile plant" is to be understood to be a plant producing viable pollen. That viable or fertile pollen is produced can e.g. be shown by using the pollen from the respective plant for cross-pollinating another, different plant and obtaining viable seeds from this cross.

The seedless fruit producing phenotype of plants according to the invention in one aspect is not only be generated in diploid plants but also in polyploidy plants. In one aspect plants according to the invention produce seedless fruits also when they have different degree of ploidy. It is therefore well understood that the plant cells or plants according to the invention comprise plants having any degree of ploidy comprising plants with even numbered degree of ploidy (2n, 4n, 6n, 8n etc.) and plants with uneven numbered degree of ploidy (3n, 5n etc.). In one aspect, the mutant Emb2 protein-encoding gene is homozygous in diploid plants, but in another aspect the mutant Emb2 protein-encoding gene is homozygous in polyploid plants, such as tetraploid watermelons. "Homozygous in polyploid plants" means that the locus on each chromosome comprises the mutant allele and not the wild type allele of the gene.

Polyploidisation is widespread in plants. It is responsible for increasing genetic diversity and producing species showing increase in robustness, size, vigour and disease resistance. Obvious advantages for polyploid plants are heterosis and gene redundancy.

A number of today cultivated broad acre and plantation crops have undergone one or more genome duplications. Examples are cotton (multiplication factor ×6), potato (×2, ×3), bread wheat (×3), oil seeds (×3), corn (×2), soybean (×2), sunflower (×2), banana (×2), apple (×2) and coffee (×2) (Renny-Byfield 7 Wendel, 2014, American J. Botany, 101 (10), 1711-1725).

In particular in vegetable breeding, polyploidy in various plants was induced by the use of chemicals including colchicine, colchamine, oryzalin, colcemid, trifluralin or amiprophosmethyl. Examples for genome duplications in vegetables produced by the use of chemicals are diploid brussels sprouts from haploid plants (2×), tetraploid peas (2×), tetraploid watermelons (2×), tetraploid muskmelons (2×), tetraploid onions (2×), octaploid cocoyams (4×), tetraploid snake gourds (2×), triploid and tetraploid fluted pumpkins (1.5×, 2×), tetraploid cucumbers (2×) and tetraploid french beans (2×) (Kazi, 2015, J. Global Biosciences 4(3), 1774-1779).

Plants comprising a mutant allele of a Emb2 protein-encoding gene can be produced by various methods commonly known to a person skilled in the art.

A diploid plant comprising two copies of a mutant allele of a Emb2 protein-encoding gene can be used to make a tetraploid plant comprising four copies of a mutant allele of a Emb2 protein-encoding gene.

Such a tetraploid will have the same phenotype as the diploid, i.e. produce seedless fruits (which are tetraploid) and viable pollen. So, for example the diploid watermelon seeds deposited under accession number NCIMB 43064 can be used to make a tetraploid watermelon plant/seed comprising four copies of the specific mutant emb2 allele present in the deposited seed, by doubling the chromosomes of a plant homozygous for the mutant emb2 allele.

It is commonly understood in the art that sexually reproducing cells of plants (pollen and ovule) comprise a set of chromosomes which is half of the set of the remaining cells of said plant. Plant pollen and ovules can be regenerated into whole plants. In case of plants having an even numbered degree of ploidy it is therefore generally possible to reduce the degree of ploidy by half upon regeneration of pollen or ovules. From plants according to the invention having an even numbered degree of ploidy (e.g. 2n, 4n, 6n, 8n etc.) plants having a bisected set of chromosomes (e.g. 1n, 2n, 3n, 4n, etc., respectively) can be produced by means of pollen or ovule regeneration.

Triploid plants can be produced by crossing a diploid (2n) plant according to the invention with a tetraploid (4n) plant according to the invention. The hybrid plant seeds originating from said cross will be triploid (3n). Preferably the diploid (2n) and tetraploid (4n) plants according to the invention crossed with each other both are homozygous for a mutant Emb2 protein-encoding gene. The resulting triploid seeds (and triploid plants grown from the seeds) will have three copies of the mutant allele. The diploid plant used for producing a triploid hybrid can e.g. be plants obtained/obtainable from seeds being homozygous for a mutant allele of a Emb2 protein-encoding gene, e.g. obtained from seeds of deposit accession number NCIMB 43064 or any other plant comprising a mutant emb2 allele.

Plants (e.g. diploid, triploid or tetraploid, or another ploidy) and plant parts (such as fruits) comprising a mutant allele of a Emb2 protein-encoding gene obtainable/obtained by one of the methods just described are also an embodiment of the invention. Also seeds from which such plants can be grown are an embodiment of the invention.

In a preferred embodiment of the invention the plant cells or plants according to the invention have an even numbered degree of ploidy, preferably, they are diploid (2n) or tetraploid (4n).

Plants with an uneven numbered degree of ploidy, e.g. triploid (3n) plants are commonly male and female sterile, because during meiosis the chromosomes cannot be equally divided to the daughter cells. The advantage of plants with an even numbered degree of ploidy, e.g. diploid (2n) or tetraploid (4n) plants over plants with an uneven numbered degree of ploidy, e.g. triploid (3n) plants is that plants with even numbered degree of ploidy can produce viable pollen and/or viable ovules. As a consequence plants with an even numbered degree of ploidy can be grown without the need of a second, different, so called pollinator plant needed for inducing fruit set and development in the plant with uneven numbered degree of ploidy. Pollinator plants will also produce fruits which commonly will be seed bearing (or seeded). These seed bearing fruits have to be separated from the seedless fruits upon or after harvesting. Thus, plants having an even numbered degree of ploidy have the advantage over plants with uneven numbered degree of ploidy that there is no need to separate undesired seed bearing fruits produced by pollinator plants from the desired seedless fruits.

"Even numbered degree of ploidy" in context of the present invention means that the number of homologous chromosome sets present in a cell or organism when divided by two results in an integer. The cells or organisms thus are diploid (2n), tetraploid (4n), hexaploid (6n), octaploid (8n) etc.

"Uneven numbered degree of ploidy" in context of the present invention means that the number of homologous chromosome sets present in a cell or organism when divided by two does not result an integer. The cells or organisms thus are haploid (1n), triploid (3n) etc.

"Diploid plant cell or plant" in context of the present invention means a plant, vegetative plant part(s), fruit or seed or plant cell, having two sets of corresponding chromosomes, designated herein as 2n.

"Tetraploid cell or plant" in context of the present invention means a plant, vegetative plant part(s), fruit or seed or plant cell, having four sets of corresponding chromosomes, designated herein as 4n.

The plant cells according to the invention can be those plant cells which can be regenerated into a whole plant or those which cannot be regenerated into whole plants. Thus, the plant cells according to the invention may be those plant cells which are not eligible to regenerate a whole plant.

In a preferred embodiment the plants according to the invention are male fertile and have an even numbered degree of ploidy. Preferably, plants according to the invention are male fertile and are diploid (2n) or tetraploid (4n).

In another preferred embodiment, the plants according to the invention are stenospermocarpic plants. More preferably the plants according to the invention are male fertile stenospermocarpic plants. Even further preferred the plants according to the invention are male fertile, stenospermocarpic and have an even numbered degree of ploidy. In particular preferred are plants according to the invention which are male fertile, stenospermocarpic, diploid (2n) or tetraploid (4).

Stenospermocarpic plants produce seedless fruits. Male fertile stenospermocarpic plants have the advantage over known stenospermocarpic plants that they do not need a different pollinator plant grown in the same area but that they nevertheless produce seedless fruits. Pollinator plants will produce undesired seed bearing fruits, which will have to be separated from the seedless fruits. Thus, stenospermocarpic male fertile plants have the advantage that there is no competition for growing space and nutrients between a plant producing the desired seedless fruits and the polliniser plants, which increases yield of the desired seedless fruits per planting area available.

"Stenospermocarpy" is generally understood in the art and also to be understood in connection with the present invention to mean that induction of fruit set and development requires pollination but without the fruits producing mature or viable seeds. Mature or viable seeds are not developed in stenospermocarpic plants due to arrested seed development or degradation of ovules and/or embryos and/or endosperm or abortion of the ovules and/or embryos and/or endosperm before maturity is reached.

To be differentiated from stenospermocarpy is parthenocarpy. "Parthenocarpy" is generally understood in the art and also to be understood in connection with the present invention to describe the development of fruits without fertilization of the female ovule. A pollination process is not needed for producing fruits which fruits however as a consequence of the lack of pollination are seedless.

In a further preferred embodiment of the invention, the plants according to the invention which are homozygous for a mutant emb2 allele, i.e. comprise two copies in a diploid, four copies in a tetraploid, etc.) produce seedless fruits.

The fruits of plants according to the invention may contain structures which have a seed like appearance, see e.g. FIG. 2B (on the left, labelled EMB2), showing seed-like structures (also referred to as defective seeds) of the seedless fruit, of a watermelon plant homozygous for the mutant emb2 allele.

These structures having a seed like appearance, but are much smaller than normal viable seeds (see wild type, mature viable seeds in FIG. 2B on the right). They may be white or they may develop a brown seed coat, resulting in small, brown, irregular structures, which are not viable.

In a more preferred embodiment of the invention the plants according to the invention produce seedless fruits and/or are male fertile and/or have an even degree of ploidy and/or are stenospermocarpic. Even more preferred the plants according to the invention produce seedless fruits, are male fertile, are diploid (2n) or tetraploid (4n) and are stenospermocarpic.

The term "fruit" in its botanical meaning is commonly understood to be a seed bearing structure developed from the ovary of angiosperm flowers.

A "seedless fruit" as commonly used in the art and in particular in breeding, although being somehow contradicting the botanical meaning of "fruit", is to be understood in context with the present invention to be a fruit without mature or viable seeds. Mature or viable seeds can be germinated in soil under conditions appropriate for the respective plant and grown into plants. This test can be used to determine if a plant produces seedless fruits. Seedless fruits will not produce seed which will germinate and grow into a plant under conditions appropriate for the respective plant.

By knowing the causative gene for the production of seedless fruits disclosed herein, it is now possible to produce seedless fruit producing plants by various known methods. These methods can rely on producing and selecting plants having mutant alleles resulting in a knock-down or knock-out of gene expression and consequently less or no wild type Emb2 protein being produced, or mutant alleles encoding mutant Emb2 proteins having a decreased function or loss-of-function compared to the wild type protein. To generate such mutant alleles conventional mutagenic agents, like chemicals or high energy radiation (e.g. x-rays, neutron radiation, gamma radiation or UV radiation) may be used. It is also possible to generate mutant alleles by means of biotechnology methods as described above (e.g. gene editing technology).

Plants according to the invention can be produced by introducing one or more mutations into an allele of a Emb2 protein-encoding gene.

A further embodiment of the present invention therefore concerns a method for production of a plant comprising the steps of
 a) providing a population of mutant plants,
 b) optionally selecting a male fertile plant producing seedless fruits,
 c) determining if a plant of the mutant population of a) or selected under b) has a mutation in an allele of a Emb2 protein-encoding gene, optionally
 d) growing/cultivating the plants obtained under c).

In one aspect is a method for production of a plant comprising the steps of
 a) introducing mutations in a population of plants (and optionally selfing the plants)
 b) optionally selecting a male fertile plant producing seedless fruit
 c) determining if the plant selected under b) has a mutation in an allele encoding a Emb2 protein-encoding gene and selecting a plant comprising such a mutation, and optionally
 d) growing/cultivating the plants obtained under c).

However, in one aspect the order of the steps can also be different, comprising:
a) providing a population of mutant plants,
b) determining if a plant of the mutant population of a) has a mutation in an allele of a Emb2 protein-encoding gene, optionally
c) selecting a plant comprising a mutation in an allele of a Emb2-protein encoding gene, and optionally
d) selfing the plant of b) or c) to generate a plant comprising the mutant allele in homozygous form, and optionally
e) determining if the plant of step c) or d) produces seedless fruit.

Or the steps may comprise:
a) introducing mutations in a population of plants (and optionally selfing the plants)
b) determining if a plant of a) has a mutation in an allele encoding a Emb2 protein-encoding gene and optionally
c) selecting a plant comprising such a mutation, and optionally
d) selfing the plant of b) or c) to generate a plant comprising the mutant allele in homozygous form, and optionally
e) determining if the plant of step c) or d) produces seedless fruit.

In the above methods, the population of plants in step a) may be of any species, e.g. watermelon plants, cucumber plants, melon plants, or other Cucurbitaceae plants; or tomato plants, or pepper plants, or other Solanaceae plants. If the plant species is a Cucurbitaceae species, then the mutation is in an allele encoding a wild type Emb2 protein comprising at least 70%, 75%, 78%, 80%, 85%, 90%, 92%, 94%, 95%, 96%, 97%, 98% or 99% or more to SEQ ID NO: 6 and/or to SEQ ID NO: 4 and/or to SEQ ID NO: 5. If the plant species is a Solanaceae species, then the mutation is in an allele encoding a wild type Emb2 protein comprising at least 70%, 75%, 78%, 80%, 85%, 90%, 92%, 94%, 95%, 96%, 97%, 98% or 99% or more to SEQ ID NO: 9 and/or to SEQ ID NO: 10 and/or to SEQ ID NO: 11.

Optionally, the above methods comprises selecting a plant comprising at least one copy of a mutant allele of a gene encoding Emb2 protein. The mutant allele, when in homozygous form, results in the production of seedless fruits. The plant comprising the allele is male fertile.

"Population of plants" shall mean in context with the present invention more than one whole plant and shall comprise also plant parts, fruits, seeds or plant cells. The plant parts, fruits, seeds or plant cells in each case originate from more than one plant meaning that concerning a "population of plant parts, fruits, seeds or plant cells", the plant parts, fruits, seeds or plant cells, respectively, are not obtained from a single plant but from a plurality of plants.

Chemical substances, which can be used to produce chemically induced mutations, and the mutations resulting from the effect of the corresponding mutagens are, for example described in Ehrenberg and Husain, 1981, (Mutation Research 86, 1-113), Müller, 1972 (Biologisches Zentralblatt 91 (1), 31-48). The production of rice mutants using gamma radiation, ethyl methane sulphonate (EMS), N-methyl-N-nitrosurea or sodium azide (NaN₃) is described, for example, in Jauhar and Siddiq (1999, Indian Journal of Genetics, 59 (1), 23-28), in Rao (1977, Cytologica 42, 443-450), Gupta and Sharma (1990, *Oryza* 27, 217-219) and Satoh and Omura (1981, Japanese Journal of Breeding 31 (3), 316-326). The production of wheat mutants using NaN₃ or maleic hydrazide is described in Arora et al. (1992, Annals of Biology 8 (1), 65-69). An overview of the production of wheat mutants using different types of energy-rich radiation and chemical substances is presented in Scarascia-Mugnozza et al. (1993, Mutation Breeding Review 10, 1-28). Svec et al. (1998, Cereal Research Communications 26 (4), 391-396) describes the use of N-ethyl-N-nitrosurea for producing mutations in triticale. The use of MMS (methyl methane sulphonic acid) and gamma radiation for the production of millet mutants is described in Shashidhara et al. (1990, Journal of Maharashtra Agricultural Universities 15 (1), 20-23).

The manufacture of mutants in plant species, which mainly propagate vegetatively, has been described, for example, for potatoes, which produce a modified starch (Hovenkamp-Hermelink et al. (1987, Theoretical and Applied Genetics 75, 217-221) and for mint with increased oil yield or modified oil quality (Dwivedi et al., 2000, Journal of Medicinal and Aromatic Plant Sciences 22, 460-463).

All these methods are basically suitable in the method for production of a plant according to the invention for producing mutant alleles in genes encoding a Emb2 protein. In the method for production of a plant according to the invention preferably the mutant population is produced by applying ethyl methane sulphonate (EMS) to plants or seeds of plants for introducing mutations.

Selecting plants producing seedless fruits can be done by simply visible screening/phenotyping the fruits. As the phenotype of seedlessness is only seen in homozygous condition, selfing of the population of mutagenized plants is preferred before phenotyping. That fertile pollen is produced by a plant can e.g. be shown by using the pollen from the respective plant for cross-pollinating another, different, female fertile plant. In case the seeds from this cross are viable the pollen used in the cross-pollinations was fertile. Mutations in the appropriate alleles, in particular in alleles of Emb2 protein-encoding genes, can be found with the help of methods known to the person skilled in the art. In particular, analyses based on hybridisations with probes (Southern Blot), amplification by means of polymerase chain reaction (PCR), sequencing of related genomic sequences and the search for individual nucleotide exchanges can be used for this purpose. A method of identifying mutations based on hybridisation patterns is, for example, the search for restriction fragment length differences (Restriction Fragment Length Polymorphism, RFLP) (Nam et al., 1989, The Plant Cell 1, 699-705; Leister and Dean, 1993, The Plant Journal 4 (4), 745-750). A method based on PCR is, for example, the analysis of amplified fragment length differences (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160). The use of amplified fragments excised with restriction endonucleases (Cleaved Amplified Polymorphic Sequences, CAPS) can also be used upon for the identification of mutations (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753). Methods for the determination of SNPs have been described by Qi et al. (2001, Nucleic Acids Research 29 (22), e116) Drenkard et al. (2000, Plant Physiology 124, 1483-1492) and Cho et al. (1999, Nature Genetics 23, 203-207) amongst others. Methods, which allow several plants to be investigated for mutations in certain genes in a short time, are particularly suitable. Such a method, so-called TILLING (Targeting Induced Local Lesions IN Genomes), has been described by McCallum et al. (2000, Plant Physiology 123, 439-442).

It is well known in the art, that today also other methods are useful for identifying plant cells according to the invention and plants according to the invention having a mutant allele of a Emb2 protein-encoding gene. These methods comprise e.g. so-called forward screening approaches. In the forward screening approaches a mutant population is produced. Plants of the mutant population, e.g. M2 plants are screened for seedless fruit producing plants, which are then crossed to various different inbred lines for producing a mapping population. The mapping population is then analysed by methods well known in the art to identify the allele causing the seedless fruit phenotype. Other methods for identifying if a plant cell or plant comprises a mutant allele of a Emb2 protein-encoding gene comprise sequencing of the respective alleles and SNP marker analyses with methods common in the art and e.g. discussed in Thomson (2014, Plant Breeding and Biotechnology 2, 195-212).

Also analysis of Emb2 mRNA being expressed, and optionally quantified, can be used, e.g. to identify mutants having reduced or no Emb2 gene expression.

These methods are basically suitable for identifying plant cells according to the invention and plants according to the invention having a mutant allele of a Emb2 protein-encoding gene.

Growing the male fertile, seedless fruit producing plants having a mutant allele of a Emb2 protein-encoding gene identified in the method for production of a plant according to the invention can be done by conventional methods in a greenhouse or in the field. Cultivation and/or propagation of these plants can be done by methods common in the art like e.g. by cuttings, in vitro tissue, cell, protoplast, embryo or callus cultures or micropropagation or by grafting cuttings to a different rootstock.

In a preferred embodiment of the invention, the methods for production of a plant according to the invention are used for producing plants according to the invention. The preferred embodiments described above for plants according to the invention are accordingly applicable to the methods for production of a plant according to the invention.

Plants obtainable/obtained by the method for production of a plant according to the invention are also an embodiment of the invention.

Various methods available in gene technology offer further possibilities to produce plants having mutant alleles of a Emb2 protein-encoding gene or having non-functional Emb2 proteins or having decreased activity of Emb2 proteins or showing a decreased expression or no expression of the gene encoding an Emb2 protein.

These methods are based on the introduction of a foreign or of several foreign nucleic acid molecules into the genome of plant cells or plants and therefore are basically suitable for producing plant cells according to the invention and plants according to the invention.

A further embodiment of the invention therefore concerns a method for production of a plant comprising the steps of
 a) introduction of a foreign nucleic acid molecule into a plant, wherein the foreign nucleic acid molecule is chosen from the group consisting of
  i) DNA molecules, which code at least one antisense RNA, which effects a reduction in the expression of an endogenous gene encoding a Emb2 protein;
  ii) DNA molecules, which by means of a co-suppression effect lead to the reduction in the expression of an endogenous gene encoding a Emb2 protein;
  iii) DNA molecules, which code at least one ribozyme, which splits specific transcripts of an endogenous gene encoding a Emb2 protein;
  iv) DNA molecules, which simultaneously code at least one antisense RNA and at least one sense RNA, wherein the said antisense RNA and the said sense RNA form a double-stranded RNA molecule, which effects a reduction in the expression of an endogenous gene encoding a Emb2 protein having (RNAi technology);
  v) nucleic acid molecules introduced by means of in vivo mutagenesis, which lead to a mutation or an insertion of a heterologous sequence in an endogenous gene encoding a Emb2 protein, wherein the mutation or insertion effects a reduction in the expression of a gene encoding a Emb2 protein or results in the synthesis of an inactive Emb2 protein;
  vi) nucleic acid molecules, which code an antibody, wherein the antibody results in a decrease in the activity of an endogenous gene encoding a Emb2 protein due to the bonding of the antibody to an endogenous Emb2 protein,
  vii) DNA molecules, which contain transposons, wherein the integration of these transposons leads to a mutation or an insertion in an endogenous gene encoding a Emb2 protein, which effects a reduction in the expression of an endogenous gene encoding a Emb2 protein, or results in the synthesis of an inactive Emb2 protein;
  viii) T-DNA molecules, which, due to insertion in an endogenous gene encoding a Emb2 protein, effect a reduction in the expression of an endogenous gene encoding a Emb2 protein, or result in the synthesis of an inactive Emb2 protein, and/or
  ix) nucleic acid molecules encoding rare-cleaving endonucleases or custom-tailored rare-cleaving endonucleases preferably a meganuclease, a TAL-ENs or a CRISPR/Cas system
 b) selecting a plant producing seedless fruits, optionally
 c) verifying if the plant selected under b) has a decreased activity of a Emb2 protein compared to wild type plants into whose genome no foreign nucleic acid molecules had been integrated, and optionally
 d) growing/cultivating the plants obtained under c).

In one embodiment of the invention, the method according to the invention comprising introducing a foreign nucleic acid molecule into a plant cell concerns a method for the production of a male fertile plant, meaning that selection of a plant being male fertile and producing seedless fruit takes place (in step b and/or c).

The decrease of the activity of Emb2 proteins in plant cells or plants according to the invention or in the method according to the invention comprising introducing a foreign nucleic acid molecule into a plant cell can be brought about by expression of antisense or co-suppression constructs.

For inhibiting the expression of genes by means of antisense or co-suppression technology, a DNA molecule can be used, for example, which includes the whole coding sequence for a Emb2 protein, including any existing flanking sequences, as well as DNA molecules, which include only parts of the coding sequence, whereby these parts must be long enough to produce an antisense effect or a co-suppression effect respectively in the cells. In general, sequences up to a minimum length of 20 bp or 21 bp (or nucleotides), preferably a minimum length of at least 100 bp (or nucleotides), particularly preferably of at least 500 bp (or nucleotides) are suitable. For example, the DNA molecules have a length of 21-100 bp (or nucleotides), preferably of 100-500 bp (or nucleotides), particularly preferably over 500 bp (or nucleotides).

The use of DNA sequences, which have a high degree of identity with the endogenous sequences occurring in the plant cell and which encode Emb2 proteins, is also suitable for antisense or co-suppression preparations. The minimum identity should be greater than ca. 65%, preferably greater than 80%. The use of sequences with identities of at least 90%, in particular between 95% and 100%, is to be preferred. The meaning of the term "sequence identity" is defined elsewhere herein.

Furthermore, the use of introns, i.e. of non-coding areas of genes, which code for Emb2 proteins, is also conceivable for achieving an antisense or a co-suppression effect. The use of intron sequences for inhibiting the gene expression of genes, which code for starch biosynthesis proteins, has e.g. been described in the international patent applications WO97/04112, WO97/04113, WO98/37213, WO98/37214.

The person skilled in the art knows how to achieve an antisense and a co-suppression effect. For example, the method of co-suppression inhibition has been described in Jorgensen (Trends Biotechnol. 8 (1990), 340-344), Niebel et al., (Curr. Top. Microbiol. Immunol. 197 (1995), 91-103), Flavell et al. (Curr. Top. Microbiol. Immunol. 197 (1995), 43-46), Palaqui and Vaucheret (Plant. Mol. Biol. 29 (1995), 149-159), Vaucheret et al., (Mol. Gen. Genet. 248 (1995), 311-317), de Borne et al. (Mol. Gen. Genet. 243 (1994), 613-621).

The expression of ribozymes for reducing the activity of particular enzymes in cells is also known to the person skilled in the art, and is described, for example, in EP-B1 0321201. The expression of ribozymes in plant cells has been described, for example, in Feyter et al. (Mol. Gen. Genet. 250, (1996), 329-338).

The decrease of the activity of Emb2 proteins in plant cells or plants according to the invention or in the method according to the invention comprising introducing a foreign nucleic acid molecule into a plant cell can also be brought about by the simultaneous expression of sense and antisense RNA molecules (RNAi technology) of the respective target gene to be repressed, preferably of the Emb2 protein encoding gene.

This can be achieved, for example, by the use of chimeric constructs, which contain "inverted repeats" of the respective target gene or parts of the target gene. In this case, the generic constructs code for sense and antisense RNA molecules of the respective target gene. Sense and antisense RNA are synthesized simultaneously in planta as an RNA molecule, wherein sense and antisense RNA are separated from one another by a spacer, and are able to form a double-stranded RNA molecule.

It has been shown that the introduction of inverted repeat DNA constructs into the genome of plant cells or plants is a very effective method of repressing the genes corresponding to the inverted repeat DNA constructs (Waterhouse et al., Proc. Natl. Acad. Sci. USA 95, (1998), 13959-13964; Wang and Waterhouse, Plant Mol. Biol. 43, (2000), 67-82; Singh et al., Biochemical Society Transactions Vol. 28 part 6 (2000), 925-927; Liu et al., Biochemical Society Transactions Vol. 28 part 6 (2000), 927-929); Smith et al., (Nature 407, (2000), 319-320; international patent application WO99/53050 A1). Sense and antisense sequences of the target gene or of the target genes can also be expressed separately from one another by means of similar or different promoters (Nap, J-P et al, 6th International Congress of Plant Molecular Biology, Quebec, 18-24 Jun. 2000; Poster S7-27, Presentation Session S7). The decrease of the activity of Emb2 proteins in plant cells according to the invention or plants according to the invention can therefore also be achieved by producing double-stranded RNA molecules. In this regard, "inverted repeats" of DNA molecules of Emb2 protein-encoding genes or cDNAs are preferably introduced into the genome of plants, wherein the DNA molecules (Emb2 protein encoding gene or cDNA or fragments of these genes or cDNAs) to be transcribed are under the control of a promoter, which controls the expression of said DNA molecules.

Fragments of any of the nucleic acid molecules encoding Emb2 proteins are therefore also an aspect of the invention. Such fragments have various uses, e.g. as primers or probes, or they can be incorporated into transformation vectors and used to generate plants producing seedless fruits.

Such fragments of nucleic acid molecules encoding Emb2 proteins may be of various sizes, e.g. at least 10 nucleotides, at least 20, at least 30, at least 40, at least 50, at least 60, at least 70, at least 80, at least 90, at least 100, at least 200, at least 300, at least 400, at least 500 nucleotides or more.

In addition to this, it is known that the formation of double-stranded RNA molecules from promoter DNA molecules in plants in trans can lead to methylation and transcriptional inactivation of homologous copies of these promoters, which are to be referred to in the following as target promoters (Mette et al., EMBO J. 19, (2000), 5194-5201). It is therefore possible to reduce the gene expression of a particular target gene (e.g. Emb2 protein-encoding gene), which is naturally under the control of this target promoter, by deactivating the target promoter. This means that, in this case, the DNA molecules, which include the target promoters of the genes to be repressed (target genes), in contrast to the original function of promoters in plants, are not used as control elements for the expression of genes or cDNAs, but are themselves used as transcribable DNA molecules.

For the production of double-stranded target promoter RNA molecules in planta, which can occur there as RNA hairpin molecules, constructs are preferably used, which contain the "inverted repeats" of the target promoter DNA molecules, wherein the target promoter DNA molecules are under the control of a promoter, which controls the gene expression of said target promoter DNA molecules. These constructs are subsequently introduced into the genome of plants. The expression of the "inverted repeats" of said target promoter DNA molecules in planta leads to the formation of double-stranded target promoter RNA molecules (Mette et al., EMBO J. 19, (2000), 5194-5201). The target promoter can be inactivated by this means. The decrease of the activity of Emb2 proteins in plant cells according to the invention and plants according to the invention can therefore also be achieved by the introduction of double-stranded RNA molecules of promoter sequences of Emb2 protein-encoding genes into plant cells or plants. In this regard, "inverted repeats" of promoter DNA molecules of Emb2 protein-encoding genes are preferably introduced into the genome of plants, wherein the target promoter DNA molecules (promoter of a Emb2 protein-encoding gene) to be transcribed are under the control of a promoter, which controls the expression of said target promoter DNA molecules.

For inhibiting the expression of genes by means of the simultaneous expression of sense and antisense RNA molecules (RNAi technology), a DNA molecule can be used, for example, which includes the whole coding sequence for a Emb2 protein, including any existing flanking sequences, as well as DNA molecules, which include only parts of the coding sequence, whereby these parts must be long enough to produce a so-called RNAi effect in the cells. The parts of the Emb2 protein encoding gene can be chosen from coding sequences, non-translated down- or up-stream sequences, introns, promoters and/or enhancers. In general, sequences with a minimum length of 20 bp (or nucleotides), preferably a minimum length of at least 25 bp (or nucleotides), particularly preferably of at least 50 bp (or nucleotides) are suitable. For example, the DNA molecules have a length of 20 to 25 bp (or nucleotides), preferably of 26 to 50 bp (or nucleotides), particularly preferably greater than 50 bp (or nucleotides).

The use of DNA sequences, which have a high degree of identity with the endogenous sequences occurring in the plant cells and which code a Emb2 protein, is also suitable for the simultaneous expression of sense and antisense RNA molecules (RNAi technology). The minimum identity should be greater than ca. 65%, preferably greater than 80%. The use of sequences with identities of at least 90%, in particular between 95% and 100%, is to be particularly preferred.

The decrease of the activity of Emb2 proteins in plant cells according to the invention and plants according to the invention or in the method according to the invention comprising introducing a foreign nucleic acid molecule into a plant cell can be achieved by so-called "in vivo mutagenesis", in which a hybrid RNA-DNA oligonucleotide ("Chimeroplast") is introduced into plant cells (Kipp, P. B. et al., Poster Session at the "5$^{th}$ International Congress of Plant Molecular Biology, 21-27 Sep. 1997, Singapore; R. A. Dixon and C. J. Arntzen, meeting report on "Metabolic Engineering in Transgenic Plants", Keystone Symposia, Copper Mountain, Colo., USA, TIBTECH 15, (1997), 441-447; international patent application WO 9515972; Kren et al., Hepatology 25, (1997), 1462-1468; Cole-Strauss et al., Science 273, (1996), 1386-1389; Beetham et al., 1999, PNAS 96, 8774-8778).

A part of the DNA components of the RNA-DNA oligonucleotide is homologous to a nucleic acid sequence of an endogenous Emb2 protein-encoding gene, but, in comparison with the nucleic acid sequence of an endogenous Emb2 protein-encoding gene, it has a mutation or contains a heterologous region, which is surrounded by the homologous regions. By base pairing of the homologous regions of the RNA-DNA oligonucleotide and the endogenous nucleic acid molecule followed by homologous recombination, the mutation or heterologous region contained in the DNA components of the RNA-DNA oligonucleotide can be transferred into the genome of a plant cell. This leads to a decrease of the activity of one or more Emb2 proteins.

The decrease of the activity of Emb2 proteins in plant cells according to the invention and plants according to the invention or in the method according to the invention comprising introducing a foreign nucleic acid molecule into a plant cell can be achieved by introducing nucleic acid molecules encoding antagonists/inhibitors of Emb2 proteins into a plant cell. The person skilled in the art knows that he can achieve a decrease of the activity of Emb2 proteins by the expression of non-functional derivatives, in particular trans-dominant mutations, of such proteins, and/or by the expression of antagonists/inhibitors of such proteins. Antagonist/inhibitors of such proteins include, for example, antibodies, antibody fragments or molecules with similar bonding characteristics. For example, a cytoplasmatic scFv antibody has been used to modulate the activity of the phytochrome A protein in genetically modified tobacco plants (Owen, Bio/Technology 10 (1992), 790-4; Review: Franken, E, Teuschel, U. and Hain, R., Current Opinion in Biotechnology 8, (1997), 411-416; Whitelam, Trends Plant Sci. 1 (1996), 268-272; Conrad and Manteufel, Trends in Plant Science 6, (2001), 399-402; De Jaeger et al., Plant Molecular Biology 43, (2000), 419-428). The decrease of the activity of a branching enzyme in potato plants by expressing a specific antibody has been described by Jobling et al. (Nature Biotechnology 21, (2003), 77-80). Here, the antibody was provided with a plastid target sequence so that the inhibition of proteins localised in plastids was guaranteed.

The decrease of the activity of Emb2 proteins in plant cells according to the invention and plants according to the invention or in the method according to the invention comprising introducing a foreign nucleic acid molecule into a plant cell can be achieved by introducing nucleic acid molecules comprising transposon sequences into the plant cell. Insertion of transposon sequences into the sequence of an endogenous Emb2 protein encoding gene, will effect a reduction in the expression of an endogenous Emb2 protein.

The transposons can be endogenous transposons (homologous to the plant) and also those that do not occur naturally in said cell (heterologous to the plant) but in each case have to be introduced into a plant cell or plant by means of genetic engineering methods, such as transformation of a cell, for example. Changing the expression of genes by means of transposons is known to the person skilled in the art. An overview of the use of endogenous and heterologous transposons as tools in plant biotechnology is presented in Ramachandran and Sundaresan (2001, Plant Physiology and Biochemistry 39, 234-252). The possibility of identifying mutations in which specific genes have been inactivated by transposon insertion mutagenesis is presented in an overview by Maes et al. (1999, Trends in Plant Science 4 (3), 90-96). The production of rice mutants with the help of endogenous transposons is described by Hirochika (2001, Current Opinion in Plant Biology 4, 118-122). The identification of maize genes with the help of endogenous retrotransposons is presented, for example, by Hanley et al. (2000, The Plant Journal 22 (4), 557-566). The possibility of manufacturing mutants with the help of retrotransposons and methods of identifying mutants are described by Kumar and Hirochika (2001, Trends in Plant Science 6 (3), 127-134). The activity of technological (artificial) transposons in different species has been described both for dicotyledonous and for monocotyledonous plants: e.g. for rice (Greco et al., 2001, Plant Physiology 125, 1175-1177; Liu et al., 1999, Molecular and General Genetics 262, 413-420; Hiroyuki et al., 1999, The Plant Journal 19 (5), 605-613; Jeon und Gynheung, 2001, Plant Science 161, 211-219), barley (2000, Koprek et al., The Plant Journal 24 (2), 253-263) *Arabidopsis thaliana* (Aarts et al., 1993, Nature 363, 715-717, Schmidt und Willmitzer, 1989, Molecular and General Genetics 220, 17-24; Altmann et al., 1992, Theoretical and Applied Genetics 84, 371-383; Tissier et al., 1999, The Plant Cell 11, 1841-1852), tomato (Belzile and Yoder, 1992, The Plant Journal 2 (2), 173-179) and potato (Frey et al., 1989, Molecular and General Genetics 217, 172-177; Knapp et al., 1988, Molecular and General Genetics 213, 285-290).

Basically, the plant cells according to the invention and the plants according to the invention can be produced both with the help of homologous and heterologous transposons.

In conjunction with the present invention, plant cells and plants according to the invention can also be produced by the use of so-called insertion mutagenesis (overview article: Thorneycroft et al., 2001, Journal of experimental Botany 52 (361), 1593-1601). The decrease of the activity of Emb2 proteins in plant cells according to the invention and plants according to the invention or in the method according to the invention comprising introducing a foreign nucleic acid molecule into a plant cell can be achieved by introducing nucleic acid molecules comprising T-DNA sequences into the plant cell.

T-DNA insertion mutagenesis is based on the fact that certain sections (T-DNA) of Ti plasmids from *Agrobacterium* can integrate into the genome of plant cells. The place of integration in the plant chromosome is not defined, but can take place at any point. If the T-DNA integrates into a part of the chromosome, which constitutes a gene function, then this can lead to a change in the gene expression and thus also to a change in the activity of a protein coded by the gene concerned. In particular, the integration of a T-DNA into the coding area of a protein often leads to the corresponding protein no longer being able to be synthesized at all, or no longer synthesized in active form, by the cell concerned. The use of T-DNA insertions for producing mutants is described, for example, for *Arabidopsis thaliana* (Krysan et al., 1999, The Plant Cell 11, 2283-2290; Atipiroz-Leehan and Feldmann, 1997, Trends in genetics 13 (4), 152-156; Parinov and Sundaresan, 2000, Current Opinion in Biotechnology 11, 157-161) and rice (Jeon and An, 2001, Plant Science 161, 211-219; Jeon et al., 2000, The Plant Journal 22 (6), 561-570). Methods for identifying mutants, which have been produced with the help of T-DNA insertion mutagenesis, are described, amongst others, by Young et al., (2001, Plant Physiology 125, 513-518), Parinov et al. (1999, The Plant cell 11, 2263-2270), Thorneycroft et al. (2001, Journal of Experimental Botany 52, 1593-1601), and McKinney et al. (1995, The Plant Journal 8 (4), 613-622).

T-DNA insertion mutants have been produced in great numbers for *Arabidopsis thaliana*, for example, and are made available by different culture collections ("Stock centre", e.g. Salk Institute Genomic Analysis Laboratory, 10010 N. Torrey Pines Road, La Jolla, Calif. 92037, world wide web at signal.salk.edu/).

T-DNA mutagenesis is basically suitable for the production of the plant cells and plants according to the invention, which have a decreased activity of a Emb2 protein.

In conjunction with the present invention, the term "foreign nucleic acid molecule" is understood to mean such a nucleic acid molecule that either does not occur naturally in the corresponding wild type plant cells or plants, or that does not occur naturally in the concrete spatial arrangement in wild type plant cells or plants, or that is localised at a place in the genome of the plant cell or plant at which it does not occur naturally. Preferably, the foreign nucleic acid molecule is a recombinant molecule, which consists of different elements, the combination or specific spatial arrangement of which does not occur naturally in plant cells or plants.

In principle, a foreign nucleic acid molecule can be any nucleic acid molecule that effects a decrease in the activity of a Emb2 protein. Such kind of nucleic acid molecules have been described herein above.

In conjunction with the present invention, the term "genome" is to be understood to mean the totality of the genetic material present in a plant cell. It is known to the person skilled in the art that, as well as the cell nucleus, other compartments (e.g. plastids, mitochondria) also contain genetic material.

A large number of techniques are available for the introduction of DNA into a plant host cell. These techniques include the transformation of plant cells with T-DNA using *Agrobacterium tumefaciens* or *Agrobacterium rhizogenes* as the transformation medium, the fusion of protoplasts, injection of nucleic acids, the electroporation of nucleic acids, the introduction of nucleic acids by means of the biolistic approach as well as other possibilities.

The use of Agrobacteria-mediated transformation of plant cells has been intensively investigated and adequately described in EP 120516; Hoekema, Ind.: The Binary Plant Vector System Offsetdrukkerij Kanters B. V., Alblasserdam (1985), Chapter V; Fraley et al., Crit. Rev. Plant Sci. 4, 1-46 and by An et al. EMBO J. 4, (1985), 277-287. For the transformation of potato, see Rocha-Sosa et al., EMBO J. 8, (1989), 29-33, for example.

The transformation of monocotyledonous plants by means of vectors based on *Agrobacterium* transformation has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726). The successful transformation of other types of cereal has also already been described, for example for barley (Wan and Lemaux, see above; Ritala et al., see above; Krens et al., Nature 296, (1982), 72-74) and for wheat (Nehra et al., Plant J. 5, (1994), 285-297; Becker et al., 1994, Plant Journal 5, 299-307).

All the above methods are suitable within the framework of the present invention. Transformation of vegetable crops is also commonly known in the art. In Curtis (2012, Springer Science & Business Media, ISBN: 1402023332, 9781402023330) besides others, methods for the transformation of coffee, pineapple, pear, radish, carrot, pea, cabbage, cauliflower and watermelon is disclosed. Transformation of vegetable crops like banana, citrus, mango, papaya, watermelon, avocado, grape, (sweet) melon, kiwifruit, coffee, cacao have been described in Pua and Davey (2007, Springer Science & Business Media, ISBN: 3540491619, 9783540491613).

For expressing nucleic acid molecules, like those conferring a gene silencing effect or being used for introducing mutations into an allele in plant cells or plants, these nucleic acid are preferably linked with regulatory DNA sequences, including those which initiate transcription in plant cells (promoters). At the same time, the promoter can be chosen so that expression takes place constitutively or only in a certain tissue, at a certain stage of the plant development or at a time determined by external influences. The promoter can be homologous or heterologous both with respect to the plant and with respect to the nucleic acid molecule. The nucleic acid molecules therefore commonly are not naturally occurring in plants but are recombinant nucleic acid molecules, meaning that the combination of different genetic elements (e.g. coding sequences, RNAi complementary sequence, promoters) comprised by the nucleic acid molecule are not present in this combination in nature.

Suitable promoters are commonly known in the art, for example, the promoter of the 35S RNA of the cauliflower mosaic virus and the ubiquitin promoter from maize for constitutive expression, the patatin promoter B33 (Rocha-Sosa et al., EMBO J. 8 (1989), 23-29) for tuber-specific expression in potatoes or a promoter, which only ensures expression in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989), 2445-2451) or, for endosperm-specific expression of the HMG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or shrunken-1 promoter (Werr et al., EMBO J. 4 (1985), 1373-1380). However, promoters can also be used, which are only activated at a time determined by external influences (see for example WO 9307279). Promoters of heat-shock proteins, which allow simple induction, can be of particular interest here. Furthermore, seed-specific promoters can be used, such as the USP promoter from *Vicia faba*, which guarantees seed-specific expression in *Vicia faba* and other plants (Fiedler et al., Plant Mol. Biol. 22 (1993), 669-679; Bäumlein et al., Mol. Gen. Genet. 225 (1991), 459-467).

The recombinant nucleic acid molecule may also contain a termination sequence (polyadenylation signal), which is used for adding a poly-A tail to the transcript. A function in the stabilisation of the transcripts is ascribed to the poly-A tail. Elements of this type are described in the literature (cf. Gielen et al., EMBO J. 8 (1989), 23-29) and can be exchanged at will.

Intron sequences can also be present, e.g. between the promoter and the coding region. Such intron sequences can lead to stability of expression and to increased expression in plants (Callis et al., 1987, Genes Devel. 1, 1183-1200; Luehrsen, and Walbot, 1991, Mol. Gen. Genet. 225, 81-93; Rethmeier, et al., 1997; Plant Journal. 12(4): 895-899; Rose and Beliakoff, 2000, Plant Physiol. 122 (2), 535-542; Vasil et al., 1989, Plant Physiol. 91, 1575-1579; X U et al., 2003, Science in China Series C Vol. 46 No. 6, 561-569). Suitable intron sequences are, for example, the first intron of the sh1 gene from maize, the first intron of the polyubiquitin gene 1 from maize, the first intron of the epsps gene from rice or one of the two first introns of the PAT1 gene from *Arabidopsis*.

What has been described herein concerning the verification if a plant has a mutation in a nucleic acid sequence or a gene or allele encoding a Emb2 protein and for growing/cultivating the plants for the method for producing a plant according to the invention is also applicable here for the method comprising introducing a foreign nucleic acid molecule into a plant cell according to the invention.

In a further embodiment of the present invention the methods for producing a plant according to the invention and the method according to the invention comprising introducing a foreign nucleic acid molecule into a plant cell comprise a further step consisting of the production of further plants from the plants obtained from step d) in each of the methods according to the invention. The further plants produced are characterised in that they comprise at least one mutant allele of a Emb2 protein encoding gene or that they have a decreased activity of a Emb2 protein due to the introduction of a foreign nucleic acid molecule as described herein above. These further plants can be produced by means of vegetative (agamic) or generative (gamic, sexual) reproduction. Suitable for vegetative propagation are, for example, cuttings, in vitro tissue, cell, protoplast, embryo or callus cultures, micropropagation, rhizomes or tubers. Other propagation material includes, for example, fruits, seeds, seedlings, being heterozygous or homozygous for a mutant allele of a Emb2 protein encoding genes, etc.

Techniques for vegetative (agamic) propagation, including micropropagation of plants are well known in the art and e.g. described for banana, citrus, mango, papaya, avocado, (sweet) melon, have been described in Pua and Davey (2007, Springer Science & Business Media, ISBN: 3540491619, 9783540491613). Sultana and Rhaman (2012, LAP Lambert Academic Publishing, ISBN-13: 978-3-8484-3937-9) e.g. disclose various tissue culture and micropropagation methods for watermelon.

Plants obtainable/obtained by a method according to the invention comprising introducing a foreign nucleic acid molecule into a plant cell, are also an embodiment of the invention.

A further embodiment of the invention concerns a method for propagating seedless fruit producing plants comprising the steps of
a) obtaining seeds from which a plant according to the invention grows or obtaining seeds deposited under accession number NCIMB 43064 or progeny thereof,
b) growing plants from the seeds obtained in step a),
c) selecting seedless fruit producing plants from the plants grown under step b),
d) propagating the plants selected under step c) by a method selected from the group consisting of
  i) grafting of parts of plants selected under step c) to another rootstock,
  ii) cultivating parts of plants selected under step c) in in vitro tissue culture and optionally regenerating new plants from the tissue culture,
  iii) optionally producing embryo or callus cultures from parts of plants selected under step c) and optionally regenerating new plants from the tissue culture,
  iv) optionally producing further plants by micropropagation techniques.

In one aspect a method of propagating a plant which is homozygous for a mutant emb2 allele comprises: grafting of parts of the plant to another rootstock, or cultivating parts of plants in in vitro tissue culture and optionally regenerating new plants from the tissue culture, or optionally producing embryo or callus cultures from parts of plants and optionally regenerating new plants from the tissue culture.

Propagation of plant parts by grafting and propagation and optionally regeneration of plants by tissue culture methods are well known in the art. Such methods are described in various scientific publications and are reviewed and summarized in a number of scientific books, like e.g. Smith (2012, Academic Press, ISBN-13: 978-0124159204), Gayatri & Kavyashree (2015, Alpha Science International Ltd, ISBN-13: 978-1842659618) etc. For watermelon, respective methods are described e.g. by Sultana and Rhaman (2012, LAP Lambert Academic Publishing, ISBN-13: 978-3848439379).

Plants or plant parts obtainable/obtained by methods for propagating seedless fruit producing plants according to the invention are also an embodiment of the invention.

In a further embodiment of the invention, all methods for producing a plant according to the invention or optionally the methods for propagating seedless fruit producing plants according to the invention disclosed herein are used for producing a plant according to the invention.

A further embodiment of the invention concerns propagation material of plants according to the invention, and/or propagation material of plants comprising plant cells according to the invention or propagation material of plants obtainable/obtained by a method according to the invention for production of a plant or propagation material of plants obtainable/obtained by a method according to the invention comprising introducing a foreign nucleic acid molecule into a plant cell or propagation material of plants obtainable/obtained from a plant optionally obtainable by a method for propagating seedless fruit producing plants according to the invention. A specific comprised embodiment of the invention is propagation material of plants obtainable/obtained from seeds deposited under accession number NCIMB 43064, preferably propagation material of plants obtainable/obtained from seeds deposited under accession number NCIMB 43064 being heterozygous or homozygous for the mutant allele of a Emb2 protein-encoding gene. Also comprised by the invention is propagation material of plants heterozygous or homozygous for a mutant allele of a Emb2 protein-encoding gene, wherein the propagation material is obtained/obtainable from plants originating from a crossing of a plant obtained from seeds of deposit accession number NCIMB 43064 with another plant.

Here, the term "propagation material" comprises those components of the plant which are suitable for generating progeny via the vegetative (agamic) or generative (gamic, sexual) route. Suitable for vegetative propagation are, for example, cuttings, in vitro tissue, cell, protoplast, embryo or callus cultures, micropropagation methods, rhizomes or tubers. Other propagation material includes, for example, fruits, seeds, seedling, being heterozygous or homozygous for a mutant allele of a Emb2 protein encoding gene etc. The propagation material in one aspect takes the form of cuttings which are propagated by grafting to another rootstock or in vitro tissue culture material, in particular embryo cultures. In particular preferred is propagation material in the form of in vitro tissue culture material, particularly in vitro embryo cultures.

A further embodiment of the invention concerns parts of plants according to the invention, and/or parts of plants comprising plant cells according to the invention or parts of plants obtainable/obtained by a method according to the invention for production of a plant or parts of plants obtainable/obtained by a method according to the invention comprising introducing a foreign nucleic acid molecule into a plant cell or parts of plants obtainable/obtained from a plant optionally obtainable by a method for propagating seedless fruit producing plants according to the invention. A further comprised embodiment of the invention concerns parts of plants obtainable/obtained from seeds deposited under accession number NCIMB 43064 (or from progeny thereof), preferably plant parts of plants obtainable/obtained from seeds deposited under accession number NCIMB 43064 (or from progeny thereof) being heterozygous or homozygous for the mutant allele of a Emb2 protein-encoding gene. Also comprised by the invention are plant parts of plants heterozygous or homozygous for a mutant allele of a Emb2 protein encoding gene, wherein the plant parts are obtained/obtainable from plants originating from a crossing of a plant obtained from seeds of deposit accession number NCIMB 43064 with another plant.

A further embodiment of the invention concerns a method for production of a seedless fruit comprising growing a plant according to the invention and/or growing a plant comprising plant cells according to the invention, or growing a plant obtainable/obtained by a method for production of a plant according to the invention, or growing fruits of plants obtainable/obtained by a method according to the invention comprising introducing a foreign nucleic acid molecule into a plant cell, or growing a plant obtainable/obtained from a plant optionally obtained/obtainable by method for propagating seedless fruit producing plants according to the invention, in a field or in a greenhouse (e.g. a glasshouse, tunnel or net-house), allowing the plant to be pollinated and harvesting the seedless fruit. Preferably the plant grown in the method for producing seedless fruits according to the invention is homozygous for a mutant allele of a Emb2 protein encoding gene.

It has been found that pollination of plants comprising a mutant allele of a Emb2 protein encoding gene in homozygous state with pollen from a different plant will result in the plant to produce seedless fruits.

It is not decisive if the stigma of a plant being homozygous for a mutant allele of a Emb2 protein encoding gene is pollinated by pollen comprising a mutant allele of a Emb2 protein encoding gene or by pollen comprising a wild type allele of a Emb2 protein encoding gene. In any case, independent of the genotype of the pollen, the female plant being homozygous for a mutant allele of a Emb2 protein encoding gene will produce seedless fruits. Even when cross-pollinated by pollen from wild type plants, plants according to the invention being homozygous for a mutant allele of a Emb2 protein encoding gene will produce seedless fruits. Thus, when cultivating plants according to the invention, in any case seedless fruits will be obtained.

"Greenhouse" shall be understood in connection with the present invention to mean a building or compartment used for growing plants which has a roof and walls of transparent material consisting of glass, plastic, polyethylene, gaze, netting or the like. Greenhouses may have or not have further technical equipment for heating, cooling, shading, automatic watering, fertilisation, carbon dioxide concentration adjustment etc. Greenhouses with any type of technical equipment shall be comprised by the term "greenhouse" as used herein.

Another embodiment of the invention concerns fruits of, or obtainable/obtained from, plants according to the invention, and/or fruits comprising plant cells according to the invention or fruits of plants obtainable/obtained by a method according to the invention for production of a plant, or fruits of plants obtainable/obtained by a method according to the invention comprising introducing a foreign nucleic acid molecule into a plant cell, or fruits of plants obtainable/obtained from a plant obtained/obtainable by a method according to the invention for propagating seedless fruit producing plants, or a fruit obtainable/obtained by a method according to the invention for production of a seedless fruit. A further comprised embodiment of the invention concerns fruits of plants obtainable/obtained from seeds deposited under accession number NCIMB 43064 (or progeny thereof), preferably fruits of plants obtainable/obtained from seeds deposited under accession number NCIMB 43064 (or progeny thereof) being heterozygous or homozygous for the mutant allele of a Emb2 protein-encoding gene. Also comprised by the invention are fruits heterozygous or homozygous for a mutant allele of a Emb2 protein encoding gene, wherein the fruits are obtained/obtainable from plants originating from a crossing of a plant obtained from seeds of deposit accession number NCIMB 43064 with another plant. The fruits can be heterozygous for a mutant allele of a Emb2 protein encoding gene and produce seed bearing fruits or can be homozygous for an allele of a Emb2 protein encoding gene and produce seedless fruits. Fruits being heterozygous for an allele of a Emb2 protein encoding gene can be used for propagating plants comprising a mutant allele of a Emb2 protein encoding gene. Preferably, the fruits according to the invention are homozygous for a mutant allele of a Emb2 protein encoding gene and/or produce seedless fruits. Seedless fruits for logical reasons are not eligible for growing further plants from these fruits. Therefore, one embodiment of the invention concerns fruit according to the invention which is a seedless fruit which is not eligible for propagation or which cannot propagate or which is a non-propagating.

When reference herein is made to plants, plant parts obtainable/obtained from seed deposited under accession number NCIMB 43064 or progeny thereof, it is understood that reference to the mutant emb2 allele present in the material is made and that a de novo generation in any other watermelon material of the same mutant as present in this material is equally an embodiment of the invention.

A further embodiment of the invention concerns the use of a nucleic acid molecule encoding a Emb2 protein selected from the group consisting of
  a) Nucleic acid molecules, which encode a protein with the amino acid sequence given under SEQ ID NO: 1 or SEQ ID NO: 4 or SEQ ID NO: 5 or SEQ ID NO: 9 or SEQ ID NO:10 or SEQ ID NO: 11,
  b) Nucleic acid molecules, which encode a protein, the sequence of which has an identity of at least 70%, 75%, more preferably at least 80%, even further preferred at least 90% or particularly preferred at least 95% with the amino acid sequence given under SEQ ID NO: 1 or SEQ ID NO: 4 or SEQ ID NO: 5 or SEQ ID NO: 9 or SEQ ID NO:10 or SEQ ID NO: 11;
  c) Nucleic acid molecules, which comprise the nucleotide sequence shown under SEQ ID NO: 2 or SEQ ID NO: 3 or a complimentary sequence;
  d) Nucleic acid molecules, which have an identity of at least 70%, 75%, more preferably at least 80%, even further preferred at least 90% or particularly preferred at least 95% with the nucleic acid sequences described under c);
  e) Nucleic acid molecules, which hybridize with at least one strand of the nucleic acid molecules described under a), b), c), or d) under stringent conditions;
  f) Nucleic acid molecules, the nucleotide sequence of which deviates from the sequence of the nucleic acid molecules identified under a) or b) due to the degeneration of the genetic code; and
  g) Nucleic acid molecules, which represent fragments, allelic variants and/or derivatives of the nucleic acid molecules identified under a), b), c) or d)
for the production of a plant producing seedless fruits.

In a preferred embodiment of the use of a nucleic acid molecule encoding a Emb2 protein, the nucleic acid molecule encoding a Emb2 protein is used for the production of plants according to the invention, in a particular preferred embodiment, the use of a nucleic acid molecule encoding a Emb2 protein is used for production of plants producing seedless fruits according to the invention.

In another preferred embodiments, a nucleic acid molecule encoding a Emb2 protein is used for the production of a plant part according to the invention or a fruit according to the invention.

In a further preferred embodiment a nucleic acid molecule encoding a Emb2 protein, is used in any of the methods of the invention disclosed herein. The nucleic acid molecules encoding a Emb2 protein can e.g. be used in a method according to the invention for production of a plant or in a method according to the invention comprising introducing a foreign nucleic acid molecule into a plant cell or in a method according to the invention for propagating seedless fruit producing plants according to the invention or in a method according to the invention for production of a seedless fruit.

In another preferred embodiment, a nucleic acid molecule encoding a Emb2 protein is used for identifying if a plant cell or plant comprises a mutant allele of a Emb2 protein encoding gene or if a plant cell or plant synthesises a mutant mRNA encoding a Emb2 protein or if a plant cell or plant has a decreased activity of a Emb2 protein. Preferably the nucleic acid molecule encoding a Emb2 protein is used for identifying if a seedless fruit producing plant comprises a mutant allele of a Emb2 protein encoding gene or if a plant synthesises a mutant mRNA encoding a Emb2 protein or if a plant has a decreased activity of a Emb2 protein. How such plants can be identified has been described herein above and is applicable hereto accordingly.

Preferred embodiments concerning nucleic acid molecules encoding Emb2 proteins have been described herein above and are applicable for the uses according to the invention accordingly.

In one aspect a screening method for identifying and/or selecting seeds, plants or plant parts or DNA from such seeds, plants or plant parts comprising in their genome a mutant allele of a Emb2 protein-encoding gene is provided.

The method comprises screening at the DNA, RNA (or cDNA) or protein level using known methods, in order to detect the presence of the mutant allele. There are many methods to detect the presence of a mutant allele of a gene.

For example if there is a single nucleotide difference (single nucleotide polymorphism, SNP) between the wild type and the mutant allele, a SNP genotyping assay can be used to detect whether a plant or plant part or cell comprises the wild type nucleotide or the mutant nucleotide in its genome. For example the SNP can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP-assay method.

Equally other genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

Genotyping of diploid plants or plant parts (cells, leaves, DNA, etc.) can distinguish SNP genotypes, e.g. plants or parts comprising GG for nucleotide 3331 of SEQ ID NO: 3 or of SEQ ID NO: 8 (i.e. if two Guanines are present at this nucleotide the plant genome is homozygous for the wild type nucleotide) can be distinguished from plants or parts comprising AG for nucleotide 3331 of SEQ ID NO: 3 or of SEQ ID NO: 8 (heterozygous for the mutant nucleotide) in their genome and can be distinguished from plants or plant parts comprising AA for nucleotide 3331 of SEQ ID NO: 3 or of SEQ ID NO: 8 (homozygous for the mutant nucleotide) in their genome. This would be one SNP genotyping assay to determine whether a watermelon plant or plant part comprises the specific mutant allele of SEQ ID NO: 3 in its genome. But similar assays can easily be developed for other mutant alleles, e.g. comprising one or more nucleotides inserted, deleted or replaced compared to the wild type allele.

Thus, dependent on the nature of the mutation, a genotyping assay can be developed to differentiation between plants or plant parts carrying at least one copy of the mutant allele and plants or plant parts carrying the wild type allele.

Genotyping of tetraploid plants or plant parts (cells, leaves, DNA, etc.) can be done in the same way as for diploids, using for example a KASP-assay to distinguish SNP genotypes, e.g. plants or parts comprising GGGG for nucleotide 3331 of SEQ ID NO: 3 or SEQ ID NO: 8 (homozygous for the wild type nucleotide) can be distinguished from plants or parts comprising other genotypes for the SNP, e.g. GGGA, GGAA, etc. in their genome. The same applies for triploids. The same also applies for other polyploids.

In a preferred aspect the above methods, plants, plant cells and plant parts which comprise at least one copy of a mutant allele of a Emb2 protein-encoding gene, are watermelon plants, especially cultivated watermelon, e.g. diploid, tetraploid or triploid cultivated watermelon.

The watermelon plants may be breeding lines or varieties. The mutant allele of a Emb2 protein encoding gene may be generated in, or introduced into (e.g. from seeds deposited under NCIMB 43064 or progeny thereof), any cultivated watermelon to produce lines or varieties comprising the mutant allele of the Emb2 protein, preferably in homozygous form. Cultivated watermelons produce diverse fruit sizes (e.g. very small, as described in WO2012069539, e.g. less than 0.9 kg or even equal to or less than 0.65 kg; personal-size of about 3-7 pounds, i.e. about 1.4 to 3.2 kg; icebox sizes of about 6-12 pounds, i.e. about 2.7 to 5.5 kg; and larger sizes of up to 35 pounds, i.e. about 15.9 kg), fruit flesh colors, and fruit shapes and with different rind colors. The mutant allele may, therefore, be introduced into cultivated watermelon producing any fruit shape (e.g. elongate, oval, oval elongated, blocky, blocky elongated, spherical or round), fruit surface (e.g. furrow, smooth), flesh color (e.g. red, dark red, scarlet red, coral red, orange, salmon or pink, yellow, canary yellow or white), rind color (e.g. light green; dark green; green-striped with narrow, medium or wide stripes; grey types; with or without spotting; Golden yellow; Crimson type rind, Jubilee type rind; Allsweet type rind; black/dark green), rind thickness, rind toughness, rind pattern (e.g. striped, non-striped, netted), flesh structure/flesh firmness, lycopene and/or vitamin content, different sugar to acid ratios, very good fruit flavour, etc. by breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavour, high vitamin and lycopene content, firm flesh texture, non-fibrous flesh texture, freedom from defects such as hollow heart, rind necrosis, blossom-end rot or cross stitch and good rind characteristics and cracking-resistance). The fruits produced by the line or variety are preferably marketable fruits. In one aspect the average brix is at least 6.0, 7.0, 8.0 or at least 9.0, preferably at least 10.0, more preferably at least 11.0 or more.

Fruit color may be any color, such as red, dark red, scarlet red, coral red, orange, salmon, pink, pinkish red, yellow, canary yellow or white. Preferably the fruit flesh color is uniform.

In one aspect, a method for identifying a plant or plant part or cell comprising in its genome at least one copy of a mutant allele of Emb2 gene is provided, said method comprising determining whether the plant or plant part or cell comprises in its genome at least one mutant emb2 allele.

This method may involve analysing (directly or indirectly) the gene expression of the emb2 allele, and/or the genomic nucleotide sequence of the emb2 allele, or the mRNA nucleotide sequence of the emb2 allele, or the protein sequence of the Emb2 protein, or the protein amounts of the Emb2 protein of the plant or plant part or plant cell, to determine if the gene expression is knocked down or knocked out compared to the wild type plant or plant part or plant cell, or if the encoded protein comprises one or more amino acid insertions, deletions or replacements compared to the wild type Emb2 protein.

One method for analysing the presence of a mutant emb2 allele, is for example to assay the presence of a Single Nucleotide Polymorphism (SNP) in the genomic sequence of the emb2 allele, by, for example, designing primers for the SNP and genotyping plants or plant parts for the genotype of that particular SNP. For example, in the Examples a KASP assay for the Single Nucleotide Polymorphism (the Guanine, G, or Adenine, A, nucleotide) at nucleotide 3331 of SEQ ID NO: 3 or SEQ ID NO: 8 is provided.

So one aspect of the invention comprises a method for determining whether a plant, plant part or plant cell comprises one or more copies of a mutant emb2 allele by a method selected from analysing one or more nucleotides of the genomic emb2 allele in a genotyping assay, analysing the mRNA (or cDNA) expressed by the emb2 allele or analysing the Emb2 protein amount and/or amino acid sequence (using e.g., antibody based detection).

In one aspect, especially in respect of the European Patent Convention, the plant according to the invention is "not obtained exclusively by an essentially biological process", or in one aspect the mutant emb2 allele is not a natural mutant allele. If such a disclaimer is present in the claim of the European patent, it should be noted that using a plant comprising a mutant allele (e.g. a commercial variety of the applicant) to cross the mutant allele into a different background will still be seen as falling under the claim, even though an exclusively essentially biological process (only crossing and selection) may have been used to transfer the allele into a different background.

In one aspect the mutant emb2 allele is an induced mutant allele; in another aspect the mutant emb2 allele is a natural mutant allele as defined herein, introgressed into a cultivated plant, e.g. into cultivated watermelon. Thus, in one aspect the cultivated plant comprises a recombinant chromosome, comprising the natural mutant emb2 allele.

In one embodiment of the invention a non-destructive seed based genotyping method is used to determine the presence of one or more mutant emb2 alleles in the plant or plant part, especially a non-destructive genotyping of single plant seeds, whereby the viability of the seed is not affected, but the genotype of the plant that grows from the seed can be determined. Various non-destructive single seed genotyping methods have been developed and can be used. For example Meru et al. (2013, Genetics and Molecular Research 12 (1): 702-709, "A non-destructive genotyping system from a single seed for marker-assisted selection in watermelon") describes such a method.

In another aspect the seeds may be germinated to select plants which are homozygous for the emb2 mutant allele. This method is useful for mutant emb2 alleles which are associated with a semi-glabrous phenotype when the allele is present in homozygous form. In one aspect, this method can be applied to the mutant allele as present in the deposited seeds or derivable from the deposited seeds or as optionally generated de novo in another watermelon plant. However, this method may equally be applicable to other mutant emb2 alleles and other crops species, wherein the mutant emb2 allele is found to be associated with a semi-glabrous phenotype when it is in homozygous form.

Thus, in one aspect a method for selecting a plant which comprises the mutant emb2 allele in homozygous form is provided, comprising selecting plants, e.g. seedlings, comprising a semi-glabrous phenotype on the stems.

This method may comprise the steps of providing a plurality of seeds, e.g. seeds comprising different genotypes for the mutant (emb2) and wild type (Emb2) allele, e.g. seeds comprising mixtures of genotypes, such as emb2/Emb2 (heterozygous for the mutant allele) and emb2/emb2 (homozygous for the mutant allele), and germinating the seeds so that the plants comprising the semi-glabrous phenotype on the stem can be selected.

Other seedlings, having a normal hairy stem can be discarded. The selected seedlings can then be used for stenospermocarpic seedless fruit production, e.g. planted into a production field. Optionally, cotyledon or leaf samples (or other tissue samples) can be taken and a genotyping assay can be carried out to verify the homozygous present of the mutant emb2 allele in the selected seedlings or plants. If desired, control seeds and seedlings can be included in the method at any step, such as homozygous wild type (Emb2/Emb2) seeds/plants, or progeny of seeds deposited under NCIMB 43064.

In one embodiment of the invention, the population of seeds comprising a mixture of genotypes of Emb2 alleles is a population of seeds comprising about 50% of seeds wherein the mutant emb2 allele is in heterozygous form (emb2/Emb2) and about 50% of seeds wherein the mutant emb2 allele is in homozygous form (emb2/emb2). A population of seeds which segregates in a 50% emb2/Emb2 to 50% emb2/emb2 ratio can be generated by crossing a parent line A (preferably as female parent), which is heterozygous for the mutant emb2 allele, with a parent line B (preferably as male parent), which is homozygous for the mutant emb2 allele. Seeds harvested from this cross will segregate in the approximate 50:50 ratio mentioned and from this population of seeds the approximately 50% homozygous mutant emb2 allele seeds can be selected as described. It is understood that the cross of parent line A with parent line B can be carried out between many plants to obtain a large amount of F1 seeds which segregate in the approximate 50:50 ratio of Emb2/emb2:emb2/emb2 seeds.

The actual step of crossing line A with line B is, in one aspect of the invention, also part of the method. Thus, in one aspect a method of generating and/or selecting seeds which are homozygous for the mutant emb2 allele is provided, comprising a) Crossing a parent line A, which is heterozygous for a mutant emb2 allele of the invention with parent line B, which is homozygous for a mutant emb2 allele of the invention, b) Harvesting the F1 seeds of the cross, c) Germinating the F1 seeds d) Selecting plants of step c) which comprise the emb2 allele in homozygous form, preferably by phenotypic selection of semi-glabrous plants, and optionally e) Allowing the selected plants to produce seedless fruits (after pollination of the flowers), and optionally f) Harvesting the seedless fruits.

As mentioned, parent line A is the female parent line and parent line B is the male parent line in this method, because the line homozygous for the mutant emb2 allele cannot be used to produce seeds, as it will produce seedless fruits upon pollination of the flowers.

Another aspect of the invention the population of seeds comprising a mixture of genotypes of Emb2 alleles is a population of seeds comprising about 50% of seeds wherein the mutant emb2 allele is in heterozygous form (emb2/Emb2) and about 25% of seeds wherein the mutant emb2 allele is in homozygous form (emb2/emb2) and about 25% wherein the wild type Emb2 allele is in homozygous form (Emb2/Emb2). A population of seeds which segregates in a 50% emb2/Emb2 to 25% emb2/emb2 to 25% Emb2/Emb2 ratio can be generated by crossing a parent line A, which is heterozygous for the mutant emb2 allele, with a parent line B, which is also heterozygous for the mutant emb2 allele, or by selfing a plant which is heterozygous for the mutant emb2 allele. Seeds harvested from this cross will segregate in the approximate 50 (Emb2/emb2):25 (emb2/emb2):25 (Emb2/Emb2) ratio mentioned and from this population of seeds the approximately 25% homozygous mutant emb2 allele seeds can be selected as described.

The actual step of crossing heterozygous line A with heterozygous line B, or selfing a line which is heterozygous for the mutant emb2 allele is, in one aspect of the invention, also part of the method. Thus, in one aspect a method of generating and/or selecting seeds which are homozygous for the mutant emb2 allele is provided, comprising a) Crossing a parent line A, which is heterozygous for a mutant emb2 allele of the invention with parent line B, which is heterozygous for a mutant emb2 allele of the invention, or selfing a line which is heterozygous for a mutant emb2 allele of the invention, b) Harvesting the F1 seeds of the cross, c) Germinating the F1 seeds d) Selecting plants of step c) which comprise the emb2 allele in homozygous form, preferably by phenotypic selection of semi-glabrous plants, and optionally e) Allowing the selected plants to produce seedless fruits (after pollination of the flowers), and optionally f) Harvesting the seedless fruits.

Also provided is a method for producing stenospermocarpic fruits, said method comprising growing a plant comprising a mutant emb2 allele (as described throughout the specification) in homozygous form and optionally harvesting the seedless fruits produced by said plant.

Further aspects of the invention are a method for selecting a plant or plant part of the family Cucurbitaceae (e.g. watermelon, cucumber, melon, or other species) or Solanaceae (e.g. tomato, pepper, or other species) capable of stenospermocarpic fruit formation, said method comprising selecting a plant or plant part comprising at least one copy of a mutant emb2 allele, wherein the mutant allele causes stenospermocarpic fruit formation when the allele is in homozygous form. The selection of the plant or plant part may involve direct and/or indirect methods, such as DNA analysis of the endogenous Emb2 alleles (e.g. sequence analysis, allele specific genotyping methods, etc.), RNA analysis of the Emb2 alleles (e.g. mRNA expression), Emb2 protein analysis, etc. Thus, in the above methods any phenotypic selection step on germinated seedlings can be replaced by selection based on the detection of the mutant emb2 allele in either the non-germinated seeds (i.e. omitting the germination of seeds step) and/or in seedlings or plants (or tissue thereof, such as leaf discs) of germinated seeds.

In a further aspect of the invention a method for generating a plant or plant part of the family Cucurbitaceae (e.g. watermelon, cucumber, melon, or other species) or Solanaceae (e.g. tomato, pepper, or other species) capable of stenospermocarpic fruit formation, said method comprising contacting a plant or plant part with a mutagen and subsequently (optionally after one or more selfings of the mutagenized plant) selecting a plant or plant part comprising at least one copy of a mutant emb2 allele, wherein the mutant allele causes stenospermocarpic fruit formation when the allele is in homozygous form.

Also provided is a method for producing a plant of the family Cucurbitaceae (e.g. watermelon, cucumber, melon, or other species) or Solanaceae (e.g. tomato, pepper, or other species) capable of stenospermocarpic fruit formation, comprising
  a) Crossing a plant comprising in its genome at least one mutant emb2 allele as described (which mutant emb2 allele causes stenospermocarpic fruit formation when in homozygous form) with another plant, and optionally
  b) Harvesting seeds from said cross, and optionally
  c) Selecting seeds, or plants grown from the seeds (e.g. seedlings), comprising at least one copy of the mutant emb2 allele, preferably selecting seeds comprising two copies of the mutant emb2 allele.

In a preferred aspect, a plant which is heterozygous for the mutant emb2 allele is used as female parent and is crossed with a male parent plant which is homozygous for the mutant emb2 allele.

The selection in step c) can be based on method which detect the mutant emb2 allele directly (e.g. using a genotyping assay) or indirectly, and/or detection of the semi-glabrous phenotype described.

Also the seeds and plants selected by the method are encompassed herein, as are plants grown from the seeds and seedless fruits produced by the plants grown from the seeds homozygous for the mutant emb2 allele.

It is understood that in the herein described methods any plant species, comprising any of the described mutant emb2 alleles, which in homozygous form lead to seedless fruit formation, can be used. The invention is not limited to watermelon and also not to the specific mutant allele generated in the seeds deposited under accession number NCIMB43064, because the skilled person can, based on the herein provided information, generate various mutants in the Emb2 gene of any plant species and determine that the mutant leads to the expected stenospermocarpy when in homozygous form.

Deposit Information

Diploid *Citrullus lanatus* seeds of plants segregating for a mutant allele of a Emb2 protein-encoding gene have been deposited by Nunhems B.V. under the Budapest Treaty under accession No. NCIMB 43065 at NCIMB Ltd., Ferguson Building, Craibstone Estate, Bucksburn, Aberdeen AB21 9YA, Scotland on 31 May 2018.

The deposited seeds were obtained from a self-pollinated back-cross of a plant homozygous for the emb2 mutant allele with plants homozygous for the Emb2 wild type allele. Therefore 25% of the deposited seeds are homozygous for the emb2 mutant allele and produce seedless fruits, 50% are heterozygous for the mutant allele and 25% are homozygous for the wild type allele, encoding the wild type Emb2 protein.

Access to the deposits will be available during the pendency of this application to persons determined by the Commissioner of Patent and Trademarks to be entitled thereto upon request.

Subject to 37 C.F.R. § 1.808(b), all restrictions imposed by the depositor on the availability to the public of one or more deposits will be irrevocably removed upon the granting of the patent by affording access to the deposits. The deposits will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Sequence Description

SEQ ID NO 1: Mutant Emb2 protein of *Citrullus lanatus*, comprising an Arginine (Arg) at amino acid 202, instead of a Glycine (Gly) in the wild type Emb2 protein of SEQ ID NO: 6. TMD1 is from amino acid 76 to 339. NBD1 is from amino acid 391 to 629. Then there is a linker domain from amino acid 630 to 708. TMD2 is from amino acid 709 to 978 and NBD2 from amino acid 1025 to 1260.

SEQ ID NO 2: coding DNA (cDNA), which encodes the mutant protein of SEQ ID NO 1. It comprises a Adenine at nucleotide 604, instead of a Guanine, whereby the codon is changed into agg (encoding Arginine) instead of the wild type ggg (encoding Glycine).

SEQ ID NO 3: genomic DNA, which encodes the mutant protein of SEQ ID NO: 1. It comprises a Adenine at nucleotide 3331, instead of a Guanine, whereby the codon is changed to agg (encoding Arginine) instead of the wild type ggg (encoding Glycine).

SEQ ID NO 4: Amino acid sequence of a *Cucumis sativus* (cucumber) wild type Emb2 protein. TMD1 is from amino acid 79 to 342. NBD1 is from amino acid 394 to 632. Then there is a linker domain from amino acid 633 to 711. TMD2 is from amino acid 712 to 981. And NBD2 is from amino acid 1028 to 1263.

SEQ ID NO 5: Amino acid sequence of a *Cucumis melo* (melon) wild type Emb2 protein. TMD1 is from amino acid 44 to 307. NBD1 is from amino acid 359 to 597. Then there is a linker domain from amino acid 598 to 676. TMD2 is from amino acid 677 to 946. And NBD2 is from amino acid 993 to 1228.

SEQ ID NO 6: Wild type (functional) Emb2 protein of *Citrullus lanatus*.

SEQ ID NO 7: coding DNA (cDNA), which encodes the wild type Emb2 protein of SEQ ID NO:6.

SEQ ID NO 8: genomic DNA, which encodes the wild type protein of SEQ ID NO: 6.

SEQ ID NO 9: Amino acid sequence of a *Solanum lycopersicon* (tomato) wild type Emb2 protein. TMD1 is from amino acid 64 to 327. NBD1 is from amino acid 379 to 617. Then there is a linker domain from amino acid 618 to 697. TMD2 is from amino acid 698 to 967. And NBD2 is from amino acid 1014 to 1249.

SEQ ID NO 10: Amino acid sequence of a *Capsicum annuum* (pepper) wild type Emb2 protein. TMD1 is from amino acid 61 to 324. NBD1 is from amino acid 376 to 614. Then there is a linker domain from amino acid 615 to 691. TMD2 is from amino acid 692 to 961. And NBD2 is from amino acid 1008 to 1243.

SEQ ID NO 11: Amino acid sequence of a *Capsicum annuum* (pepper) wild type Emb2 protein. TMD1 is from amino acid 61 to 324. NBD1 is from amino acid 376 to 614. Then there is a linker domain from amino acid 615 to 691. TMD2 is from amino acid 692 to 961. And NBD2 is from amino acid 1008 to 1243.

SEQ ID NO 12: alpha helix domain in the TMD1 domain of the watermelon Emb2 protein of SEQ ID NO: 6

SEQ ID NO 13: alpha helix domain in the TMD1 domain of the tomato Emb2 protein of SEQ ID NO: 9

SEQ ID NO 14: primer FAM allele of KASP assay for emb2 allele

SEQ ID NO 15: primer VIC allele of KASP assay for emb2 allele

SEQ ID NO 16: Common primer of KASP assay for emb2 allele

DESCRIPTION OF THE FIGURES

FIG. 1 Sequence alignment of Cucurbitaceae Emb2 proteins, namely SEQ ID NO: 1 (mutant Emb2 protein of watermelon) and SEQ ID NO: 4 (wild type Emb2 protein of cucumber) and SEQ ID NO: 5 (wild type Emb2 protein of melon). The conserved domains TMD1-NBD1-TMD2-NBD2 are indicated in grey background shading for the watermelon sequence. The alpha-helix domain of TMD1 comprising the Arginine (R) of the mutant watermelon Emb2 protein is indicated by a box and the R is in bold. The equivalent amino acid in the cucumber and melon sequence is also in bold (G).

FIG. 2 A. Shows hairy stems of wild type (WT) watermelon seedlings on the left and semi-glabrous stems of a mutant watermelon seedling, comprising the mutant emb2 allele in homozygous form. B. Shows the non-viable seeds of a 'seedless fruit' produced by a watermelon plant comprising the mutant emb2 allele in homozygous form (labelled EMB2), and wild type (WT) seeds produced by a watermelon plant comprising the wild type Emb2 allele in homozygous form.

FIG. 3 Sequence alignment of Solanaceae Emb2 proteins together with the mutant watermelon Emb2 protein of SEQ ID NO: 1, depicting SEQ ID NO: 9 (wild type Emb2 protein of tomato) and SEQ ID NO: 10 and 11 (wild type Emb2 proteins of pepper). The conserved domains TMD1-NBD1-TMD2-NBD2 are indicated in grey background shading for the watermelon sequence. The alpha-helix domain of TMD1 comprising the Arginine (R) of the mutant watermelon Emb2 protein is indicated by a box and the R is in bold. The equivalent amino acid in the tomato and pepper sequences is also in bold (G).

GENERAL DEFINITIONS

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells, plants, etc. Similarly, "a fruit" or "a plant" also refers to a plurality of fruits and plants.

A "plant line" or "breeding line" refers to a plant and its progeny. As used herein, the term "inbred line" refers to a plant line which has been repeatedly selfed, as a result of this selfing, plants of an inbred line are nearly identical to each other in genotype and phenotype.

As used herein, the term "mutant allele of a gene" refers to a mutant allele of a gene, said mutant allele either encodes a protein which, compared to the protein encoded by the wild type allele of the gene, comprises one or more amino acids replaced, deleted or inserted, whereby the mutant allele produces a mutant protein which has a "reduced-function" or "loss-of-function", or said mutant allele of the gene has a reduced gene expression or even no expression compared to the gene expression of the wild type (non-mutated) allele of the gene.

As used herein, the term "plant" includes the whole plant or any parts or derivatives thereof, preferably having the same genetic makeup as the plant from which it is obtained, such as plant organs (e.g. harvested or non-harvested fruits, leaves, etc.), plant cells, plant protoplasts, plant cell- or tissue-cultures from which whole plants can be regenerated, plant calli, plant cell clumps, plant transplants, seeds from which the plant can be grown and seeds produced by the plant, seedlings, plant cells that are intact in plants, plant clones or micropropagations, or parts of plants, such as plant cuttings, embryos, pollen, ovules, fruits (e.g. harvested tissues or organs), flowers, leaves, clonally propagated plants, roots, stems, root tips, grafts (scions and/or root stocks) and the like. Also any developmental stage is included, such as seedlings, cuttings prior or after rooting, etc. As used herein, the term plant includes plant and plant parts comprising one or more of the mutant alleles of the invention.

In one aspect, the term plant part refers to plant cells, or plant tissues or plant organs that comprise one or more of the mutant alleles of the invention. In one aspect a plant part can grow into a plant and/or live on photosynthesis (i.e. synthesizing carbohydrate and protein from the inorganic substance, such as water, carbon dioxide and mineral salt). In another aspect, a plant part cannot grow into a plant and/or live on photosynthesis (i.e. synthesizing carbohydrate and protein from the inorganic substance, such as water, carbon dioxide and mineral salt). Thus, a plant part can be propagating or non-propagating.

As used herein, the term "variety" or "cultivar" or "plant variety" means a plant grouping within a single botanical taxon of the lowest known rank, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one locus or gene, but which can otherwise differ from one another enormously as regards the other loci or genes.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found.

"Diploid plant" refers to a plant, vegetative plant part(s), or seed from which a diploid plant can be grown, having two sets of chromosome, designated herein as 2n.

"Vegetative propagation" refers to propagation of plants from vegetative tissue, e.g. by in vitro propagation or grafting methods (using scions).

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA or an RNAi molecule) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. A gene may be an endogenous gene (in the species of origin) or a chimeric gene (e.g. a transgene or cis-gene).

"Expression of a gene" refers to the process wherein a DNA region, which is operably linked to appropriate regulatory regions, particularly a promoter, is transcribed into an RNA.

An "active protein" or "functional protein" is a protein which has protein activity as measurable in vivo, e.g. by the phenotype conferred by the protein. A "wild type" protein is a fully functional protein, as present in the wild type plant. A "mutant protein" is herein a protein comprising one or more mutations in the nucleic acid sequence encoding the protein, whereby the mutation(s) results in (the mutant allele encoding) a "reduced-function" or "loss-of-function" protein, as e.g. measurable in vivo, e.g. by the phenotype conferred by the mutant allele (in homozygous form).

"Induced mutant alleles" are mutant alleles in which the mutation(s) is/are/have been induced by human intervention, e.g. by mutagenesis via physical or chemical mutagenesis methods, or via e.g. tissue culture (as described in e.g. Zhang et al, Plos 9(5) e96879), including also genome editing techniques.

"Natural mutant alleles" are mutant alleles in which the mutation(s) have evolved in wild plants or wild relatives of a species or landraces. Such natural mutant alleles can be introgressed into cultivated plants by crossing and selection. For example an allele comprising a transposable element (TE) insertion is a natural mutant allele, or an allele encoding a truncated protein compared to the wild type protein may be a natural mutant allele.

A "mutation" in a nucleic acid molecule coding for a protein is a change of one or more nucleotides compared to the wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A mutation in a regulatory sequence, e.g. in a promoter of a gene, is a change of one or more nucleotides compared to the wild type sequence, e.g. by replacement, deletion or insertion of one or more nucleotides, leading for example to reduced or no mRNA transcript of the gene being made. In one aspect a mutation in a regulatory sequence of a protein includes a lower level of wild type protein (e.g. due to a lower expression of the allele) or no wild type protein being made (no expression of the allele). Mutations in regulatory elements, such as promoters, can be generated by e.g. CRISPR/Cas. Rodriguez-Leal et al., 2017, Cell 171, 470-480 describe for example mutating cis-regulatory elements to create a continuum of mutant alleles with different expression.

A "mutation" in a protein is a change of one or more amino acid residues compared to the wild type sequence, e.g. by replacement, deletion or insertion of one or more amino acid residues.

"Silencing" refers to a down-regulation or complete inhibition of gene expression of the target gene or gene family.

A "target gene" in gene silencing approaches is the gene or gene family (or one or more specific alleles of the gene) of which the endogenous gene expression is down-regulated or completely inhibited (silenced) when a chimeric silencing gene (or 'chimeric RNAi gene') is expressed and for example produces a silencing RNA transcript (e.g. a dsRNA or hairpin RNA capable of silencing the endogenous target gene expression). In mutagenesis or targeted genome editing approaches, a target gene is the endogenous gene which is to be mutated (and/or in which mutations are selected by e.g. TILLING) or edited, leading to a change in (reduction or loss of) gene expression or a change in (reduction or loss of) function of the encoded protein.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature.

The term "heterozygous" refers to a plant or plant cell having dissimilar pairs of alleles of a gene for any hereditary characteristic. The term "homozygous" or in "homozygous form" refers to a plant or plant cell or plant part (e.g. a fruit) having identical alleles of a gene for any hereditary characteristic, e.g. a diploid plant or plant part homozygous for the mutant emb2 allele comprises two copies of the allele in its genome.

It is understood that comparisons between different plant lines involves growing a number of plants of a line (e.g. at least 8 plants, preferably at least 10 plants per line) under the same conditions as the plants of one or more control plant lines (e.g. plants comprising the wild type allele or plants having the same genetics as the line it is compared with except that the wild type allele is present in homozygous form instead of the mutant allele) and the determination of statistically significant differences between the plant lines when grown under the same environmental conditions and when treated in the same way.

"Melon plant" or "cultivated melon" or "domesticated melon" refers to plants of *Cucumis melo* L. i.e. varieties, breeding lines or cultivars, cultivated by humans and having good agronomic characteristics, especially producing edible and marketable fruits of good size and quality and uniformity; such cultivated melon plants may for example be further classified as *C. melo* var. *cantalupensis*, *C. melo* var. *inodorous* and *C. melo* var. *reticulatus*; such plants are not "wild melon" or "primitive melon" plants, i.e. plants which generally have much poorer yields and poorer agronomic characteristics than cultivated plants and are less uniform genetically and in their physiological and/or morphological characteristics. "Wild plants" or "wild melon" include for example ecotypes, landraces or wild accessions or wild relatives of a species, such as for example accessions of *Cucumis melo* ssp. *agrestis*, *C. melo* ssp. *melo*, *C. melo* ssp. *acidulous*, *C. callosus*, *C. trigonus*, *C. picrocarpus*, *Cucumis melo* var. *momordica*, or other wild melon or wild relative of melon producing e.g. fruits of poor quality and/or poor uniformity.

"Watermelon plant" or "cultivated watermelon" or "domesticated watermelon" or "*Citrullus lanatus*" refers to plants of *Citrullus lanatus* ssp. *vulgaris*, i.e. varieties, breeding lines or cultivars, cultivated by humans and having good agronomic characteristics, especially producing edible and marketable fruits of good size and quality and uniformity; such plants are not "wild watermelon" or "primitive watermelon" plants, i.e. plants which generally have much poorer yields and poorer agronomic characteristics than cultivated plants and are less uniform genetically and in their physiological and/or morphological characteristics. "Wild plants" or "wild watermelon" include for example ecotypes, landraces or wild accessions or wild relatives of a species, such as for example accessions of *Citrullus lanatus* ssp. *lanatus*, *Citrullus lanatus* ssp. *mucosospermus*, *Citrullus colocynthis*, or plants of the *citroides* group (e.g. *C. lanatus* var. *citroides*) producing e.g. fruits of poor quality and/or poor uniformity.

"Landrace(s)" refers to primitive cultivars developed in local geographic regions, which often show a high degree of genetic variation in their genome and exhibit a high degree of morphological and/or physiological variation within the landrace (e.g. large variation in fruit size, etc.), i.e. are significantly less uniform than cultivated plants. Landraces are, therefore, herein included in the group "wild" plants, which is distinct from "cultivated" plants.

"Cucumber plant" or "cultivated cucumber" or "domesticated cucumber" refers to plants of *Cucumis sativus* var. *sativus* i.e. varieties, breeding lines or cultivars, cultivated by humans and having good agronomic characteristics, especially producing edible and marketable fruits of good size and quality and uniformity; such plants are not "wild cucumber" or "primitive cucumber" plants, i.e. plants which generally have much poorer yields and poorer agronomic characteristics than cultivated plants and are less uniform genetically and in their physiological and/or morphological characteristics. "Wild plants" of "wild cucumber" include for example ecotypes, landraces or wild accessions or wild relatives of a species.

"Tomato plants" or "cultivated tomato plants" are plants of *Solanum lycopersicum*, i.e. varieties, breeding lines or cultivars of the species *Solanum lycopersicum*, cultivated by humans and having good agronomic characteristics; such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species. The so-called heirloom varieties or cultivars, i.e. open pollinated varieties or cultivars commonly grown during earlier periods in human history and often adapted to specific geographic regions, are in one aspect of the invention encompassed herein as cultivated tomato plants.

"Pepper plant" or "cultivated pepper are plants" of *Capsicum annuum*, i.e. varieties, breeding lines or cultivars of the species *Capsicum annuum*, cultivated by humans and having good agronomic characteristics; such plants are not "wild plants", i.e. plants which generally have much poorer yields and poorer agronomic characteristics than cultivated plants and e.g. grow naturally in wild populations.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

"Uniformity" or "uniform" relates to the genetic and phenotypic characteristics of a plant line or variety. Inbred lines are genetically highly uniform as they are produced by several generations of inbreeding. Likewise the F1 hybrids which are produced from crossing two such inbred lines are highly uniform in their genotypic and phenotypic characteristics and performance.

A "recombinant chromosome" refers to a chromosome having a new genetic makeup arising through crossing-over between homologous chromosomes. Herein, for example, recombinant chromosome is provided comprising an introgression fragment from a wild plant, which introgression fragment comprises a natural mutant allele.

The term "traditional breeding techniques" encompasses herein crossing, backcrossing, selfing, selection, double haploid production, embryo rescue, protoplast fusion, marker assisted selection, mutation breeding etc., all as known to the breeder (i.e. methods other than genetic modification/transformation/transgenic methods), by which, for example, a recombinant chromosome can be obtained, identified and/or transferred.

"Backcrossing" refers to a breeding method by which a (single) trait, such as a mutant allele, can be transferred from a generally (but not necessarily) inferior genetic background (e.g. a wild plant or wild relative; also referred to as "donor") into a generally (but not necessarily) superior genetic background (also referred to as "recurrent parent"), e.g. a cultivated plant. An offspring of a cross (e.g. an F1 plant obtained by crossing a donor plant with a e.g. superior genetic background plant; or an F2 plant or F3 plant, etc., obtained from selfing the F1) is e.g. "backcrossed" to the recurrent parent genetic background, e.g. to the cultivated parent. After repeated backcrossing, the trait of the donor genetic background will have been incorporated into the recurrent parent genetic background.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation. In one aspect propagation by grafting, e.g. a scion onto a rootstock, is included herein.

"Cell culture" or "tissue culture" refers to the in vitro culture of cells or tissues of a plant.

"Regeneration" refers to the development of a plant from cell culture or tissue culture or vegetative propagation.

"Non-regenerable cell" refers to a cell which cannot be regenerated into a whole plant.

EXAMPLES

Example 1—Isolation of Seedless Fruit Mutant

A mutant population was established by treating approximately 10.000 watermelon seeds from an inbred line (WMZD0048TYY, abbreviated TYY in the following) with EMS several hours and subsequently washing the seeds in streaming tap water for 30 minutes. After that the seeds were kept wet until sowing in soil. M1 Plants were grown from the mutagenized seeds, self-pollinated and the seeds (M2 generation) were harvested. Eight seeds from each of 3000 M2 families were sown grown and mutant plants producing seedless fruits were isolated. One of these mutant plants was designated EMB2. Propagation of the EMB2 mutant plant was performed by grafting cuttings of the EMB2 mutant plant to rootstock of a non-mutagenized watermelon plants.

Example 2—Confirmation of Seedless Fruit Phenotype

The EMB2 mutant was back-crossed with the original non-mutagenized watermelon TYY inbred line, using pollen from the EMB2 mutant (BC1 generation). 25% of the plants grown from the self-pollinated BC1 generation did produce seedless fruits.

Pollen from the EMB2 mutant was also used for crossing with different watermelon inbred lines for establishing a mapping population. 25% of self-pollinated plants of the mapping population produced seedless fruits.

The results from the respective back-crosses and crosses wherein pollen from the EMB2 mutant was used to fertilise other inbred lines clearly demonstrate that pollen of the EMB2 mutant is fertile.

In further crosses EMB2 mutant plants, homozygous for the emb2 mutant allele were used as female parent and pollinated with pollen from various different other lines. 100% of plants from each of these crosses produced seedless fruits.

Results obtained from the different crossings show that the emb2 mutation is due to a single recessive allele. The results also demonstrate that the seedless fruit phenotype is maintained when pollen from seed producing plants is used to fertilise EMB2 mutant plants. The seedless fruit phenotype therefore is not due to aberrant pollen of the EMB2 mutant but can be assigned to defects in embryo development.

Example 3—Identification of the Gene Causing the Seedless Fruit Phenotype

The mapping population established by pollinizing different watermelon inbred lines with pollen from the EMB2 mutant plant was analysed and a single nuclear polymorphism (SNP) was detected in the genomic sequence shown under SEQ ID NO: 3. SEQ ID NO: 3 shows the sequence of the mutant emb2 genomic DNA and SEQ ID NO: 8 shows the wild type genomic DNA.

In the mutant allele of the EMB2 mutant plant the nucleotide guanine (G) at position number 3331 in SEQ ID NO: 8 is replaced by adenine (A). The mutation was in exon 4 of the gene.

The SNP was found to be in a gene on chromosome 9, encoding an ABCB transporter protein. The mutation in the emb2 allele resulted in a single amino acid being replaced by another amino acid in the conserved Transmembrane domain 1 (TMD1) of the protein. The amino acid substitution was from a Glycine to an Arginine (Gly202Arg; or G202R). The 3D conformation of the Emb2 protein was analysed and the G202R substitution was found to be localized in an alpha-helix domain of the transmembrane domain TMD1. The protein contains two transmembrane domains (TMD1 and TMD2) and two Nucleotide Binding Domains (NBD1 and NBD2), and has the primary structure TMD1-NBD1-linker domain-TMD2-NBD2. The transmembrane domains are hybdrophobic, while the Nucleotide Binding Domains are hydrophilic. The amino acid substitution in the alpha helix domain of TMD1 likely results in a reduced protein function or loss of function of the resulting mutant Emb2 protein, compared to the wild type protein, whereby in plants homozygous for this mutant stenospermocarpy results, i.e. the fruits produce only non-viable seeds like structures (see FIG. 2B) and are therefore effectively seedless.

Seeds in which the emb2 mutant allele and the wild type Emb2 allele segregate have been deposited under accession number NCIMB43064.

Example 4—Genotyping Assay to Detect Mutant Emb2 Allele of Watermelon

A genotyping assay was developed to detect the Single Nucleotide Polymorphism at nucleotide 3331 of SEQ ID NO: 3 (mutant genomic emb2 allele). In order to screen plants for the presence of the SNP, a KASP-assay (a SNP genotyping assay or KBioscience Allele-Specific PCR genotyping—assay) was developed for the SNP at nucleotide 3331 of SEQ ID NO: 3, compared to the nucleotide 3331 of SEQ ID NO: 8 (wild type genomic Emb2 allele).

For the SNP two allele-specific forward primers (i.e. detecting either the nucleotide of the mutant emb2 allele or of the wild type Emb2 allele) and one common reverse primer was developed (all sequences are given in 5' to 3' direction).

| SNP between mutant emb2 allele (in SEQ ID NO: 3) and wild | SNP | Primer - FAM(dye) | Primer - VIC(dye) | Allele | Probe FAM | Probe VIC | Common Primer |
|---|---|---|---|---|---|---|---|

| | | | | | |
|---|---|---|---|---|---|
| | | | | | type Emb2 allele (in SEQ ID NO: 8) |
| emb2/Emb2 | A/G | GGAAGGTGACCAA GTTCATGCTCCCT CACAAATCCGAT AATAAACCC (SEQ ID NO: 14) | GAAGGTCGGA GTCAACGGATT ACCCTCACAAA TCCGATAATAA ACCT (SEQ ID NO: 15) | C T | GGGAACTTT TTGCATTAT ATAAGCCGG TT (SEQ ID NO: 16) |

Using the above primers, KASP-assays can be carried out according to standard protocols developed by KBioscience-.co.uk (see www.kbioscience.co.uk), in order to detect the presence of either the mutant emb2 or the wild type Emb2 SNP-genotype in homozygous or heterozygous form in plant DNA derived from watermelon cells or tissues. If the genotype is homozygous, only one fluorescent signal will be detected. If the genotype of the plant is heterozygous, a mixed fluorescent signal will be detected.

1000 in-house breeding lines, of which 477 were unique lines, were screened using the above KASP assay.

Among the 1000 lines, only the EMB2 plant was homozygous for Adenine at nucleotide 3331 of SEQ ID NO: 3, i.e. contained the mutant emb2 allele (of SEQ ID NO: 3) in homozygous form. In the KASP assay this is detected by the VIC Probe as 'TT' signal. All other lines were homozygous for a Guanine at nucleotide 3331 of SEQ ID NO: 8, i.e. contained the wild type Emb2 allele (of SEQ ID NO: 8) in homozygous form. In the KASP assay this is detected by the FAM probe as 'CC' signal.

| Plants tested | Signal |
|---|---|
| EMB2 (homozygous for emb2 allele) | TT |
| Backcross of EMB2 (heterozygous for emb2 allele) | CT |
| All other breeding lines | CC |

This shows that the mutation is unique in the breeding lines.

Example 5—Semi-Glabrous Phenotype Found in Homozygous Emb2 Mutants

It was found that watermelon plants which were homozygous for the mutant emb2 allele (emb2/emb2) have a semi-glabrous phenotype on the stems, as shown in FIG. 2A. The reduced hairiness linked to or resulting from the mutant emb2 allele is very useful in selecting plants which a stenospermocarpic and will produce seedless fruits upon pollination.

Example 6—Orthologous Emb2 Genes of Other Species

Based on the watermelon Emb2 gene, orthologs of this gene were identified in other crop species using BLAST® analysis. These include a cucumber Emb2 gene from cucumber cultivar 9930 (encoding the Emb2 protein of SEQ ID NO: 4), a melon Emb2 gene from a not specified melon cultivar (encoding the melon Emb2 protein of SEQ ID NO: 5), a tomato Emb2 gene from variety Heinz1706 (encoding the tomato Emb2 protein of SEQ ID NO: 9) and two pepper Emb2 genes, one from a Chinese cultivar (Zunla-1; encoding the Emb2 protein of SEQ ID NO: 10) and one from pepper cultivar CM334 (encoding the Emb2 protein of SEQ ID NO: 11).

Whether these orthologs (or other allelic variants of these genes) do also lead to stenospermocarpy when the protein has a decreased function or loss-of-function, or when the gene expression is knocked down or knocked out, can be tested by e.g. mutagenizing plants, identifying mutants in the endogenous Emb2 gene and then generating homozygous mutant plants to analyse the phenotype of these plants.

---

The invention claimed is:

1. A plant or plant part of the species *Citrullus lanatus* comprising at least one copy of a mutant allele of a gene, said gene encodes a wild type protein of SEQ ID NO: 6 or a wild type protein comprising at least 90% sequence identity to SEQ ID NO: 6, said mutant allele conferring stenospermocarpy when the mutant allele is in homozygous form, wherein said mutant allele encodes a protein comprising a decreased function or a loss of function compared to the wild type protein due to one or more amino acids being replaced, inserted or deleted in a conserved domain selected from the following domains: the Transmembrane domain 1 (TMD1) at amino acid number 76 to 339 of SEQ ID NO: 6; the Nucleotide Binding Domain 1 (NBD1) at amino acid number 391 to 629 of SEQ ID NO: 6, the Transmembrane domain 2 (TMD2) at amino acid number 709 to 978 of SEQ ID NO: 6, or the Nucleotide Binding Domain 2 (NBD2) at amino acid number 1025 to 1260 of SEQ ID NO: 6.

2. The plant or plant part according to claim 1, wherein said protein comprises one or more amino acids inserted, deleted or replaced in the alpha helix domain of SEQ ID NO: 12 or a domain comprising at least 90% amino acid identity to SEQ ID NO: 12, which is part of the TMD1 domain of the protein.

3. The plant or plant part according claim 1, wherein said mutant allele encodes a protein comprising an amino acid substitution compared to the wild type protein, whereby a Glycine or a Proline of the wild type protein is replaced by a different amino acid, wherein said Glycine or Proline is in one of the conserved domains of the protein.

4. The plant or plant part according to claim 1, wherein the mutant allele encodes a protein comprising an Arginine at amino acid 202, instead of a Glycine (Gly) in the wild type protein.

5. The plant or plant part according to claim 1, wherein said plant or plant part is diploid and is homozygous for the mutant allele.

6. A seed from which the plant or plant part according claim 1 can be grown.

7. A fruit produced by the plant according to claim 1, wherein the fruit is seedless when the plant comprises the mutant allele in homozygous form.

8. The plant part according to claim 1, wherein the plant part is a cell, a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther.

9. A vegetatively propagated plant propagated from the plant part according to claim 8.

10. A method of stenospermocarpic fruit production, said method comprising growing the plant according to claim 1, and harvesting the fruits produced by said plants.

11. A method of selecting a plant according to claim 1, which comprises the mutant allele in homozygous form, comprising selecting plants comprising a semi-glabrous phenotype on the stems and/or determining the presence of the mutant allele in the genome of the plant or seed.

* * * * *

SEQUENCE LISTING

```
<160> NUMBER OF SEQ ID NOS: 16

<210> SEQ ID NO 1
<211> LENGTH: 1269
<212> TYPE: PRT
<213> ORGANISM: Citrullus lanatus

<400> SEQUENCE: 1

Met Arg Asn His Gly Asn Thr Val Ser Tyr Asp His Glu Glu Glu Asn
1               5                   10                  15

Glu Asp Glu Val Ser Met Lys Lys Arg Lys Asn Asp Glu Glu Glu Glu
            20                  25                  30

Glu Asp Asp Gly Lys Lys Lys Lys Lys Lys Lys Glu Gln Gln Asn
        35                  40                  45

Lys Val Ala Phe Tyr Lys Leu Phe Ala Phe Ala Asp Phe Tyr Asp Tyr
    50                  55                  60

Phe Leu Met Ser Phe Gly Ser Ile Gly Ala Cys Ile His Gly Ala Ser
```

-continued

```
                65                  70                  75                  80
Val Pro Val Phe Phe Ile Phe Phe Gly Lys Leu Ile Asn Ile Ile Gly
                    85                  90                  95
Met Ala Tyr Leu Phe Pro Glu Asp Ala Ala Pro Lys Val Ala Lys Tyr
                    100                 105                 110
Ser Leu Asp Phe Leu Tyr Leu Ser Val Val Ile Leu Phe Ser Ser Trp
                    115                 120                 125
Ala Glu Val Ala Cys Trp Met His Ser Gly Glu Arg Gln Ala Ala Lys
                    130                 135                 140
Met Arg Met Ala Tyr Leu Lys Ser Met Leu Asn Gln Asp Ile Ser Leu
145                 150                 155                 160
Phe Asp Thr Glu Ala Ser Thr Gly Glu Val Ile Ala Ala Ile Thr Ser
                    165                 170                 175
Asp Ile Val Ile Val Gln Asp Ala Ile Ser Glu Lys Val Gly Asn Phe
                    180                 185                 190
Leu His Tyr Ile Ser Arg Phe Ile Ser Arg Phe Ile Ile Gly Phe Val
                    195                 200                 205
Arg Val Trp Gln Ile Ser Leu Val Thr Leu Ser Ile Val Pro Leu Ile
210                 215                 220
Ala Leu Ala Gly Gly Leu Tyr Ala Phe Val Thr Ile Gly Leu Ile Ala
225                 230                 235                 240
Lys Val Arg Lys Ser Tyr Val Lys Ala Gly Glu Ile Ala Glu Glu Ile
                    245                 250                 255
Leu Gly Asn Val Arg Thr Val Gln Ala Phe Ala Gly Glu Glu Arg Ala
                    260                 265                 270
Val Asn Leu Tyr Lys Gly Ala Leu Lys Asn Thr Tyr Lys Tyr Gly Arg
                    275                 280                 285
Lys Ala Gly Leu Ala Lys Gly Leu Gly Leu Gly Ser Met His Cys Val
                    290                 295                 300
Leu Phe Leu Ser Trp Ala Leu Leu Val Trp Phe Thr Ser Ile Val Val
305                 310                 315                 320
His Lys Gly Ile Ala Asn Gly Gly Asp Ser Phe Thr Thr Met Leu Asn
                    325                 330                 335
Val Val Ile Ser Gly Leu Ser Leu Gly Gln Ala Ala Pro Asp Ile Ser
                    340                 345                 350
Ala Phe Val Arg Ala Lys Ala Ala Ala Tyr Pro Ile Phe Gln Met Ile
                    355                 360                 365
Glu Arg Asn Thr Val Ser Lys Ser Ser Ser Lys Thr Gly Arg Lys Leu
                    370                 375                 380
Asn Lys Leu Asp Gly His Ile Gln Phe Lys Asp Val Asn Phe Ser Tyr
385                 390                 395                 400
Pro Ser Arg Leu Asp Val Ile Phe Asn Lys Leu Ser Leu Asp Ile
                    405                 410                 415
Pro Ala Gly Lys Ile Val Ala Leu Val Gly Ser Gly Ser Gly Lys
                    420                 425                 430
Ser Thr Val Ile Ser Leu Ile Glu Arg Phe Tyr Glu Pro Leu Ser Gly
                    435                 440                 445
Glu Ile Leu Leu Asp Gly Asn Asn Ile Lys Glu Leu Asp Leu Lys Trp
                    450                 455                 460
Leu Arg Gln Gln Ile Gly Leu Val Asn Gln Glu Pro Ala Leu Phe Ala
465                 470                 475                 480
Thr Ser Ile Arg Glu Asn Ile Leu Tyr Gly Lys Asp Asp Ala Thr Leu
                    485                 490                 495
```

```
Glu Asp Ile Thr Arg Ala Ala Lys Leu Ser Glu Ala Leu Ser Phe Ile
            500                 505                 510
Asn Asn Leu Pro Glu Arg Phe Glu Thr Gln Val Gly Glu Arg Gly Val
            515                 520                 525
Gln Leu Ser Gly Gly Gln Lys Gln Arg Ile Ala Ile Ser Arg Ala Ile
            530                 535                 540
Val Lys Asn Pro Ser Ile Leu Leu Leu Asp Glu Ala Thr Ser Ala Leu
545                 550                 555                 560
Asp Ala Glu Ser Glu Lys Ser Val Gln Glu Ala Leu Asp Arg Val Met
                565                 570                 575
Val Gly Arg Thr Thr Val Val Ala His Arg Leu Ser Thr Ile Arg
            580                 585                 590
Asn Ala Asp Val Ile Ala Val Gln Glu Gly Lys Ile Val Glu Thr
            595                 600                 605
Gly Ser His Asp Glu Leu Ile Ser Lys Pro Asp Ser Val Tyr Ala Ser
            610                 615                 620
Leu Val Gln Phe Gln Glu Thr Ser Ser Leu Gln His His Pro Ser Ile
625                 630                 635                 640
Gly Gln Leu Gly Arg Pro Pro Ser Ile Lys Tyr Ser Arg Glu Leu Ser
            645                 650                 655
Arg Thr Thr Thr Ser Phe Gly Ala Ser Phe Arg Ser Glu Lys Glu Ser
            660                 665                 670
Leu Gly Arg Ile Gly Val Asp Gly Met Glu Met Glu Lys Pro Lys His
            675                 680                 685
Val Ser Ala Arg Arg Leu Tyr Ser Met Val Gly Pro Asp Trp Met Tyr
            690                 695                 700
Gly Ile Val Gly Val Ile Gly Ala Phe Val Thr Gly Ser Gln Met Pro
705                 710                 715                 720
Leu Phe Ala Leu Gly Val Ser Gln Ala Leu Val Ala Phe Tyr Met Asp
            725                 730                 735
Trp Asn Thr Thr Gln His Glu Ile Lys Lys Ile Ser Leu Leu Phe Cys
            740                 745                 750
Gly Gly Ala Val Leu Thr Val Ile Phe His Ala Val Glu His Leu Cys
            755                 760                 765
Phe Gly Ile Met Gly Glu Arg Leu Thr Leu Arg Val Arg Glu Lys Met
            770                 775                 780
Phe His Ala Ile Leu Arg Asn Glu Ile Gly Trp Phe Asp Asp Met Asn
785                 790                 795                 800
Asn Thr Ser Ser Met Leu Ser Ser Arg Leu Glu Thr Asp Ala Thr Leu
                805                 810                 815
Leu Arg Thr Ile Val Val Asp Arg Ser Thr Ile Leu Leu Gln Asn Leu
            820                 825                 830
Ala Leu Val Val Ala Ser Phe Ile Ile Ala Phe Ile Leu Asn Trp Arg
            835                 840                 845
Ile Thr Leu Val Val Leu Ala Thr Tyr Pro Leu Ile Ile Ser Gly His
            850                 855                 860
Ile Ser Glu Lys Leu Phe Met Gln Gly Tyr Gly Gly Asn Leu Ser Lys
865                 870                 875                 880
Ala Tyr Leu Lys Ala Asn Thr Leu Ala Gly Glu Ala Val Gly Asn Ile
                885                 890                 895
Arg Thr Val Ala Ala Phe Cys Ser Glu Gln Lys Val Leu Asp Leu Tyr
            900                 905                 910
```

Ala Lys Glu Leu Val Glu Pro Ser Arg Arg Ser Leu Lys Arg Gly Gln
    915                 920                 925

Ile Ala Gly Ile Phe Tyr Gly Val Ser Gln Phe Ile Phe Ser Ser
    930                 935                 940

Tyr Gly Leu Ala Leu Trp Tyr Gly Ser Val Leu Met Gly Gln Gly Leu
945                 950                 955                 960

Ala Ser Phe Lys Ser Val Met Lys Ser Phe Met Val Leu Ile Val Thr
                965                 970                 975

Ala Leu Ala Met Gly Glu Thr Leu Ala Leu Ala Pro Asp Leu Leu Lys
            980                 985                 990

Gly Asn Gln Met Val Ala Ser Val Phe Glu Val Met Asp Arg Gln Thr
        995                 1000                1005

Glu Val Ser Gly Asp Val Gly Glu Glu Leu Asn Val Val Glu Gly
    1010                1015                1020

Thr Ile Glu Leu Arg Ser Val Glu Phe Ser Tyr Pro Ser Arg Pro
    1025                1030                1035

Asp Val Leu Ile Phe Lys Asp Phe Asn Leu Lys Val Arg Ala Gly
    1040                1045                1050

Lys Ser Ile Ala Leu Val Gly Gln Ser Gly Ser Gly Lys Ser Ser
    1055                1060                1065

Val Leu Ala Leu Ile Leu Arg Phe Tyr Asp Pro Ile Ala Gly Lys
    1070                1075                1080

Val Met Ile Asp Gly Lys Asp Ile Lys Lys Leu Lys Leu Lys Ser
    1085                1090                1095

Leu Arg Lys His Ile Gly Leu Val Gln Gln Glu Pro Ala Leu Phe
    1100                1105                1110

Ala Thr Ser Ile Tyr Glu Asn Ile Leu Tyr Gly Lys Glu Gly Ala
    1115                1120                1125

Ser Glu Ala Glu Val Phe Glu Ala Ala Lys Leu Ala Asn Ala His
    1130                1135                1140

Asn Phe Ile Ser Ala Leu Pro Glu Gly Tyr Ser Thr Lys Val Gly
    1145                1150                1155

Glu Arg Gly Ile Gln Leu Ser Gly Gly Gln Arg Gln Arg Ile Ala
    1160                1165                1170

Ile Ala Arg Ala Val Leu Lys Asn Pro Glu Ile Leu Leu Leu Asp
    1175                1180                1185

Glu Ala Thr Ser Ala Leu Asp Val Glu Ser Glu Arg Val Val Gln
    1190                1195                1200

Gln Ala Leu Asp Arg Leu Met Met Asn Arg Thr Thr Val Val Val
    1205                1210                1215

Ala His Arg Leu Ser Thr Ile Lys Asn Cys Asp Gln Ile Ser Val
    1220                1225                1230

Ile Gln Asp Gly Lys Ile Val Glu Gln Gly Thr His Ser Ser Leu
    1235                1240                1245

Ser Asp Asn Lys Asn Gly Ala Tyr Tyr Lys Leu Ile Asn Ile Gln
    1250                1255                1260

Gln Gln Gln Gln Arg Gln
    1265

<210> SEQ ID NO 2
<211> LENGTH: 3810
<212> TYPE: DNA
<213> ORGANISM: Citrullus lanatus

<400> SEQUENCE: 2

```
atgagaaacc atgggaatac agtttcatat gatcatgaag aagaaaatga agatgaagtt      60
agtatgaaga agaggaagaa tgatgaagaa gaagaagaag atgatgggaa gaagaagaag     120
aagaagaaga aagagcagca aaataaagtt gcttttata aactctttgc ttttgctgat      180
ttttatgatt attttctcat gagttttggt tctattggaa cttgtatcca tggtgcttct     240
gttcctgtct tcttcatttt ctttggaaaa ctcattaata tcattggcat ggcttatctt     300
ttccctgaag atgctgctcc caaagttgct aagtactctt tggattttct atatctcagt     360
gtggttatac tattttcatc atgggcagag gtggcttgtt ggatgcatag tggagagagg     420
caagcagcaa agatgagaat ggcttattta aaatcaatgt taaatcaaga cattagcctt     480
tttgacactg aagcttcaac tggtgaagtc attgctgcta ttactagtga cattgttatt     540
gttcaagatg ccatttctga aaagtaggg aactttttgc attatataag ccggtttata     600
tcaaggttta ttatcggatt tgtgagggta tggcaaatca gtcttgtcac attatctatt     660 gtcccttga ttgcccttgc tggtggtctc tatgcatttg tcaccattgg tcttattgcc     720
aaagtaagaa aatcttatgt caaggctggt gagattgctg aagagatttt aggaaatgta     780
agaacagttc aagcctttgc tggggaagaa agagcagtaa atttatacaa aggagctctc     840
aagaatacct acaagtatgg tagaaaagca gggctggcta agggactggg cctgggatca     900
atgcattgtg tcctttctt gtcatgggct ctgctagttt ggtttaccag cattgttgtc     960
cacaagggca ttgccaatgg tggagactcc ttcaccacaa tgcttaatgt tgtcatttct    1020
ggcttgtcac ttgggcaggc cgcaccagac atttctgcct tgttcgagc aaaggcagcg    1080 gcatatccta tttttcagat gatagagagg aacacagtta gcaaaagcag ctccaaaact    1140
ggccggaaac tgaataagct tgatggtcat attcaattca aggatgttaa tttcagctac    1200
ccatctcgtt tggatgtaat tatattaat aagttatctc ttgatattcc tgcgggcaag    1260
attgtagctc ttgtgggagg aagtggatca ggaaagagca cagtgatatc tttgattgaa    1320
cgattctatg aaccccttc tggagagatt ctattggatg gtaataacat caaggagctg    1380
gatctcaagt ggctaaggca gcaaattggt ttggtcaatc aagagcctgc cctctttgct    1440
acaagcatta gggagaacat tctatatgga aaagatgatg ctaccttga ggacataacg    1500 cgtgcagcca aactttctga ggctttatca tttataaaca atctccctga aagatttgaa    1560
actcaggttg gtgagagagg ggtccaatta tcagggggac aaaaacaag gattgcaata    1620 tctcgtgcaa tcgttaaaaa tccatcaatc ttgttgctgg atgaggcaac aagtgcacta    1680
gatgcagaat ctgaaaagag tgtacaagag gcactcgatc gcgtcatggt tggtcgaacg    1740
actgtagtgg tggctcatcg tttatctacc atacggaatg cagatgtgat tgctgtcgtt    1800
caagaaggaa agatagttga accggaagc catgatgagc tcatttcaaa gccgacagt     1860 gtctatgcat cacttgtcca gttccaagaa acatcatctc tgcaacacca tccctcgatt    1920
gggcagttgg gtcgaccacc tagtataaag tactctcgag aattatctcg cactacaacg    1980
agctttggtg caagttttcg ctccgagaaa gaatctcttg acggattgg agttgatgga    2040 atggaaatgg agaaaccaaa gcatgtttca gcaagaagac tttactccat ggttggaccg    2100
gattggatgt atggcattgt cggcgtcatt ggagcattcg ttacaggatc ccagatgccc    2160
ctttttgctc ttgggtgtc tcaggctctt gttgcatttt acatggactg gaatacaact    2220
caacatgaga tcaagaaaat tcattgcttt tctgtggcg gtgcggtttt aactgtcatt    2280
tttcatgcag ttgagcatct ttgttttgga attatgggag agcgacttac tcttcgagtt    2340
```

-continued

```
cgagaaaaga tgttccatgc tattctgaga aacgagatag gatggttcga tgatatgaac    2400
aacacaagtt ctatgctttc atcacgtcta gaaactgatg caactttatt acgaactatt    2460
gttgtcgacc gctctacaat tcttctgcag aatctagctt tggtcgttgc atcgttcatc    2520
attgctttca ttttgaattg gagaatcact ctagttgtcc tggccactta tccattgatc    2580
attagcggtc acattagcga gaaacttttt atgcaaggct acggtggaaa tttgagcaaa    2640
gcatacctga aagccaatac actggccggt gaggcagttg caacattag gactgttgct     2700 gcattttgtt ctgagcagaa ggttcttgat ctatatgcta aggagctcgt tgagccctcg    2760
agacgttcgc ttaaacgtgg acagattgct ggaatatttt atggtgtctc ccagttcttc    2820 atctttttcat cttacggtct ggccttgtgg tacggttcgg tcttgatggg acaggggctt   2880
gctagcttca aatctgttat gaaatcattc atggttttga tagtaactgc cttagcaatg    2940
ggtgaaactt tggcattggc ccctgatctt ttaaagggaa accagatggt ggcatccgtg    3000
tttgaggtga tggatcgaca gacagaggtg tcgggtgatg ttggtgaaga gctaaatgtg    3060
gtggagggta ccattgagct gaggagtgtt gagttcagct atccatcaag accagatgtt    3120
ttgatcttca aagatttcaa tcttaaagtg agagcaggca gagtatagc cttagttggg     3180 caaagcggtt cggggaaaag ctcggttcta gctcttattc tgcgatttta cgatccaatt    3240
gctgggaagg tgatgattga tggaaaagat attaaaaaac tgaagctcaa atctctcaga    3300
aagcacatcg gcctcgtcca acaggaaccg gctcttttg ccacgtcaat ttacgagaac      3360
attctttatg ggaaagaagg agcttcagaa gccgaagtat cgaagcagc gaaactcgcc      3420 aatgctcata acttcatcag tgctcttcct gaaggctact caacaaaagt tggggaaaga    3480
gggatccaac tttcgggtgg ccaacgacag aggatcgcca ttgcaagagc agtcctgaag    3540
aacccggaaa tactactact agacgaagct acgagtgctc tcgatgtcga atcggaacgt    3600
gtggttcagc aagccttaga cagattgatg atgaacagaa caactgtggt ggttgcacat    3660
aggctttcta ccattaaaaa ctgtgaccaa atctcagtga ttcaagatgg gaagattgta    3720
gaacaaggaa ctcattcaag cctttccgac aacaaaaatg gagcttatta caagttaatc    3780
aacatccaac aacagcaaca aagacagtga                                      3810
```

<210> SEQ ID NO 3
<211> LENGTH: 8691
<212> TYPE: DNA
<213> ORGANISM: Citrullus lanatus

<400> SEQUENCE: 3

```
atgagaaacc atgggaatac agtttcatat gatcatgaag aagaaaatga agatgaagtt      60
agtatgaaga gaggaagaa tgatgaagaa gaagaagaag atgatgggaa gaagaagaag     120
aagaagaaga aagagcagca aaataaagtt gctttttata aactctttgc ttttgctgat    180
ttttatgatt attttctcat gagttttggt tctattggag cttgtatcca tggtgcttct    240
gttcctgtct tcttcatttt ctttggaaaa ctcattaata tcattggcat ggcttatctt    300
ttccctgaag atgctgctcc caaagttgct aaggttcctt cttttaaatt ctctttattt    360
tctcctcatt tctatatttt aaccaaatta ttttttttct ttaaaactac gtctcgtttc    420
gtataaccat ttcattttg ctttttggta tttcaaaagt aagctacttc tatctataag      480
tttttttttg ttttgttttc cacttttcac taatattttg aaaaatcatg ccgaattccg    540
aaaacgaaaa gaaaaatagt ttccgaaaat ttgattccgt tagaatttaa ctaagagttc    600
aagtgttttt tcaaatcata taagaagtta ctttgaagtt tatataaaat taaaaaacaa    660
```

```
aaaattaaat cgttaccgaa cttatagatg aaagtaacta gacattactt caatctataa    720
gtttctttgt tttattttcc acttttcact gttattttga aaaaccatgc cgaattctaa    780
aaactaaaaa aaaaaaaaag tagtttccaa aaaaaacttg ttttgttag aatttgacta     840 aaaattcaag tgttcctatg aaattatat aaaacaaaaa atgaaaaact aaggtctagt     900
ctggtaacca tttcgttttt tgttttgtt tttgaaaatt aagcatattt tctcctcatt     960
tcttacattg ttttgcatct ctcttaagta gaatagttga attctttgcc aaattctaaa   1020
aacaagagca agttttaaa aacaatcttt tttagtttt caaattttgg ctttggtttt     1080
ttaaacattg gtaaaagta aataacaaat gaataaattt gaaggtggaa ctagggtata   1140
taggcttact tttaaaaaac aaaaacaaaa tgattacaaa accgggccta aattagtact   1200
aaatagagcc tattattttt agtttagtct acaaaacttg gatggaattg taaaaccatt   1260
ttgaaaatta aataacaaaa taaagaaact aattataggt tggtttccaa acttaaattt   1320
caaaaattaa aaaaacacc cttaattaac tttgggagat aattgaagat ctatcaatat   1380 tttttttta aaaaattgat tttatttaa ttttttttg gcagtactct ttggattttc     1440
tatatctcag tgtggttata ctatttcat catgggcagg tatgttaatt attattatta   1500
ttatttttaa aaatttagt tatacttgat attattgttt aaaattttgg aattaattaa   1560
ttaaatgtag aggtggcttg ttggatgcat agtggagaga ggcaagcagc aaagatgaga   1620
atggcttatt taaatcaat gttaaatcaa gacattagcc tttttgacac tgaagcttca    1680
actggtgaag tcattgctgc tattactagt gacattgtta ttgttcaaga tgccatttct   1740
gagaaagtat gattctcttt ctttctccca aaaccctaat tttcatatcc atcgtctaac   1800
tattttcctt ttgaatctat cgacttcata tcattcttaa atgaagttac ttttcaaaac   1860
tactcctaaa gtagaaatct aattaggact tcaaacagtg tggcgataat cctagaatgg   1920
tgtgtcaatt gaaattttg gtttaggtta tcatcatacc gttttcata tcctagtatc     1980 catatgacat tccaaagaat ttattctccc ttgtaatttg gaattgttta gcaacttta    2040 aaagaataaa aatgttttg aaataaatga caaaattgaa tgaaatattt attaattaat    2100
ttataaaaat ttaatgcaat tgcagatgga agggagagtg tatttatatt tgacataaaa   2160
aagaaagtaa agttatgaat gaacctgaca tttccttttc attatgcttt gacaaaagac   2220 tatgagtaa atgcaatggt tgagaacatt aaataagtca ccgctgagtt tggtaaggtt    2280
gctttattac ccctttccca tctcggtttt atcttattct tttttttta atacaacaat    2340 tacaactcca agaagaaaa ttactaaacc aaacttactt ttagagaatt tttatctcct    2400
tctcaattga tagaaattta gtttttcatt attttacttt ggctaaatgt tcccatttgt   2460
ttaagaaata ttatattctt cgagcgttaa acgtaagtct tttaaaattt cggataaaac   2520
tttagattga aatgttgtgg cagtgaccta aaatgtcgtg gcaattgtaa tctttatttt   2580
aaatactacc acatcattga tttgcaactt tgaaaaaaa tagggagtgt ttttgaaata    2640
aagtaaaagg tccaaatatt gttttcaaat tgctctaaag ccttttgaaa aggagtgttt   2700
ttttcttttt tttcctatt tgaccagaaa atttcaattt tgttttacc caattgcaaa    2760 tttaactttg attaatcagt taaaatgata aaattgttga aaatatttt aattataaca    2820 aaatgtcact aattatctat gatagatatt gtctatcatt ttctatcccc gtctattagt   2880
acattttgct atttagaaac aacccttta actttctcat ataaatagat ggtgaggttt    2940
tgccccaatt ttagttgtcg atgcattcaa ttttctacaa ttattgctat aactcaccta   3000
```

```
ttaataatgg gccttcagta tttattatgt gcttcgtccc caacccaaca gtctattcct    3060
cacaaagcta acttaacttt tgagatgcaa agtaataaaa ctgctgattc ttgaacttgc    3120
aaaatttaca agaccaaaac ttatgtataa tgtgttatta gaagcattat tcttatatct    3180
ttagaattgt aaggtttggt tttaattcct ctactttgtt ctatcttgaa ttaatgagtt    3240
gcggttaagg tgtttgatga aatgcctgag aagttttgt gggttctgca ggtagggaac     3300
tttttgcatt atataagccg gtttatatca aggtttatta tcggatttgt gagggtatgg    3360
caaatcagtc ttgtcacatt atctattgtc cctttgattg cccttgctgg tggtctctat    3420
gcatttgtca ccattggtct tattgccaaa gtaagaaaat cttatgtcaa ggctggtgag    3480
attgctgaag aggttagcac tttctctgat ttactcatgt agacattgtt ttggttaaat    3540
ataccttaac tcgttatctt actcatgtag acattgtttc ggttaaatag tctaggtctg    3600
gatcttggat tttcttgtgt taatatttgt cgatatgtga cgagagtatt tagagatgtt    3660
taataacatt atggaaatgt ttatatctta tttttgatgt caactaggaa agtagataca    3720
ttatagttgt gttcaataaa ataaagggaa aattaaataa caatttatat ccttaaaact    3780
ttcgattacc tttgaaaatc ctctatgcat tattttctcaa acatgtgtag acttttccaa    3840
atgtcggttt tacaaaatag acgtgtatgg acaattctca aaggaaatta tgtataagag    3900
tctaaattga ttcatttaaa agtttggggg taattgatac aattataagt tttactcaag    3960
gttttcccaa atagaatgta atggaggtgt cgtatattga tatacttaca aaagttaaag    4020
gttcaaattg atacaatgat tagtttaagg tttaaattga tacaacgcct aaagtttaag    4080
ggtataaatt gatgctttcc ctgaaataag taaatgaaac ttagtggat aaatggtaac     4140 caacttcttt ctttgcttaa gagctctata ttggttttaa ctatcttttc atcaccccctt   4200 accctttctgt ttttgtccctt taagatttta ggaaatgtaa aacagttca agcctttgct    4260 ggggaagaaa gagcagtaaa tttatacaaa ggagctctca agaatacccta caagtatggt   4320 agaaaagcag ggctggctaa gggactgggc ctgggatcaa tgcattgtgt ccttttcttg    4380
tcatgggctc tgctagtttg gtttaccagc attgttgtcc acaagggcat tgccaatggt    4440
ggagactcct tcaccacaat gcttaatgtt gtcatttctg gcttgtaagt cttttcagctt   4500 atcttaatat cgaatcgtct gttaattaca ttccatttcc aattctgtgc tacacattgt    4560
agaaatagaa catccccaca cttacataaa atgggttgct tactttagct tgaacattga    4620
aaaccagtat tcaaagtatc caaggtcttt atttcctttg tgcaaagtat agaactatcc    4680
attttggatt tgtaaatgtg atggaattag gcaaatatgt ataagataaa gtaatatata    4740
tcaagctttt ccacagtatg atcttcatttt agccgatggt gttcatcaag ctactaaata    4800
aggattgata gatggtatgg atttgaagac tttcaaactt caaaacactt tctagtaaaa    4860
aattctctgt ttacccagaa tttaagtgtg ttaaaaagtc cactagctac cccaactttc    4920
gaaatgagtg ctatcttaat tctaatgttc tggtaatcca agcttcttgt taatggttcc    4980
acttgtttca ggtcatttca ttttaatgcc tttgtaattc aaaggtaggt tattaatggt    5040
tacattgcct caggtcactt gggcaggccg caccagacat ttctgccttt gttcgagcaa    5100
aggcagcggc atatcctatt tttcagatga tagagaggaa cacagttagc aaaagcagct    5160
ccaaaactgg ccggaaactg aataagcttg atggtcatat tcaattcaag gatgttaatt    5220
tcagctaccc atctcgtttg gatgtaatta tatttaataa gttatctctt gatattcctg    5280
cgggcaagat tgtagctctt gtgggaggaa gtggatcagg aaagagcaca gtgatatctt    5340
tgattgaacg attctatgaa ccccctttctg gagagattct attggatggt aataacatca    5400
```

```
aggagctgga tctcaagtgg ctaaggcagc aaattggttt ggtcaatcaa gagcctgccc    5460
tctttgctac aagcattagg gagaacattc tatatgaaaa agatgatgct acccttgagg    5520
acataacgcg tgcagccaaa ctttctgagg ctttatcatt tataaacaat ctccctgaaa    5580
gatttgaaac tcaggtatta ttatctatct ctgagaacta accatgagaa tttgtgttgg    5640
taaaggttca aagctttaaa aagagacatt gattccaaaa aaataacttg gcaagtttta    5700
aacttaaaaa aaactgtctt ctaataatta attaaatagt tgctattagt tcatctaatg    5760
ttttgttcat tagagtggaa atcgcagtc  ggattataag catagtagaa aataataact    5820
ctagattaaa tgttttgttc taggttggtg agagaggggt ccaattatca gggggacaaa    5880
aacaaaggat tgcaatatct cgtgcaatcg ttaaaaatcc atcaatcttg ttgctggatg    5940
aggcaacaag tgcactagat gcagaatctg aaaagagtgt acaagaggca ctcgatcgcg    6000
tcatggttgg tcgaacgact gtagtggtgg ctcatcgttt atctaccata cggaatgcag    6060
atgtgattgc tgtcgttcaa gaaggaaaga tagttgaaac cggaagccat gatgagctca    6120
tttcaaagcc ggacagtgtc tatgcatcac ttgtccagtt ccaagaaaca tcatctctgc    6180
aacaccatcc ctcgattggg cagttgggtc gaccacctag gtattccatt ctcactttag    6240
cttacaatac gatgattttt tctatgaaac acacatttta tagtttcatt ttttatgata    6300
ggattagcca ataataataa tatgcatcaa acacccttag atgctacatt ttgattaaaa    6360
aatcaagtta cttattgcta aactgttttt aaattcatcc aacttgtagt ataaagtact    6420
ctcgagaatt atctcgcact acaacgagct ttggtgcaag ttttcgctcc gagaaagaat    6480
ctcttggacg gattggagtt gatggaatgg aaatggagaa accaaagcat gtttcagcaa    6540
gaagacttta ctccatggtt ggaccggatt ggatgtatgg cattgtcggc gtcattggag    6600
cattcgttac aggatcccag atgccccttt ttgctcttgg ggtctctcag gctcttgttg    6660
cattttacat ggactggaat acaactcaac atgagatcaa gaaaatttca ttgcttttct    6720
gtggcggtgc ggttttaact gtcattttc  atgcagttga gcatctttgt tttggaatta    6780
tgggagagcg acttactctt cgagttcgag aaaagatgtt ccatggtatc ctgcaatctt    6840
tacacctaag tgccttttat tttcaagtca ttcaattttc tctaagcaat ttttgtttgg    6900
ttgcagctat tctgagaaac gagataggat ggttcgatga tatgaacaac acaagttcta    6960
tgctttcatc acgtctagaa actgatgcaa ctttattacg aactattgtt gtcgaccgct    7020
ctacaattct tctgcagaat ctagctttgg tcgttgcatc gttcatcatt gctttcattt    7080
tgaattggag aatcactcta gttgtcctgg ccacttatcc attgatcatt agcggtcaca    7140
ttagcgaggt tttctatcat aacttctcta aattacttat ttctttccct gaatttcaaa    7200
tatttcctca tgaaactgct cttttccatt gtgttttaga aacttttttat gcaaggctac    7260 ggtggaaatt tgagcaaagc atacctgaaa gccaatacac tggccggtga ggcagttggc    7320
aacattagga ctgttgctgc attttgttct gagcagaagg ttcttgatct atatgctaag    7380
gagctcgttg agccctcgag acgttcgctt aaacgtggac agattgctgg aatattttat    7440
ggtgtctccc agttcttcat cttttcatct tacggtctgg ccttgtggta tgtgatttaa    7500
gaaactattt tagactactt gtcataaata tttgaataga aattagaatc aatccgaatt    7560
aattttatga atgattcaac tatcttaagc atgtgctatt atgcaggtac ggttcggtct    7620
tgatgggaca ggggcttgct agcttcaaat ctgttatgaa atcattcatg gttttgatag    7680
taactgcctt agcaatgggt gaaactttgg cattggcccc tgatctttta aagggaaacc    7740
```

```
agatggtggc atccgtgttt gaggtgatgg atcgacagac agaggtgtcg ggtgatgttg    7800
gtgaagagct aaatgtggtg gagggtacca ttgagctgag gagtgttgag ttcagctatc    7860
catcaagacc agatgttttg atcttcaaag atttcaatct taaagtgaga gcaggcaaga    7920
gtatagcctt agttgggcaa agcggttcgg ggaaaagctc ggttctagct cttattctgc    7980
gattttacga tccaattgct gggaaggtga tgattgatgg taagttttct caacaatctg    8040
ctcacttttg atagtaactg cactaccata ttctacattt ttacaagtaa aattctagat    8100
catcttttca gttttgatt aacagagctt ttatatcttg caggaaaaga tattaaaaaa    8160
ctgaagctca aatctctcag aaagcacatc ggcctcgtcc aacaggaacc ggctcttttt    8220
gccacgtcaa tttacgagaa cattctttat gggaagaag gagcttcaga agccgaagta    8280
ttcgaagcag cgaaactcgc caatgctcat aacttcatca gtgctcttcc tgaaggctac    8340
tcaacaaaag ttggggaaag agggatccaa ctttcgggtg ccaacgaca gaggatcgcc    8400 attgcaagag cagtcctgaa gaacccggaa atactactac tagacgaagc tacgagtgct    8460
ctcgatgtcg aatcggaacg tgtggttcag caagccttag acagattgat gatgaacaga    8520
acaactgtgg tggttgcaca taggctttct accattaaaa actgtgacca aatctcagtg    8580
attcaagatg ggaagattgt agaacaagga actcattcaa gcctttccga caacaaaat    8640 ggagcttatt acaagttaat caacatccaa caacagcaac aaagacagtg a             8691
```

<210> SEQ ID NO 4  
<211> LENGTH: 1272  
<212> TYPE: PRT  
<213> ORGANISM: Cucumis sativus

<400> SEQUENCE: 4

```
Met Arg Asn His Gly Ser Ser Ile Ser Tyr His Glu His Arg Glu Glu
1               5                   10                  15

Glu Asn Glu Glu His Asp Lys Lys Arg Lys Asn Asp Glu Glu Glu
            20                  25                  30

Glu Glu Glu Asp Gly Lys Glu Met Lys Lys Lys Lys Lys Glu Glu
        35                  40                  45

Lys Asn Asn Lys Val Ala Phe Tyr Lys Leu Phe Ala Phe Ala Asp Phe
50                  55                  60

Tyr Asp Tyr Val Leu Met Ser Ile Gly Ser Ile Gly Ala Cys Ile His
65                  70                  75                  80

Gly Ala Ser Val Pro Val Phe Phe Ile Phe Phe Gly Lys Leu Ile Asn
                85                  90                  95

Ile Ile Gly Met Ala Tyr Leu Phe Pro Glu Ala Ala Ala Pro Lys Val
            100                 105                 110

Ala Lys Tyr Ser Leu Asp Phe Leu Tyr Leu Ser Val Ala Ile Leu Phe
        115                 120                 125

Ser Ser Trp Ala Glu Val Ala Cys Trp Met His Ser Gly Glu Arg Gln
130                 135                 140

Ala Ala Lys Met Arg Met Ala Tyr Leu Arg Ser Met Leu Asn Gln Asp
145                 150                 155                 160

Ile Ser Leu Phe Asp Thr Glu Ala Ser Thr Gly Glu Val Ile Ala Ala
                165                 170                 175

Ile Thr Ser Asp Ile Val Val Gln Asp Ala Ile Ser Glu Lys Val
            180                 185                 190

Gly Asn Phe Leu His Tyr Ile Ser Arg Phe Ile Ser Gly Phe Ile Ile
        195                 200                 205
```

```
Gly Phe Val Arg Val Trp Gln Ile Ser Leu Val Thr Leu Ser Ile Val
        210                 215                 220
Pro Leu Ile Ala Leu Ala Gly Gly Leu Tyr Ala Phe Val Thr Ile Gly
225                 230                 235                 240
Leu Ile Ala Lys Val Arg Lys Ser Tyr Val Lys Ala Gly Glu Ile Ala
                245                 250                 255
Glu Glu Ile Leu Gly Asn Val Arg Thr Val Gln Ala Phe Ala Gly Glu
                260                 265                 270
Glu Arg Ala Val Asn Leu Tyr Lys Gly Ala Leu Lys Asn Thr Tyr Lys
                275                 280                 285
Tyr Gly Arg Lys Ala Gly Leu Ala Lys Gly Leu Gly Leu Gly Ser Met
        290                 295                 300
His Cys Val Leu Phe Leu Ser Trp Ala Leu Leu Val Trp Phe Thr Ser
305                 310                 315                 320
Ile Val Val His Lys Gly Ile Ala Asn Gly Gly Asp Ser Phe Thr Thr
                325                 330                 335
Met Leu Asn Val Val Ile Ser Gly Leu Ser Leu Gly Gln Ala Ala Pro
                340                 345                 350
Asp Ile Ser Ala Phe Val Arg Ala Lys Ala Ala Ala Tyr Pro Ile Phe
                355                 360                 365
Gln Met Ile Glu Arg Asn Thr Val Ser Lys Ser Ser Ser Lys Thr Gly
        370                 375                 380
Trp Lys Leu Asn Lys Leu Asp Gly Phe Ile Gln Phe Lys Asp Val Asn
385                 390                 395                 400
Phe Ser Tyr Pro Ser Arg Gln Asp Val Ile Ile Phe Asn Lys Leu Ser
                405                 410                 415
Leu Asp Ile Pro Ala Gly Lys Ile Val Ala Leu Val Gly Gly Ser Gly
                420                 425                 430
Ser Gly Lys Ser Thr Val Ile Ser Leu Ile Glu Arg Phe Tyr Glu Pro
        435                 440                 445
Leu Ser Gly Glu Ile Leu Leu Asp Gly His Asn Ile Lys Asp Leu Asp
450                 455                 460
Leu Lys Trp Phe Arg Gln Gln Ile Gly Leu Val Asn Gln Glu Pro Ala
465                 470                 475                 480
Leu Phe Ala Thr Ser Ile Arg Glu Asn Ile Leu Tyr Gly Lys Asp Asp
                485                 490                 495
Ala Thr Leu Glu Asp Ile Thr Arg Ala Ala Lys Leu Ser Glu Ala Leu
                500                 505                 510
Ser Phe Ile Asn Asn Leu Pro Glu Arg Phe Glu Thr Gln Val Gly Glu
                515                 520                 525
Arg Gly Val Gln Leu Ser Gly Gly Gln Lys Gln Arg Ile Ala Ile Ser
        530                 535                 540
Arg Ala Ile Val Lys Asn Pro Ser Ile Leu Leu Leu Asp Glu Ala Thr
545                 550                 555                 560
Ser Ala Leu Asp Ala Glu Ser Glu Lys Ser Val Gln Glu Ala Leu Asp
                565                 570                 575
Arg Val Met Val Gly Arg Thr Thr Val Val Ala His Arg Leu Ser
                580                 585                 590
Thr Ile Arg Asn Ala Asp Val Ile Ala Val Val Gln Glu Gly Lys Ile
                595                 600                 605
Val Glu Thr Gly Ser His Asp Glu Leu Ile Ser Arg Pro Asp Ser Val
        610                 615                 620
Tyr Ala Ser Leu Val Gln Phe Gln Glu Thr Ala Ser Leu Gln Arg His
```

```
            625                 630                 635                 640
        Pro Ser Ile Gly Gln Leu Gly Arg Pro Pro Ser Ile Lys Tyr Ser Arg
                        645                 650                 655

Glu Leu Ser Arg Thr Thr Thr Ser Phe Gly Ala Ser Phe Arg Ser Glu
                        660                 665                 670

Lys Glu Ser Leu Gly Arg Ile Gly Val Asp Gly Met Glu Met Glu Lys
                        675                 680                 685

Pro Arg His Val Ser Ala Lys Arg Leu Tyr Ser Met Val Gly Pro Asp
                        690                 695                 700

Trp Met Tyr Gly Ile Val Gly Val Ile Gly Ala Phe Val Thr Gly Ser
        705                 710                 715                 720

Gln Met Pro Leu Phe Ala Leu Gly Val Ser Gln Ala Leu Val Ala Phe
                        725                 730                 735

Tyr Met Asp Trp Asp Thr Thr Gln His Glu Ile Lys Lys Ile Ser Leu
                        740                 745                 750

Leu Phe Cys Gly Gly Ala Val Leu Thr Val Ile Phe His Ala Val Glu
                        755                 760                 765

His Leu Cys Phe Gly Ile Met Gly Glu Arg Leu Thr Leu Arg Val Arg
                        770                 775                 780

Glu Met Met Phe His Ala Ile Leu Arg Asn Glu Ile Gly Trp Phe Asp
        785                 790                 795                 800

Asp Met Asn Asn Thr Ser Ala Met Leu Ser Ser Arg Leu Glu Thr Asp
                        805                 810                 815

Ala Thr Leu Leu Arg Thr Ile Val Val Asp Arg Ser Thr Ile Leu Leu
                        820                 825                 830

Gln Asn Leu Ala Leu Val Val Ala Ser Phe Ile Ile Ala Phe Ile Leu
                        835                 840                 845

Asn Trp Arg Ile Thr Leu Val Val Leu Ala Thr Tyr Pro Leu Ile Ile
                        850                 855                 860

Ser Gly His Ile Ser Glu Lys Leu Phe Met Gln Gly Tyr Gly Gly Asn
        865                 870                 875                 880

Leu Ser Lys Ala Tyr Leu Lys Ala Asn Thr Leu Ala Gly Glu Ala Val
                        885                 890                 895

Gly Asn Ile Arg Thr Val Ala Ala Phe Cys Ser Glu Glu Lys Val Leu
                        900                 905                 910

Asp Leu Tyr Ala Lys Glu Leu Val Glu Pro Ser Arg Arg Ser Leu Lys
                        915                 920                 925

Arg Gly Gln Ile Ala Gly Ile Phe Tyr Gly Val Ser Gln Phe Phe Ile
                        930                 935                 940

Phe Ser Ser Tyr Gly Leu Ala Leu Trp Tyr Gly Ser Val Leu Met Gly
        945                 950                 955                 960

His Gly Leu Ala Ser Phe Lys Ser Val Met Lys Ser Phe Met Val Leu
                        965                 970                 975

Ile Val Thr Ala Leu Ala Met Gly Glu Thr Leu Ala Leu Ala Pro Asp
                        980                 985                 990

Leu Leu Lys Gly Asn Gln Met Val  Ala Ser Val Phe Glu  Val Met Asp
                        995                 1000                1005

Arg Gln  Thr Glu Val Ser Gly  Asp Val Gly Glu Glu  Leu Asn Val
                1010                1015                1020

Val Glu  Gly Thr Ile Glu Leu  Arg Asn Val Glu Phe  Val Tyr Pro
                1025                1030                1035

Ser Arg  Pro Asp Val Met Ile  Phe Lys Asp Phe Asn  Leu Lys Val
                1040                1045                1050
```

Arg Ala Gly Lys Ser Ile Ala Leu Val Gly Gln Ser Gly Ser Gly
1055            1060                1065

Lys Ser Ser Val Leu Ala Leu Ile Leu Arg Phe Tyr Asp Pro Ile
1070            1075                1080

Ala Gly Lys Val Met Ile Asp Gly Lys Asp Ile Lys Lys Leu Lys
1085            1090                1095

Leu Lys Ser Leu Arg Lys His Ile Gly Leu Val Gln Gln Glu Pro
1100            1105                1110

Ala Leu Phe Ala Thr Ser Ile Tyr Glu Asn Ile Leu Tyr Gly Lys
1115            1120                1125

Glu Gly Ala Ser Glu Ala Glu Val Phe Glu Ala Ala Lys Leu Ala
1130            1135                1140

Asn Ala His Asn Phe Ile Ser Ala Leu Pro Glu Gly Tyr Ser Thr
1145            1150                1155

Lys Val Gly Glu Arg Gly Ile Gln Leu Ser Gly Gly Gln Arg Gln
1160            1165                1170

Arg Ile Ala Ile Ala Arg Ala Val Leu Lys Asn Pro Glu Ile Leu
1175            1180                1185

Leu Leu Asp Glu Ala Thr Ser Ala Leu Asp Val Glu Ser Glu Arg
1190            1195                1200

Val Val Gln Gln Ala Leu Asp Arg Leu Met Met Asn Arg Thr Thr
1205            1210                1215

Val Val Val Ala His Arg Leu Ser Thr Ile Lys Asn Cys Asp Gln
1220            1225                1230

Ile Ser Val Ile Gln Asp Gly Lys Ile Val Glu Gln Gly Thr His
1235            1240                1245

Ser Ser Leu Ser Glu Asn Lys Asn Gly Ala Tyr Tyr Lys Leu Ile
1250            1255                1260

Asn Ile Gln Gln Gln Gln Gln Arg Gln
1265            1270

<210> SEQ ID NO 5
<211> LENGTH: 1237
<212> TYPE: PRT
<213> ORGANISM: Cucumis melo

<400> SEQUENCE: 5

Met Lys Thr Lys Lys Lys Lys Lys Lys Gln Glu Lys Asn Asn Asn
1               5                   10                  15

Lys Val Ala Phe Tyr Lys Leu Phe Ala Phe Ala Asp Phe Tyr Asp Tyr
            20                  25                  30

Ile Leu Met Ser Ile Gly Ser Ile Gly Ala Cys Ile His Gly Ala Ser
                35                  40                  45

Val Pro Val Phe Phe Ile Phe Phe Gly Lys Leu Ile Asn Ile Ile Gly
        50                  55                  60

Met Ala Tyr Leu Phe Pro Glu Ala Ala Pro Lys Val Ala Lys Tyr
65                  70                  75                  80

Ser Leu Asp Phe Leu Tyr Leu Ser Val Ala Ile Leu Phe Ser Ser Trp
                85                  90                  95

Ala Glu Val Ala Cys Trp Met His Ser Gly Glu Arg Gln Ala Ala Lys
                100                 105                 110

Met Arg Met Ala Tyr Leu Lys Ser Met Leu Asn Gln Asp Ile Ser Leu
            115                 120                 125

Phe Asp Thr Glu Ala Ser Thr Gly Glu Val Ile Ala Ala Ile Thr Ser

```
            130                 135                 140
Asp Ile Val Val Gln Asp Ala Ile Ser Glu Lys Val Gly Asn Phe
145                 150                 155                 160

Leu His Tyr Ile Ser Arg Phe Ile Ser Gly Phe Ile Gly Phe Val
                    165                 170                 175

Arg Val Trp Gln Ile Ser Leu Val Thr Leu Ser Ile Val Pro Leu Ile
                180                 185                 190

Ala Leu Ala Gly Gly Leu Tyr Ala Phe Val Thr Ile Gly Leu Ile Ala
                195                 200                 205

Lys Val Arg Lys Ser Tyr Val Lys Ala Gly Glu Ile Ala Glu Ile
                210                 215                 220

Leu Gly Asn Val Arg Thr Val Gln Ala Phe Ala Gly Glu Glu Arg Ala
225                 230                 235                 240

Val Asn Leu Tyr Lys Gly Ala Leu Lys Asn Thr Tyr Lys Tyr Gly Arg
                245                 250                 255

Lys Ala Gly Leu Ala Lys Gly Leu Gly Leu Gly Ser Met His Cys Val
                260                 265                 270

Leu Phe Leu Ser Trp Ala Leu Leu Val Trp Phe Thr Ser Ile Val Val
                275                 280                 285

His Lys Gly Ile Ala Asn Gly Gly Asp Ser Phe Thr Thr Met Leu Asn
                290                 295                 300

Val Val Ile Ser Gly Leu Ser Leu Gly Gln Ala Ala Pro Asp Ile Ser
305                 310                 315                 320

Ala Phe Val Arg Ala Lys Ala Ala Ala Tyr Pro Ile Phe Gln Met Ile
                325                 330                 335

Glu Arg Asn Thr Val Ser Lys Ser Ser Lys Thr Gly Arg Lys Leu
                340                 345                 350

Asn Lys Leu Asp Gly Tyr Ile Gln Phe Lys Asp Val Asn Phe Ser Tyr
                355                 360                 365

Pro Ser Arg Pro Asp Val Ile Ile Phe Asn Lys Leu Ser Leu Asp Ile
                370                 375                 380

Pro Ala Gly Lys Ile Val Ala Leu Val Gly Gly Ser Gly Ser Gly Lys
385                 390                 395                 400

Ser Thr Val Ile Ser Leu Ile Glu Arg Phe Tyr Glu Pro Leu Ser Gly
                405                 410                 415

Glu Ile Leu Leu Asp Gly His Asn Ile Lys Glu Leu Asp Leu Lys Trp
                420                 425                 430

Phe Arg Gln Gln Ile Gly Leu Val Asn Gln Glu Pro Ala Leu Phe Ala
                435                 440                 445

Thr Ser Ile Arg Glu Asn Ile Leu Tyr Gly Lys Asp Asp Ala Thr Leu
                450                 455                 460

Glu Asp Ile Thr Arg Ala Ala Lys Leu Ser Glu Ala Leu Ser Phe Ile
465                 470                 475                 480

Asn Asn Leu Pro Glu Arg Phe Glu Thr Gln Val Gly Glu Arg Gly Val
                485                 490                 495

Gln Leu Ser Gly Gly Gln Lys Gln Arg Ile Ala Ile Ser Arg Ala Ile
                500                 505                 510

Val Lys Asn Pro Ser Val Leu Leu Leu Asp Glu Ala Thr Ser Ala Leu
                515                 520                 525

Asp Ala Glu Ser Glu Lys Ser Val Gln Glu Ala Leu Asp Arg Val Met
530                 535                 540

Val Gly Arg Thr Thr Val Val Val Ala His Arg Leu Ser Thr Ile Arg
545                 550                 555                 560
```

-continued

Asn Ala Asp Val Ile Ala Val Gln Glu Gly Lys Ile Val Glu Thr
                565                 570                 575

Gly Ser His Asp Glu Leu Ile Ser Arg Pro Asp Ser Val Tyr Ala Ser
            580                 585                 590

Leu Val Gln Phe Gln Glu Thr Ala Ser Leu Gln Arg His Pro Ser Phe
        595                 600                 605

Gly Gln Leu Gly Arg Pro Pro Ser Ile Lys Tyr Ser Arg Glu Leu Ser
    610                 615                 620

Arg Thr Thr Thr Ser Phe Gly Ala Ser Phe Arg Ser Glu Lys Glu Ser
625                 630                 635                 640

Leu Gly Arg Ile Gly Val Asp Gly Met Glu Met Glu Lys Pro Arg His
                645                 650                 655

Val Ser Ala Lys Arg Leu Tyr Ser Met Val Gly Pro Asp Trp Met Tyr
            660                 665                 670

Gly Ile Val Gly Val Ile Gly Ala Phe Val Thr Gly Ser Gln Met Pro
        675                 680                 685

Leu Phe Ala Leu Gly Val Ser Gln Ala Leu Val Ala Phe Tyr Met Asp
    690                 695                 700

Trp Asp Thr Thr Gln His Glu Ile Lys Lys Ile Ser Leu Leu Phe Cys
705                 710                 715                 720

Gly Gly Ala Val Leu Thr Val Ile Phe His Ala Val Glu His Leu Cys
                725                 730                 735

Phe Gly Ile Met Gly Glu Arg Leu Thr Leu Arg Val Arg Glu Met Met
            740                 745                 750

Phe His Ala Ile Leu Arg Asn Glu Ile Gly Trp Phe Asp Asp Met Asn
        755                 760                 765

Asn Thr Ser Ala Met Leu Ser Ser Arg Leu Glu Thr Asp Ala Thr Leu
    770                 775                 780

Leu Arg Thr Ile Val Val Asp Arg Ser Thr Ile Leu Leu Gln Asn Leu
785                 790                 795                 800

Ala Leu Val Val Ala Ser Phe Ile Ile Ala Phe Ile Leu Asn Trp Arg
                805                 810                 815

Ile Thr Leu Val Val Leu Ala Thr Tyr Pro Leu Ile Ile Ser Gly His
            820                 825                 830

Ile Ser Glu Lys Leu Phe Met Gln Gly Tyr Gly Gly Asn Leu Ser Lys
        835                 840                 845

Ala Tyr Leu Lys Ala Asn Thr Leu Ala Gly Glu Ala Val Gly Asn Ile
    850                 855                 860

Arg Thr Val Ala Ala Phe Cys Ser Glu Glu Lys Val Leu Asp Leu Tyr
865                 870                 875                 880

Ala Lys Glu Leu Val Glu Pro Ser Arg Arg Ser Leu Lys Arg Gly Gln
                885                 890                 895

Ile Ala Gly Ile Phe Tyr Gly Val Ser Gln Phe Phe Ile Phe Ser Ser
            900                 905                 910

Tyr Gly Leu Ala Leu Trp Tyr Gly Ser Val Leu Met Gly Gln Gly Leu
        915                 920                 925

Ala Ser Phe Lys Ser Val Met Lys Ser Phe Met Val Leu Ile Val Thr
    930                 935                 940

Ala Leu Ala Met Gly Glu Thr Leu Ala Leu Ala Pro Asp Leu Leu Lys
945                 950                 955                 960

Gly Asn Gln Met Val Ala Ser Val Phe Glu Val Met Asp Arg Gln Thr
                965                 970                 975

```
Glu Val Pro Gly Asp Val Gly Glu Leu Asn Val Glu Gly Thr
                980             985                 990

Ile Glu Leu Arg Asn Val Glu Phe Val Tyr Pro Ser Arg Pro Asp Val
        995                 1000                1005

Met Ile Phe Lys Asp Phe Asn Leu Lys Val Arg Ala Gly Lys Ser
    1010            1015                1020

Ile Ala Leu Val Gly Gln Ser Gly Ser Gly Lys Ser Ser Val Leu
    1025            1030                1035

Ala Leu Ile Leu Arg Phe Tyr Asp Pro Ile Ala Gly Lys Val Met
    1040            1045                1050

Ile Asp Gly Lys Asp Ile Lys Lys Leu Lys Leu Lys Ser Leu Arg
    1055            1060                1065

Lys His Ile Gly Leu Val Gln Gln Glu Pro Ala Leu Phe Ala Thr
    1070            1075                1080

Thr Ile Tyr Glu Asn Ile Leu Tyr Gly Lys Glu Gly Ala Ser Glu
    1085            1090                1095

Ala Glu Val Phe Glu Ala Ala Lys Leu Ala Asn Ala His Asn Phe
    1100            1105                1110

Ile Ser Ala Leu Pro Glu Gly Tyr Ser Thr Lys Val Gly Glu Arg
    1115            1120                1125

Gly Ile Gln Leu Ser Gly Gly Gln Arg Gln Arg Ile Ala Ile Ala
    1130            1135                1140

Arg Ala Val Leu Lys Asn Pro Glu Ile Leu Leu Leu Asp Glu Ala
    1145            1150                1155

Thr Ser Ala Leu Asp Val Glu Ser Glu Arg Val Val Gln Gln Ala
    1160            1165                1170

Leu Asp Arg Leu Met Met Asn Arg Thr Thr Val Val Val Ala His
    1175            1180                1185

Arg Leu Ser Thr Ile Lys Asn Cys Asp Gln Ile Ser Val Ile Gln
    1190            1195                1200

Asp Gly Lys Ile Val Glu Gln Gly Thr His Ser Ser Leu Ser Glu
    1205            1210                1215

Asn Lys Asn Gly Ala Tyr Tyr Lys Leu Ile Asn Ile Gln Gln Gln
    1220            1225                1230

Gln Gln Arg Gln
    1235

<210> SEQ ID NO 6
<211> LENGTH: 1269
<212> TYPE: PRT
<213> ORGANISM: Citrullus lanatus

<400> SEQUENCE: 6

Met Arg Asn His Gly Asn Thr Val Ser Tyr Asp His Glu Glu Glu Asn
1               5                   10                  15

Glu Asp Glu Val Ser Met Lys Lys Arg Lys Asn Asp Glu Glu Glu Glu
            20                  25                  30

Glu Asp Asp Gly Lys Lys Lys Lys Lys Lys Glu Gln Gln Asn
        35                  40                  45

Lys Val Ala Phe Tyr Lys Leu Phe Ala Phe Ala Asp Phe Tyr Asp Tyr
    50                  55                  60

Phe Leu Met Ser Phe Gly Ser Ile Gly Ala Cys Ile His Gly Ala Ser
65                  70                  75                  80

Val Pro Val Phe Phe Ile Phe Phe Gly Lys Leu Ile Asn Ile Ile Gly
            85                  90                  95
```

```
Met Ala Tyr Leu Phe Pro Glu Asp Ala Ala Pro Lys Val Ala Lys Tyr
            100                 105                 110

Ser Leu Asp Phe Leu Tyr Leu Ser Val Val Ile Leu Phe Ser Ser Trp
            115                 120                 125

Ala Glu Val Ala Cys Trp Met His Ser Gly Glu Arg Gln Ala Ala Lys
            130                 135                 140

Met Arg Met Ala Tyr Leu Lys Ser Met Leu Asn Gln Asp Ile Ser Leu
145                 150                 155                 160

Phe Asp Thr Glu Ala Ser Thr Gly Glu Val Ile Ala Ala Ile Thr Ser
                165                 170                 175

Asp Ile Val Ile Val Gln Asp Ala Ile Ser Glu Lys Val Gly Asn Phe
            180                 185                 190

Leu His Tyr Ile Ser Arg Phe Ile Ser Gly Phe Ile Ile Gly Phe Val
            195                 200                 205

Arg Val Trp Gln Ile Ser Leu Val Thr Leu Ser Ile Val Pro Leu Ile
            210                 215                 220

Ala Leu Ala Gly Gly Leu Tyr Ala Phe Val Thr Ile Gly Leu Ile Ala
225                 230                 235                 240

Lys Val Arg Lys Ser Tyr Val Lys Ala Gly Glu Ile Ala Glu Glu Ile
                245                 250                 255

Leu Gly Asn Val Arg Thr Val Gln Ala Phe Ala Gly Glu Glu Arg Ala
            260                 265                 270

Val Asn Leu Tyr Lys Gly Ala Leu Lys Asn Thr Tyr Lys Tyr Gly Arg
            275                 280                 285

Lys Ala Gly Leu Ala Lys Gly Leu Gly Leu Gly Ser Met His Cys Val
            290                 295                 300

Leu Phe Leu Ser Trp Ala Leu Leu Val Trp Phe Thr Ser Ile Val Val
305                 310                 315                 320

His Lys Gly Ile Ala Asn Gly Gly Asp Ser Phe Thr Thr Met Leu Asn
                325                 330                 335

Val Val Ile Ser Gly Leu Ser Leu Gly Gln Ala Ala Pro Asp Ile Ser
            340                 345                 350

Ala Phe Val Arg Ala Lys Ala Ala Ala Tyr Pro Ile Phe Gln Met Ile
            355                 360                 365

Glu Arg Asn Thr Val Ser Lys Ser Ser Ser Lys Thr Gly Arg Lys Leu
            370                 375                 380

Asn Lys Leu Asp Gly His Ile Gln Phe Lys Asp Val Asn Phe Ser Tyr
385                 390                 395                 400

Pro Ser Arg Leu Asp Val Ile Ile Phe Asn Lys Leu Ser Leu Asp Ile
                405                 410                 415

Pro Ala Gly Lys Ile Val Ala Leu Val Gly Gly Ser Gly Ser Gly Lys
            420                 425                 430

Ser Thr Val Ile Ser Leu Ile Glu Arg Phe Tyr Glu Pro Leu Ser Gly
            435                 440                 445

Glu Ile Leu Leu Asp Gly Asn Asn Ile Lys Glu Leu Asp Leu Lys Trp
            450                 455                 460

Leu Arg Gln Gln Ile Gly Leu Val Asn Gln Glu Pro Ala Leu Phe Ala
465                 470                 475                 480

Thr Ser Ile Arg Glu Asn Ile Leu Tyr Gly Lys Asp Asp Ala Thr Leu
                485                 490                 495

Glu Asp Ile Thr Arg Ala Ala Lys Leu Ser Glu Ala Leu Ser Phe Ile
            500                 505                 510
```

-continued

```
Asn Asn Leu Pro Glu Arg Phe Glu Thr Gln Val Gly Glu Arg Gly Val
            515                 520                 525
Gln Leu Ser Gly Gly Gln Lys Gln Arg Ile Ala Ile Ser Arg Ala Ile
        530                 535                 540
Val Lys Asn Pro Ser Ile Leu Leu Leu Asp Glu Ala Thr Ser Ala Leu
545                 550                 555                 560
Asp Ala Glu Ser Glu Lys Ser Val Gln Glu Ala Leu Asp Arg Val Met
                565                 570                 575
Val Gly Arg Thr Thr Val Val Val Ala His Arg Leu Ser Thr Ile Arg
            580                 585                 590
Asn Ala Asp Val Ile Ala Val Gln Glu Gly Lys Ile Val Glu Thr
        595                 600                 605
Gly Ser His Asp Glu Leu Ile Ser Lys Pro Asp Ser Val Tyr Ala Ser
    610                 615                 620
Leu Val Gln Phe Gln Glu Thr Ser Ser Leu Gln His His Pro Ser Ile
625                 630                 635                 640
Gly Gln Leu Gly Arg Pro Pro Ser Ile Lys Tyr Ser Arg Glu Leu Ser
                645                 650                 655
Arg Thr Thr Thr Ser Phe Gly Ala Ser Phe Arg Ser Glu Lys Glu Ser
            660                 665                 670
Leu Gly Arg Ile Gly Val Asp Gly Met Glu Met Glu Lys Pro Lys His
        675                 680                 685
Val Ser Ala Arg Arg Leu Tyr Ser Met Val Gly Pro Asp Trp Met Tyr
    690                 695                 700
Gly Ile Val Gly Val Ile Gly Ala Phe Val Thr Gly Ser Gln Met Pro
705                 710                 715                 720
Leu Phe Ala Leu Gly Val Ser Gln Ala Leu Val Ala Phe Tyr Met Asp
                725                 730                 735
Trp Asn Thr Thr Gln His Glu Ile Lys Lys Ile Ser Leu Leu Phe Cys
            740                 745                 750
Gly Gly Ala Val Leu Thr Val Ile Phe His Ala Val Glu His Leu Cys
        755                 760                 765
Phe Gly Ile Met Gly Glu Arg Leu Thr Leu Arg Val Arg Glu Lys Met
    770                 775                 780
Phe His Ala Ile Leu Arg Asn Glu Ile Gly Trp Phe Asp Asp Met Asn
785                 790                 795                 800
Asn Thr Ser Ser Met Leu Ser Ser Arg Leu Glu Thr Asp Ala Thr Leu
                805                 810                 815
Leu Arg Thr Ile Val Val Asp Arg Ser Thr Ile Leu Leu Gln Asn Leu
            820                 825                 830
Ala Leu Val Val Ala Ser Phe Ile Ile Ala Phe Ile Leu Asn Trp Arg
        835                 840                 845
Ile Thr Leu Val Val Leu Ala Thr Tyr Pro Leu Ile Ile Ser Gly His
    850                 855                 860
Ile Ser Glu Lys Leu Phe Met Gln Gly Tyr Gly Gly Asn Leu Ser Lys
865                 870                 875                 880
Ala Tyr Leu Lys Ala Asn Thr Leu Ala Gly Glu Ala Val Gly Asn Ile
                885                 890                 895
Arg Thr Val Ala Ala Phe Cys Ser Glu Gln Lys Val Leu Asp Leu Tyr
            900                 905                 910
Ala Lys Glu Leu Val Glu Pro Ser Arg Arg Ser Leu Lys Arg Gly Gln
        915                 920                 925
Ile Ala Gly Ile Phe Tyr Gly Val Ser Gln Phe Phe Ile Phe Ser Ser
```

```
                930           935           940
Tyr Gly Leu Ala Leu Trp Tyr Gly Ser Val Leu Met Gly Gln Gly Leu
945           950           955           960
Ala Ser Phe Lys Ser Val Met Lys Ser Phe Met Val Leu Ile Val Thr
            965           970           975
Ala Leu Ala Met Gly Glu Thr Leu Ala Leu Ala Pro Asp Leu Leu Lys
        980           985           990
Gly Asn Gln Met Val Ala Ser Val Phe Glu Val Met Asp Arg Gln Thr
        995          1000          1005
Glu Val Ser Gly Asp Val Gly Glu Leu Asn Val Val Glu Gly
       1010          1015          1020
Thr Ile Glu Leu Arg Ser Val Glu Phe Ser Tyr Pro Ser Arg Pro
       1025          1030          1035
Asp Val Leu Ile Phe Lys Asp Phe Asn Leu Lys Val Arg Ala Gly
       1040          1045          1050
Lys Ser Ile Ala Leu Val Gly Gln Ser Gly Ser Gly Lys Ser Ser
       1055          1060          1065
Val Leu Ala Leu Ile Leu Arg Phe Tyr Asp Pro Ile Ala Gly Lys
       1070          1075          1080
Val Met Ile Asp Gly Lys Asp Ile Lys Lys Leu Lys Leu Lys Ser
       1085          1090          1095
Leu Arg Lys His Ile Gly Leu Val Gln Gln Glu Pro Ala Leu Phe
       1100          1105          1110
Ala Thr Ser Ile Tyr Glu Asn Ile Leu Tyr Gly Lys Glu Gly Ala
       1115          1120          1125
Ser Glu Ala Glu Val Phe Glu Ala Ala Lys Leu Ala Asn Ala His
       1130          1135          1140
Asn Phe Ile Ser Ala Leu Pro Glu Gly Tyr Ser Thr Lys Val Gly
       1145          1150          1155
Glu Arg Gly Ile Gln Leu Ser Gly Gly Gln Arg Gln Arg Ile Ala
       1160          1165          1170
Ile Ala Arg Ala Val Leu Lys Asn Pro Glu Ile Leu Leu Leu Asp
       1175          1180          1185
Glu Ala Thr Ser Ala Leu Asp Val Glu Ser Glu Arg Val Val Gln
       1190          1195          1200
Gln Ala Leu Asp Arg Leu Met Met Asn Arg Thr Thr Val Val Val
       1205          1210          1215
Ala His Arg Leu Ser Thr Ile Lys Asn Cys Asp Gln Ile Ser Val
       1220          1225          1230
Ile Gln Asp Gly Lys Ile Val Glu Gln Gly Thr His Ser Ser Leu
       1235          1240          1245
Ser Asp Asn Lys Asn Gly Ala Tyr Tyr Lys Leu Ile Asn Ile Gln
       1250          1255          1260
Gln Gln Gln Gln Arg Gln
       1265

<210> SEQ ID NO 7
<211> LENGTH: 3810
<212> TYPE: DNA
<213> ORGANISM: Citrullus lanatus

<400> SEQUENCE: 7
atgagaaacc atgggaatac agtttcatat gatcatgaag aagaaaatga agatgaagtt      60
agtatgaaga agaggaagaa tgatgaagaa gaagaagaag atgatgggaa gaagaagaag     120
```

```
aagaagaaga aagagcagca aaataaagtt gcttttata  aactctttgc ttttgctgat    180
ttttatgatt attttctcat gagttttggt tctattggag cttgtatcca tggtgcttct    240
gttcctgtct tcttcatttt ctttggaaaa ctcattaata tcattggcat ggcttatctt    300
ttccctgaag atgctgctcc caaagttgct aagtactctt tggattttct atatctcagt    360
gtggttatac tattttcatc atgggcagag gtggcttgtt ggatgcatag tggagagagg    420
caagcagcaa agatgagaat ggcttattta aaatcaatgt taaatcaaga cattagcctt    480
tttgacactg aagcttcaac tggtgaagtc attgctgcta ttactagtga cattgttatt    540
gttcaagatg ccatttctga gaaagtaggg aacttttttgc attatataag ccggtttata    600
tcagggttta ttatcggatt tgtgagggta tggcaaatca gtcttgtcac attatctatt    660
gtccctttga ttgcccttgc tggtggtctc tatgcatttg tcaccattgg tcttattgcc    720
aaagtaagaa aatcttatgt caaggctggt gagattgctg aagagatttt aggaaatgta    780
agaacagttc aagcctttgc tggggaagaa agagcagtaa atttatacaa aggagctctc    840
aagaatacct acaagtatgg tagaaaagca gggctggcta agggactggg cctgggatca    900
atgcattgtg tccttttctt gtcatgggct ctgctagttt ggtttaccag cattgttgtc    960
cacaagggca ttgccaatgg tggagactcc ttcaccacaa tgcttaatgt tgtcatttct   1020
ggcttgtcac ttgggcaggc cgcaccagac atttctgcct tgttcgagc  aaaggcagcg   1080 gcatatccta tttttcagat gatagagagg aacacagtta gcaaaagcag ctccaaaact   1140
ggccggaaac tgaataagct tgatggtcat attcaattca aggatgttaa tttcagctac   1200
ccatctcgtt tggatgtaat tatatttaat aagttatctc ttgatattcc tgcgggcaag   1260
attgtagctc ttgtgggagg aagtggatca ggaaagagca cagtgatatc tttgattgaa   1320
cgattctatg aacccctttc tggagagatt ctattggatg gtaataacat caaggagctg   1380
gatctcaagt ggctaaggca gcaaattggt ttggtcaatc aagagcctgc cctcttttgct  1440 acaagcatta gggagaacat tctatatgga aaagatgatg ctacccttga ggacataacg   1500
cgtgcagcca aactttctga ggctttatca tttataaaca atctccctga aagatttgaa   1560
actcaggttg gtgagagagg ggtccaatta tcaggggac  aaaaacaaag gattgcaata   1620
tctcgtgcaa tcgttaaaaa tccatcaatc ttgttgctgg atgaggcaac aagtgcacta   1680
gatgcagaat ctgaaaagag tgtacaagag gcactcgatc gcgtcatggt tggtcgaacg   1740
actgtagtgg tggctcatcg tttatctacc atacggaatg cagatgtgat tgctgtcgtt   1800
caagaaggaa agatagttga aaccggaagc catgatgagc tcatttcaaa gccgacagt   1860 gtctatgcat cacttgtcca gttccaagaa acatcatctc tgcaacacca tccctcgatt   1920
gggcagttgg gtcgaccacc tagtataaag tactctcgag aattatctcg cactacaacg   1980
agctttggtg caagttttcg ctccgagaaa gaatctcttg gacggattgg agttgatgga   2040
atggaaatga gaaaccaaa  gcatgtttca gcaagaagac tttactccat ggttggaccg   2100
gattggatgt atggcattgt cggcgtcatt ggagcattcg ttacaggatc ccagatgccc   2160
ctttttgctc ttggggtctc tcaggctctt gttgcatttt acatggactg gaatacaact   2220
caacatgaga tcaagaaaat tcattgcttt ttctgtggcg gtgcggtttt aactgtcatt   2280
tttcatgcag ttgagcatct ttgttttgga attatgggag agcgacttac tcttcgagtt   2340
cgagaaaaga tgttccatgc tattctgaga aacgagatag gatggttcga tgatatgaac   2400
aacacaagtt ctatgctttc atcacgtcta gaaactgatg caactttatt acgaactatt   2460
```

-continued

```
gttgtcgacc gctctacaat tcttctgcag aatctagctt tggtcgttgc atcgttcatc    2520
attgctttca ttttgaattg gagaatcact ctagttgtcc tggccactta tccattgatc    2580
attagcggtc acattagcga gaaacttttt atgcaaggct acggtggaaa tttgagcaaa    2640
gcatacctga aagccaatac actggccggt gaggcagttg caacattag gactgttgct     2700
gcattttgtt ctgagcagaa ggttcttgat ctatatgcta aggagctcgt tgagccctcg    2760
agacgttcgc ttaaacgtgg acagattgct ggaatatttt atggtgtctc ccagttcttc    2820
atcttttcat cttacggtct ggccttgtgg tacggttcgg tcttgatggg acaggggctt    2880
gctagcttca atctgttat gaaatcattc atggttttga tagtaactgc cttagcaatg     2940
ggtgaaactt tggcattggc ccctgatctt ttaaagggaa accagatggt ggcatccgtg    3000
tttgaggtga tggatcgaca gacagaggtg tcggtgatg ttggtgaaga gctaaatgtg     3060
gtggagggta ccattgagct gaggagtgtt gagttcagct atccatcaag accagatgtt    3120
ttgatcttca aagatttcaa tcttaaagtg agagcaggca agagtatagc cttagttggg    3180
caaagcggtt cggggaaaag ctcggttcta gctcttattc tgcgattta cgatccaatt     3240
gctgggaagg tgatgattga tggaaaagat attaaaaaac tgaagctcaa atctctcaga    3300
aagcacatcg gcctcgtcca acaggaaccg gctcttttg ccacgtcaat ttacgagaac     3360
attctttatg ggaagaagg agcttcagaa gccgaagtat cgaagcagc gaaactcgcc      3420
aatgctcata acttcatcag tgctcttcct gaaggctact caacaaagt tggggaaga     3480
gggatccaac tttcgggtgg ccaacgacag aggatcgcca ttgcaagagc agtcctgaag    3540
aacccggaaa tactactact agacgaagct acgagtgctc tcgatgtcga atcggaacgt    3600
gtggttcagc aagccttaga cagattgatg atgaacagaa caactgtggt ggttgcacat    3660
aggctttcta ccattaaaaa ctgtgaccaa atctcagtga ttcaagatgg gaagattgta    3720
gaacaaggaa ctcattcaag ccttttccgac aacaaaaatg gagcttatta caagttaatc   3780
aacatccaac aacagcaaca aagacagtga                                      3810
```

<210> SEQ ID NO 8
<211> LENGTH: 8691
<212> TYPE: DNA
<213> ORGANISM: Citrullus lanatus

<400> SEQUENCE: 8

```
atgagaaacc atgggaatac agtttcatat gatcatgaag aagaaaatga agatgaagtt     60
agtatgaaga gaggaagaa tgatgaagaa gaagaagaag atgatgggaa gaagaagaag    120
aagaagaaga aagagcagca aaataaagtt gcttttttata aactctttgc ttttgctgat    180
ttttatgatt attttctcat gagttttggt tctattggag cttgtatcca tggtgcttct    240
gttcctgtct tcttcatttt ctttggaaaa ctcattaata tcattggcat ggcttatctt    300
ttccctgaag atgctgctcc caaagttgct aaggttcctt cttttaaatt ctctttattt    360
tctcctcatt tctatatttt aaccaaatta ttttttttct ttaaaactac gtctcgtttc    420
gtataaccat ttcatttttg cttttttggta tttcaaaagt aagctacttc tatctataag    480
ttttttttg ttttgtttc cacttttcac taatatttg aaaaatcatg ccgaattccg       540
aaaacgaaaa gaaaaatagt ttccgaaaat tgattccgt tagaatttaa ctaagagttc     600
aagtgttttt tcaaatcata taagaagtta ctttgaagtt tatataaaat taaaaaacaa    660
aaaattaaat cgttaccgaa cttatagatg aaagtaacta gacattactt caatctataa    720
gtttctttgt tttattttcc acttttcact gttattttga aaaccatgc cgaattctaa     780
```

```
aaactaaaaa aaaaaaaaag tagtttccaa aaaaaacttg tttttgttag aatttgacta     840
aaaattcaag tgttcctatg aaatttatat aaaacaaaaa atgaaaaact aaggtctagt     900
ctggtaacca tttcgttttt tgtttttgtt tttgaaaatt aagcatattt tctcctcatt     960
tcttacattg ttttgcatct ctcttaagta gaatagttga aattctttgcc aaattctaaa   1020 aacaagagca agttttaaa aacaatctttt ttttagtttt caaattttgg ctttggtttt    1080
ttaaacattg gtaaaagta aataacaaat gaataaattt gaaggtggaa ctagggtata    1140
taggcttact tttaaaaaac aaaaacaaaa tgattacaaa accgggccta aattagtact   1200
aaatagagcc tattatttt agtttagtct acaaaacttg gatggaattg taaaaccatt    1260
ttgaaaatta aataacaaaa taaagaaact aattataggt tggtttccaa acttaaattt   1320
caaaaattaa aaaaacacc cttaattaac tttgggagat aattgaagat ctatcaatat    1380 tttttttta aaaattgat tttattttaa tttttttttg gcagtactct ttggattttc     1440
tatatctcag tgtggttata ctatttttcat catgggcagg tatgttaatt attattatta  1500 ttattttaa aaattttagt tatacttgat attattgttt aaaattttgg aattaattaa    1560
ttaaatgtag aggtggcttg ttggatgcat agtggagaga ggcaagcagc aaagatgaga   1620
atggcttatt taaaatcaat gttaaatcaa gacattagcc ttttttgacac tgaagcttca  1680 actggtgaag tcattgctgc tattactagt gacattgtta ttgttcaaga tgccatttct  1740
gagaaagtat gattctcttt cttctcccca aaaccctaat tttcatatcc atcgtctaac   1800
tattttcctt ttgaatctat cgacttcata tcattcttaa atgaagttac ttttcaaaac  1860
tactcctaaa gtagaaaatct aattaggact tcaaacagtg tggcgataat cctagaatgg 1920
tgtgtcaatt gaaaattttg gtttaggtta tcatcatacc gttttcata tcctagtatc   1980 catatgacat tccaaagaat ttattctccc ttgtaatttg gaattgttta gcaactttta  2040
aaagaataaa aatgttttg aaataaatga caaaattgaa tgaaatattt attaattaat    2100
ttataaaaat ttaatgcaat tgcagatgga agggagagtg tatttatatt tgacataaaa  2160
aagaaagtaa agttatgaat gaacctgaca tttcctttc attatgcttt gacaaaagac  2220
tatggagtaa atgcaatggt tgagaacatt aaataagtca ccgctgagtt tggtaaggtt  2280
gctttattac ccctttttcca tctcggtttt atcttattct ttttttttt atacaacaat   2340 tacaactcca agaaagaaaa ttactaaacc aaacttactt ttagagaatt tttatctcct  2400
tctcaattga tagaaattta gttttttcatt attttacttt ggctaaatgt tcccatttgt  2460
ttaagaaata ttatattctt cgagcgttaa acgtaagtct tttaaaattt cggataaaac  2520
tttagattga aatgttgtgg cagtgaccta aaatgtcgtg gcaattgtaa tctttatttt  2580
aaatactacc acatcattga tttgcaactt tgaaaaaaaa tagggagtgt ttttgaaata  2640
aagtaaaagg tccaaatatt gttttcaaat tgctctaaag ccttttgaaa aggagtgttt  2700 ttttctttt ttttcctatt tgaccagaaa atttcaattt tgttttacc caattgcaaa    2760 tttaactttg attaatcagt taaaatgata aaattgttga aaatattttt aattataaca  2820
aaatgtcact aattatctat gatagatatt gtctatcatt ttctatcccc gtctattagt  2880
acattttgct atttagaaac aacccttta actttctcat ataaatagat ggtgaggttt   2940
tgccccaatt ttagttgtcg atgcattcaa ttttctacaa ttattgctat aactcaccta   3000
ttaataatgg gccttcagta tttattatgt gcttcgtccc caacccaaca gtctattcct  3060
cacaaagcta acttaacttt tgagatgcaa agtaataaaa ctgctgattc ttgaacttgc   3120
```

```
aaaatttaca agaccaaaac ttatgtataa tgtgttatta gaagcattat tcttatatct    3180
ttagaattgt aaggtttggt tttaattcct ctactttgtt ctatcttgaa ttaatgagtt    3240
gcggttaagg tgtttgatga aatgcctgag aagttttgt gggttctgca ggtagggaac     3300
tttttgcatt atataagccg gtttatatca gggtttatta tcggatttgt gagggtatgg    3360
caaatcagtc ttgtcacatt atctattgtc cctttgattg cccttgctgg tggtctctat    3420
gcatttgtca ccattggtct tattgccaaa gtaagaaaat cttatgtcaa ggctggtgag    3480
attgctgaag aggttagcac tttctctgat ttactcatgt agacattgtt ttggttaaat    3540
atacctaaac tcgttatctt actcatgtag acattgtttc ggttaaatag tctaggtctg    3600
gatcttggat tttcttgtgt taatatttgt cgatatgtga cgagagtatt tagagatgtt    3660
taataacatt atggaaatgt ttatatctta ttttgatgt caactaggaa agtagataca     3720
ttatagttgt gttcaataaa ataaagggaa aattaaataa caatttatat ccttaaaact    3780
ttcgattacc tttgaaaatc ctctatgcat tattttctcaa acatgtgtag acttttttcaa  3840 atgtcggttt tacaaaatag acgtgtatgg acaattctca aaggaaatta tgtataagag    3900
tctaaattga ttcatttaaa agttttgggg taattgatac aattataagt tttactcaag    3960
gttttcccaa atagaatgta atggaggtg cgtatattga tatacttaca aaagttaaag      4020
gttcaaattg atacaatgat tagtttaagg tttaaattga tacaacgcct aaagtttaag    4080
ggtataaatt gatgctttcc ctgaaataag taaatgaaac ttagttggat aaatggtaac    4140
caacttcttt ctttgcttaa gagctctata ttggttttaa ctatctttc atcacccctt     4200 acccttctgt ttttgtcctt taagatttta ggaaatgtaa gaacagttca agcctttgct    4260
ggggaagaaa gagcagtaaa tttatacaaa ggagctctca agaataccta caagtatggt    4320
agaaaagcag ggctggctaa gggactgggc ctgggatcaa tgcattgtgt ccttttcttg    4380
tcatgggctc tgctagtttg gtttaccagc attgttgtcc acaagggcat tgccaatggt    4440
ggagactcct tcaccacaat gcttaatgtt gtcatttctg gcttgtaagt ctttcagctt    4500
atcttaatat cgaatcgtct gttaattaca ttccatttcc aattctgtgc tacacattgt    4560
agaaatagaa catccccaca cttacataaa atgggttgct tactttagct tgaacattga    4620 aaccagtat tcaaagtatc caaggtcttt atttcctttg tgcaaagtat agaactatcc     4680
attttggatt tgtaaatgtg atggaattag gcaaatatgt ataagataaa gtataatata   4740
tcaagctttt ccacagtatg atcttcattt agccgatggt gttcatcaag ctactaaata    4800
aggattgata gatggtatgg atttgaagac tttcaaactt caaaacactt tctagtaaaa    4860
aattctctgt ttacccagaa tttaagtgtg ttaaaaagtc cactagctac cccaactttc    4920
gaaatgagtg ctatcttaat tctaatgttc tggtaatcca agcttcttgt taatggttcc    4980
acttgtttca ggtcatttca ttttaatgcc tttgtaattc aaaggtaggt tattaatggt    5040
tacattgcct caggtcactt gggcaggccg caccagacat ttctgccttt gttcgagcaa    5100
aggcagcggc atatcctatt tttcagatga tagagaggaa cacagttagc aaaagcagct    5160
ccaaaactgg ccggaaactg aataagcttg atggtcatat tcaattcaag gatgttaatt    5220
tcagctaccc atctcgtttg gatgtaatta tatttaataa gttatctctt gatattcctg    5280
cgggcaagat tgtagctctt gtgggaggaa gtggatcagg aaagagcaca gtgatatctt    5340
tgattgaacg attctatgaa cccctttctg gagagattct attggatggt aataacatca    5400
aggagctgga tctcaagtgg ctaaggcagc aaattggttt ggtcaatcaa gagcctgccc    5460 tcttgctac aagcattagg gagaacattc tatatggaaa agatgatgct acccttgagg     5520
```

```
acataacgcg tgcagccaaa ctttctgagg ctttatcatt tataaacaat ctccctgaaa    5580
gatttgaaac tcaggtatta ttatctatct ctgagaacta accatgagaa tttgtgttgg    5640
taaaggttca aagctttaaa aagagacatt gattccaaaa aaataacttg gcaagtttta    5700
aacttaaaaa aaactgtctt ctaataatta attaaatagt tgctattagt tcatctaatg    5760
ttttgttcat tagagtggaa aatcgcagtc ggattataag catagtagaa aataataact    5820
ctagattaaa tgttttgttc taggttggtg agagaggggt ccaattatca ggggacaaa    5880 aacaaaggat tgcaatatct cgtgcaatcg ttaaaaatcc atcaatcttg ttgctggatg    5940
aggcaacaag tgcactagat gcagaatctg aaaagagtgt acaagaggca ctcgatcgcg    6000
tcatggttgg tcgaacgact gtagtggtgg ctcatcgttt atctaccata cggaatgcag    6060
atgtgattgc tgtcgttcaa gaaggaaaga tagttgaaac cggaagccat gatgagctca    6120
tttcaaagcc ggacagtgtc tatgcatcac ttgtccagtt ccaagaaaca tcatctctgc    6180
aacaccatcc ctcgattggg cagttgggtc gaccacctag gtattccatt ctcactttag    6240
cttacaatac gatgattttt tctatgaaac acacatttta tagtttcatt ttttatgata    6300
ggattagcca ataataataa tatgcatcaa acacccttag atgctacatt ttgattaaaa    6360
aatcaagtta cttattgcta aactgttttt aaattcatcc aacttgtagt ataaagtact    6420
ctcgagaatt atctcgcact acaacgagct ttggtgcaag ttttcgctcc gagaaagaat    6480
ctcttggacg gattggagtt gatggaatgg aaatggagaa accaaagcat gtttcagcaa    6540
gaagacttta ctccatggtt ggaccggatt ggatgtatgg cattgtcggc gtcattggag    6600
cattcgttac aggatcccag atgccccttt ttgctcttgg ggtctctcag gctcttgttg    6660
cattttacat ggactggaat acaactcaac atgagatcaa gaaaatttca ttgctttttct    6720 gtggcggtgc ggttttaact gtcattttc atgcagttga gcatctttgt tttggaatta    6780
tgggagagcg acttactctt cgagttcgag aaaagatgtt ccatggtatc ctgcaatctt    6840
tacacctaag tgccttttat tttcaagtca ttcaattttc tctaagcaat ttttgtttgg    6900
ttgcagctat tctgagaaac gagataggat ggttcgatga tatgaacaac acaagttcta    6960
tgctttcatc acgtctagaa actgatgcaa ctttattacg aactattgtt gtcgaccgct    7020
ctacaattct tctgcagaat ctagctttgg tcgttgcatc gttcatcatt gctttcattt    7080
tgaattggag aatcactcta gttgtcctgg ccacttatcc attgatcatt agcggtcaca    7140
ttagcgaggt tttctatcat aacttctcta aattacttat ttctttccct gaatttcaaa    7200
tatttcctca tgaaactgct cttttccatt gtgttttaga aactttttat gcaaggctac    7260
ggtggaaatt tgagcaaagc atacctgaaa gccaatacac tggccggtga ggcagttggc    7320
aacattagga ctgttgctgc attttgttct gagcagaagg ttcttgatct atatgctaag    7380
gagctcgttg agccctcgag acgttcgctt aaacgtggac agattgctgg aatatttttat    7440 ggtgtctccc agttcttcat cttttcatct tacggtctgg ccttgtggta tgtgatttaa    7500
gaaactattt tagactactt gtcataaata tttgaataga aattagaatc aatccgaatt    7560
aattttatga atgattcaac tatcttaagc atgtgctatt atgcaggtac ggttcggtct    7620
tgatgggaca ggggcttgct agcttcaaat ctgttatgaa atcattcatg gttttgatag    7680
taactgcctt agcaatgggt gaaactttgg cattggcccc tgatctttta aagggaaacc    7740
agatggtggc atccgtgttt gaggtgatgg atcgacagac agaggtgtcg ggtgatgttg    7800
gtgaagagct aaatgtggtg gagggtacca ttgagctgag gagtgttgag ttcagctatc    7860
```

```
catcaagacc agatgttttg atcttcaaag atttcaatct taaagtgaga gcaggcaaga    7920
gtatagcctt agttgggcaa agcggttcgg ggaaaagctc ggttctagct cttattctgc    7980
gattttacga tccaattgct gggaaggtga tgattgatgg taagttttct caacaatctg    8040
ctcacttttg atagtaactg cactaccata ttctacattt ttacaagtaa aattctagat    8100
catcttttca agttttgatt aacagagctt ttatatcttg caggaaaaga tattaaaaaa    8160
ctgaagctca aatctctcag aaagcacatc ggcctcgtcc aacaggaacc ggctcttttt    8220
gccacgtcaa tttacgagaa cattctttat gggaagaag gagcttcaga agccgaagta     8280
ttcgaagcag cgaaactcgc caatgctcat aacttcatca gtgctcttcc tgaaggctac    8340
tcaacaaaag ttggggaaag agggatccaa ctttcgggtg ccaacgaca gaggatcgcc     8400 attgcaagag cagtcctgaa gaacccggaa atactactac tagacgaagc tacgagtgct    8460
ctcgatgtcg aatcggaacg tgtggttcag caagccttag acagattgat gatgaacaga    8520
acaactgtgg tggttgcaca taggctttct accattaaaa actgtgacca aatctcagtg    8580
attcaagatg ggaagattgt agaacaagga actcattcaa gcctttccga caacaaaaat    8640
ggagcttatt acaagttaat caacatccaa caacagcaac aaagacagtg a             8691

<210> SEQ ID NO 9
<211> LENGTH: 1257
<212> TYPE: PRT
<213> ORGANISM: Solanum lycopersicum

<400> SEQUENCE: 9

Met Ser Gln Gln Gln Ser His Ala Leu Ser Val Asp Ser Ser Lys Ile
1               5                   10                  15

Ser Lys Met Asn Gln Lys Asn Asn Glu Glu Glu Glu Arg Lys Lys
            20                  25                  30

Lys Thr His Lys Lys Val Ser Leu Leu Lys Leu Phe Ser Phe Ala Asp
        35                  40                  45

Ser Tyr Asp Tyr Leu Leu Met Phe Leu Gly Ser Ile Gly Ala Cys Leu
    50                  55                  60

His Gly Ala Ser Val Pro Val Phe Phe Ile Phe Phe Gly Lys Met Ile
65                  70                  75                  80

Asn Ile Ala Gly Leu Ala Tyr Leu Phe Pro Ala Gln Thr Ser His Lys
                85                  90                  95

Ile Ala Lys Tyr Ser Leu Asp Phe Val Tyr Leu Ser Val Val Ile Leu
            100                 105                 110

Phe Ala Ser Trp Ile Glu Val Ala Cys Trp Met His Ser Gly Glu Arg
        115                 120                 125

Gln Ala Ala Lys Ile Arg Met Ala Tyr Leu Lys Ser Met Leu Asn Gln
    130                 135                 140

Asp Ile Ser Leu Phe Asp Thr Glu Ala Ser Thr Gly Glu Val Ile Ala
145                 150                 155                 160

Ala Ile Thr Ser Asp Ile Ile Val Gln Asp Ala Ile Ser Glu Lys
                165                 170                 175

Ala Gly Asn Phe Leu His Tyr Ile Ser Arg Phe Leu Ala Gly Phe Thr
            180                 185                 190

Ile Gly Phe Ile Arg Val Trp Gln Ile Ser Leu Val Thr Leu Ser Ile
        195                 200                 205

Val Pro Leu Ile Ala Leu Ala Gly Gly Ile Tyr Ala Tyr Val Thr Ile
    210                 215                 220

Gly Leu Ile Ala Arg Val Arg Lys Ser Tyr Ile Lys Ala Gly Glu Ile
```

-continued

```
        225                 230                 235                 240
Ala Glu Glu Val Val Ala Asn Ile Arg Thr Val Gln Ala Phe Thr Gly
                245                 250                 255

Glu Glu Asn Ala Val Lys Ser Tyr Lys Gly Ala Leu Leu Asn Thr Tyr
                260                 265                 270

Lys Tyr Gly Arg Lys Ala Gly Phe Ala Lys Gly Leu Gly Leu Gly Thr
                275                 280                 285

Leu His Cys Ile Leu Phe Leu Ser Trp Ser Leu Leu Val Trp Phe Thr
                290                 295                 300

Ser Ile Val Val His Lys Asn Ile Ala Asn Gly Gly Asp Ser Phe Thr
305                 310                 315                 320

Thr Met Leu Asn Val Val Ile Ala Gly Leu Ser Leu Gly Gln Ala Ala
                325                 330                 335

Pro Asp Ile Thr Ala Phe Leu Arg Ala Lys Ser Ala Ala Tyr Pro Ile
                340                 345                 350

Phe Glu Met Ile Glu Arg Asp Thr Ile Ser Lys Thr Ser Ser Lys Ser
                355                 360                 365

Gly Gln Lys Leu Ser Lys Val Asp Gly His Ile Gln Phe Lys Asp Val
                370                 375                 380

Cys Phe Ser Tyr Pro Ser Arg Pro Asp Val Val Ile Phe Asp Lys Leu
385                 390                 395                 400

Ser Leu Asp Ile Pro Ser Gly Lys Ile Val Ala Leu Val Gly Gly Ser
                405                 410                 415

Gly Ser Gly Lys Ser Thr Val Ile Ser Leu Ile Glu Arg Phe Tyr Glu
                420                 425                 430

Pro Leu Ser Gly Gln Ile Leu Leu Asp Gly Phe Asp Ile Arg His Leu
                435                 440                 445

Asp Leu Lys Trp Leu Arg Gln Gln Ile Gly Leu Val Asn Gln Glu Pro
                450                 455                 460

Ala Leu Phe Ala Thr Thr Ile Arg Glu Asn Ile Leu Tyr Gly Lys Ser
465                 470                 475                 480

Asp Ala Ser Leu Glu Asp Ile Ala Arg Ala Ala Lys Leu Ser Glu Ala
                485                 490                 495

Met Thr Phe Ile Asn Asn Leu Pro Asp Arg Phe Glu Thr Gln Val Gly
                500                 505                 510

Glu Arg Gly Val Gln Leu Ser Gly Gly Gln Lys Gln Arg Ile Ala Ile
                515                 520                 525

Ser Arg Ala Ile Val Lys Asn Pro Ser Ile Leu Leu Leu Asp Glu Ala
                530                 535                 540

Thr Ser Ala Leu Asp Ala Glu Ser Glu Lys Ser Val Gln Asp Ala Leu
545                 550                 555                 560

Asp Arg Val Met Val Gly Arg Thr Thr Val Ile Val Ala His Arg Leu
                565                 570                 575

Ser Thr Ile Arg Asn Ala Asp Ile Ile Ala Val Val Asn Asn Gly Lys
                580                 585                 590

Ile Val Glu Thr Gly Ser His Glu Glu Leu Ile Ser Lys Pro Asn Ser
                595                 600                 605

Ala Tyr Ala Ser Leu Val Gln Leu Gln Gln Ala Ser Ser His Leu
                610                 615                 620

His Pro Ser Gln Glu Pro Thr Met Gly Arg Pro His Ser Ile Arg Tyr
625                 630                 635                 640

Ser Arg Glu Leu Ser Arg Thr Thr Thr Arg Ser Arg Gly Ala Ser Phe
                645                 650                 655
```

```
Arg Ser Glu Lys Ser Val Ser Gly Ile Gly Ala Gly Asp Val Glu Asp
            660                 665                 670

Val Lys Ser Pro Asn Val Ser Ala Gly Arg Leu Tyr Ser Met Ile Arg
            675                 680                 685

Pro Glu Trp His Tyr Gly Val Ile Gly Thr Ile Cys Ala Phe Ile Ala
            690                 695                 700

Gly Ala Gln Met Pro Leu Phe Ala Leu Gly Val Ser Gln Ala Leu Val
705                 710                 715                 720

Ser Tyr Tyr Met Asp Trp Asp Thr Thr Arg His Glu Val Lys Lys Ile
                    725                 730                 735

Cys Phe Leu Phe Cys Val Gly Ala Val Leu Thr Val Val His Ala
                740                 745                 750

Ile Ala His Thr Cys Phe Gly Ile Ile Gly Glu Arg Leu Thr Leu Arg
                755                 760                 765

Val Arg Glu Met Met Phe Ser Ala Met Leu Arg Asn Glu Ile Gly Trp
            770                 775                 780

Phe Asp Glu Val Asn Asn Ser Ser Thr Leu Ala Ser Arg Leu Glu
785                 790                 795                 800

Ser Asp Ala Thr Leu Leu Arg Thr Val Val Asp Arg Ser Thr Ile
                    805                 810                 815

Leu Leu Gln Asn Val Gly Leu Val Ala Thr Ser Phe Ile Ile Ala Phe
            820                 825                 830

Ile Leu Asn Trp Arg Leu Thr Leu Val Val Met Ala Met Tyr Pro Leu
            835                 840                 845

Ile Val Ser Gly His Ile Ser Glu Lys Leu Phe Met Ser Gly Phe Gly
            850                 855                 860

Gly Asp Leu Ser Lys Ala Tyr Leu Arg Ala Asn Met Phe Ala Gly Glu
865                 870                 875                 880

Ala Val Ser Asn Ile Arg Thr Val Ala Ala Phe Cys Ala Glu Lys
                    885                 890                 895

Val Thr Asp Leu Tyr Ala Arg Glu Leu Val Glu Pro Ala Lys His Ser
            900                 905                 910

Phe Arg Arg Gly Gln Thr Ala Gly Ile Leu Tyr Gly Val Ser Gln Phe
            915                 920                 925

Phe Ile Phe Ser Ser Tyr Ala Leu Ala Leu Trp Tyr Gly Ser Val Leu
            930                 935                 940

Met Gly Lys Glu Leu Thr Ser Phe Lys Ala Val Met Lys Ser Phe Met
945                 950                 955                 960

Val Leu Ile Val Thr Ala Leu Ala Met Gly Glu Thr Leu Ala Met Ala
                    965                 970                 975

Pro Asp Leu Ile Lys Gly Asn Gln Met Val Ala Ser Val Phe Glu Val
                980                 985                 990

Leu Asp Arg Lys Thr Glu Ile Val Thr Asp Ser Gly Glu Glu Leu Thr
            995                 1000                1005

Val Val Glu Gly Thr Ile Glu Phe Lys Asp Val Glu Phe Cys Tyr
            1010                1015                1020

Pro Ala Arg Pro Asp Val His Ile Phe Arg Asp Phe Asn Met Arg
            1025                1030                1035

Val His Ala Gly Lys Ser Met Ala Ile Val Gly Gln Ser Gly Ser
            1040                1045                1050

Gly Lys Ser Ser Val Leu Ala Leu Ile Leu Arg Phe Tyr Asp Pro
            1055                1060                1065
```

```
Ile Ser Gly Lys Val Ile Ile Asp Gly Lys Asp Ile Arg Lys Leu
    1070                1075                1080

Lys Leu Asn Ser Leu Arg Lys His Ile Gly Leu Val Gln Gln Glu
    1085                1090                1095

Pro Ala Leu Phe Ala Thr Thr Ile Tyr Glu Asn Ile Leu Tyr Gly
    1100                1105                1110

Lys Glu Gly Ala Ser Glu Ala Glu Val Ile Gln Ala Ala Lys Leu
    1115                1120                1125

Ala Asn Ala His Ser Phe Ile Ser Ala Leu Pro Asp Gly Tyr Ser
    1130                1135                1140

Thr Gln Val Gly Glu Arg Gly Val Gln Leu Ser Gly Gly Gln Lys
    1145                1150                1155

Gln Arg Val Ala Ile Ala Arg Ala Val Leu Lys Asn Pro Glu Ile
    1160                1165                1170

Leu Leu Leu Asp Glu Ala Thr Ser Ala Leu Asp Val Glu Ser Glu
    1175                1180                1185

Arg Ile Val Gln Gln Ala Leu Asp Arg Leu Met Arg Asn Arg Thr
    1190                1195                1200

Thr Val Ile Val Ala His Arg Leu Ser Thr Ile Lys Asp Ala Asp
    1205                1210                1215

Gln Ile Ser Val Leu Gln Asp Gly Lys Ile Val Asp Gln Gly Thr
    1220                1225                1230

His Ser Ala Leu Ile Glu Asn Arg Asp Gly Ala Tyr Phe Lys Leu
    1235                1240                1245

Ile His Leu Gln Gln Gln Gln Gln
    1250                1255

<210> SEQ ID NO 10
<211> LENGTH: 1251
<212> TYPE: PRT
<213> ORGANISM: Capsicum annuum

<400> SEQUENCE: 10

Met Ser His Gln Gln Ser His Ala Leu Ser Val Asp Ser Ser Gly Ile
1               5                   10                  15

Ser Lys Met Lys Gln Lys Asn Ile Gly Asp Glu Arg Lys Lys Pro
            20                  25                  30

Lys Lys Val Ser Leu Leu Lys Leu Phe Ser Phe Ala Asp Ser Tyr Asp
        35                  40                  45

Tyr Leu Leu Met Phe Leu Gly Ser Ile Gly Ala Cys Leu His Gly Ala
    50                  55                  60

Ser Val Pro Val Phe Phe Ile Phe Gly Lys Leu Ile Asn Ile Ala
65                  70                  75                  80

Gly Leu Ala Tyr Leu Phe Pro Ala Leu Ala Ser His Lys Val Ala Lys
            85                  90                  95

Tyr Ser Leu Asp Phe Val Tyr Leu Ser Val Val Ile Leu Phe Ala Ser
            100                 105                 110

Trp Ile Glu Val Ala Cys Trp Met His Ser Gly Glu Arg Gln Ala Ala
        115                 120                 125

Lys Ile Arg Met Ala Tyr Leu Lys Ser Met Leu Asn Gln Asp Ile Ser
    130                 135                 140

Leu Phe Asp Thr Glu Ala Ser Thr Gly Glu Val Ile Ser Ala Ile Thr
145                 150                 155                 160

Ser Asp Ile Ile Val Val Gln Asp Ala Ile Ser Glu Lys Ala Gly Asn
            165                 170                 175
```

```
Phe Met His Tyr Ile Ser Arg Phe Leu Ala Gly Phe Thr Ile Gly Phe
            180                 185                 190

Ile Arg Val Trp Gln Ile Ser Leu Val Thr Leu Ser Ile Val Pro Leu
        195                 200                 205

Ile Ala Leu Ala Gly Gly Ile Tyr Ala Phe Val Thr Ile Gly Leu Ile
    210                 215                 220

Ala Arg Val Arg Lys Ser Tyr Ile Asn Ala Gly Glu Val Ala Glu Glu
225                 230                 235                 240

Val Ile Ala Asn Ile Arg Thr Val Gln Ala Phe Ala Gly Glu Glu Lys
                245                 250                 255

Ala Val Lys Ser Tyr Lys Gly Val Leu Leu Asn Thr Tyr Gln Tyr Gly
            260                 265                 270

Lys Lys Ala Gly Leu Ala Lys Gly Leu Gly Leu Gly Thr Leu His Cys
        275                 280                 285

Val Leu Phe Leu Ser Trp Ser Leu Leu Val Trp Phe Thr Ser Ile Val
    290                 295                 300

Val His Lys Asn Ile Ala Asn Gly Gly Glu Ser Phe Thr Thr Met Leu
305                 310                 315                 320

Asn Val Val Ile Ala Gly Leu Ser Leu Gly Gln Ala Ala Pro Asp Ile
                325                 330                 335

Thr Ala Phe Leu Arg Ala Lys Ser Ala Ala Tyr Pro Ile Phe Glu Met
            340                 345                 350

Ile Glu Arg Asp Thr Ile Ser Lys Ile Ser Ser Lys Ser Gly His Gln
        355                 360                 365

Leu Ser Glu Val Asp Gly His Ile Gln Phe Lys Asp Val Cys Phe Ser
    370                 375                 380

Tyr Pro Ser Arg Pro Asp Val Val Ile Phe Asp Lys Phe Ser Leu Asp
385                 390                 395                 400

Ile Pro Ser Gly Lys Ile Val Ala Leu Val Gly Gly Ser Gly Ser Gly
                405                 410                 415

Lys Ser Thr Val Ile Ser Leu Ile Glu Arg Phe Tyr Glu Pro Leu Ser
            420                 425                 430

Gly His Ile Leu Leu Asp Gly Ser Asp Ile Arg His Leu Asp Leu Lys
        435                 440                 445

Trp Leu Arg Gln Gln Ile Gly Leu Val Asn Gln Glu Pro Ala Leu Phe
    450                 455                 460

Ala Thr Thr Ile Arg Glu Asn Ile Leu Tyr Gly Lys Ser Asp Ala Ser
465                 470                 475                 480

Leu Glu Asp Ile Ala Arg Ala Ala Lys Leu Ser Glu Ala Met Thr Phe
                485                 490                 495

Ile Asn Asn Leu Pro Asp Arg Leu Glu Thr Gln Val Gly Glu Arg Gly
            500                 505                 510

Val Gln Leu Ser Gly Gly Gln Lys Gln Arg Ile Ala Ile Ser Arg Ala
        515                 520                 525

Ile Val Lys Asn Pro Ser Ile Leu Leu Leu Asp Glu Ala Thr Ser Ala
    530                 535                 540

Leu Asp Ala Glu Ser Glu Lys Ser Val Gln Asp Ala Leu Asp Arg Val
545                 550                 555                 560

Met Val Gly Arg Thr Thr Val Ile Val Ala His Arg Leu Ser Thr Ile
                565                 570                 575

Arg Asn Val Asp Ile Ile Ala Val Val Asn Asn Gly Lys Ile Val Glu
            580                 585                 590
```

```
Thr Gly Ser His Glu Glu Leu Ile Ser Lys Pro Asn Gly Ala Tyr Ala
            595                 600                 605

Ser Leu Val Gln Leu Gln Gln Ala Ala Ser Ser His Leu Gln Glu Pro
    610                 615                 620

Thr Met Gly Arg Pro Leu Ser Ile Arg Tyr Ser Arg Glu Leu Ser Arg
625                 630                 635                 640

Thr Arg Thr Gln Ser His Gly Ala Ser Phe Arg Ser Glu Lys Ser Val
                645                 650                 655

Ser Gly Ile Gly Asp Ala Gly Val Glu Asp Val Lys Glu Pro Asn Ile
            660                 665                 670

Ser Leu Arg Arg Leu Tyr Ser Met Ile Arg Pro Glu Trp His Tyr Gly
            675                 680                 685

Val Ile Gly Thr Ile Ser Ala Phe Ile Ala Gly Ser Gln Met Pro Leu
            690                 695                 700

Phe Ala Leu Gly Val Ser Gln Ala Leu Val Ser Tyr Tyr Met Asp Trp
705                 710                 715                 720

Asp Thr Thr Arg His Glu Val Lys Lys Ile Ser Ile Leu Phe Cys Ile
                725                 730                 735

Gly Ala Val Leu Ser Val Ile Val Tyr Ala Ile Ala His Thr Cys Phe
            740                 745                 750

Gly Ile Ile Gly Ala Arg Leu Thr Leu Arg Val Arg Glu Met Met Phe
            755                 760                 765

Ser Ala Met Leu Arg Asn Glu Ile Gly Trp Phe Asp Glu Met Asn Asn
    770                 775                 780

Ser Ser Ser Ser Leu Ala Ser Arg Leu Glu Ser Asp Ala Thr Leu Leu
785                 790                 795                 800

Arg Thr Val Val Val Asp Arg Ser Thr Ile Leu Leu Gln Asn Val Gly
                805                 810                 815

Leu Val Phe Thr Ser Phe Val Ile Ala Phe Met Leu Asn Trp Arg Leu
            820                 825                 830

Thr Leu Ile Val Met Ala Met Tyr Pro Leu Ile Ile Ser Gly His Ile
            835                 840                 845

Ser Glu Lys Leu Phe Met Ala Gly Phe Gly Gly Asp Leu Ser Lys Ala
    850                 855                 860

Tyr Leu Arg Ala Asn Met Phe Ala Gly Glu Ala Val Ser Asn Ile Arg
865                 870                 875                 880

Thr Val Ala Ala Phe Cys Ala Glu Glu Lys Val Thr Asp Leu Tyr Ala
                885                 890                 895

Arg Glu Leu Val Glu Pro Ala Lys Arg Ser Phe Ser Arg Gly Gln Ile
            900                 905                 910

Ala Gly Ile Phe Tyr Gly Val Ser Gln Phe Phe Ile Phe Ser Ser Tyr
            915                 920                 925

Gly Leu Ala Leu Trp Tyr Gly Ser Val Leu Met Gly Lys Glu Leu Thr
    930                 935                 940

Ser Phe Lys Ala Val Met Lys Ser Phe Met Val Leu Ile Val Thr Ala
945                 950                 955                 960

Leu Ala Met Gly Glu Thr Leu Ala Met Ala Pro Asp Leu Ile Lys Gly
                965                 970                 975

Asn Gln Met Val Ala Ser Val Phe Glu Val Leu Asp Arg Arg Thr Glu
            980                 985                 990

Ile Leu Ala Asp Thr Gly Glu Glu  Val Thr Glu Val Glu  Gly Thr Ile
            995                 1000                1005

Glu Phe  Lys Asp Val Glu Phe  Cys Tyr Pro Ala Arg  Pro Asp Val
```

```
            1010                1015                1020

His Ile Phe Lys Asp Phe Asn Met Arg Val His Ala Gly Glu Ser
        1025                1030                1035

Met Ala Ile Val Gly Gln Ser Gly Ser Gly Lys Ser Ser Val Leu
    1040                1045                1050

Ala Leu Ile Leu Arg Phe Tyr Asp Pro Ile Ser Gly Lys Val Ile
    1055                1060                1065

Ile Asp Gly Lys Asp Ile Arg Lys Leu Lys Leu Lys Ser Leu Arg
    1070                1075                1080

Lys His Ile Gly Leu Val Gln Gln Glu Pro Ala Leu Phe Ala Thr
    1085                1090                1095

Ser Ile Tyr Glu Asn Ile Leu Tyr Gly Lys Glu Gly Ala Ser Glu
    1100                1105                1110

Ala Glu Val Ile Asp Ala Ala Lys Leu Ala Asn Ala His Asn Phe
    1115                1120                1125

Ile Ser Ala Leu Pro Asp Gly Tyr Ser Thr Gln Val Gly Glu Arg
    1130                1135                1140

Gly Val Gln Leu Ser Gly Gly Gln Lys Gln Arg Val Ala Ile Ala
    1145                1150                1155

Arg Ala Val Leu Lys Asn Pro Glu Ile Leu Leu Leu Asp Glu Ala
    1160                1165                1170

Thr Ser Ala Leu Asp Val Glu Ser Glu Arg Ile Val Gln Gln Ala
    1175                1180                1185

Leu Asp Arg Leu Met Gln Asn Arg Thr Thr Val Ile Val Ala His
    1190                1195                1200

Arg Leu Ser Thr Ile Arg Asn Ala Asp Gln Ile Ser Val Leu Gln
    1205                1210                1215

Asp Gly Lys Ile Met Glu Gln Gly Thr His Ser Ala Leu Val Glu
    1220                1225                1230

Asn Asn Asp Gly Ala Tyr His Lys Leu Ile Asn Leu Gln Gln Gln
    1235                1240                1245

Gln Gln Gln
    1250

<210> SEQ ID NO 11
<211> LENGTH: 1251
<212> TYPE: PRT
<213> ORGANISM: Capsicum annuum

<400> SEQUENCE: 11

Met Ser His Gln Gln Ser His Ala Leu Ser Val Asp Ser Ser Gly Ile
1               5                   10                  15

Ser Lys Met Lys Gln Lys Asn Thr Gly Asp Glu Glu Arg Lys Lys Pro
            20                  25                  30

Lys Lys Val Ser Leu Leu Lys Leu Phe Ser Phe Ala Asp Ser Tyr Asp
        35                  40                  45

Tyr Leu Leu Met Phe Leu Gly Ser Ile Gly Ala Cys Leu His Gly Ala
    50                  55                  60

Ser Val Pro Val Phe Phe Ile Phe Phe Gly Lys Leu Ile Asn Ile Ala
65                  70                  75                  80

Gly Leu Ala Tyr Leu Phe Pro Ala Leu Ala Ser His Lys Val Ala Lys
                85                  90                  95

Tyr Ser Leu Asp Phe Val Tyr Leu Ser Val Val Ile Leu Phe Ala Ser
            100                 105                 110
```

```
Trp Ile Glu Val Ala Cys Trp Met His Ser Gly Glu Arg Gln Ala Ala
            115                 120                 125

Lys Ile Arg Met Ala Tyr Leu Lys Ser Met Leu Asn Gln Asp Ile Ser
        130                 135                 140

Leu Phe Asp Thr Glu Ala Ser Thr Gly Glu Val Ile Ser Ala Ile Thr
145                 150                 155                 160

Ser Asp Ile Ile Val Val Gln Asp Ala Ile Ser Glu Lys Ala Gly Asn
                165                 170                 175

Phe Met His Tyr Ile Ser Arg Phe Leu Ala Gly Phe Thr Ile Gly Phe
            180                 185                 190

Ile Arg Val Trp Gln Ile Ser Leu Val Thr Leu Ser Ile Val Pro Leu
        195                 200                 205

Ile Ala Leu Ala Gly Gly Ile Tyr Ala Phe Val Thr Ile Gly Leu Ile
210                 215                 220

Ala Arg Val Arg Lys Ser Tyr Ile Asn Ala Gly Glu Val Ala Glu Glu
225                 230                 235                 240

Val Ile Ala Asn Ile Arg Thr Val Gln Ala Phe Ala Gly Glu Glu Lys
                245                 250                 255

Ala Val Lys Ala Tyr Lys Gly Ala Leu Leu Asn Thr Tyr Gln Tyr Gly
            260                 265                 270

Lys Lys Ala Gly Leu Ala Lys Gly Leu Gly Leu Gly Thr Leu His Cys
        275                 280                 285

Val Leu Phe Leu Ser Trp Ser Leu Leu Val Trp Phe Thr Ser Ile Val
        290                 295                 300

Val His Lys Asn Ile Ala Asn Gly Gly Glu Ser Phe Thr Thr Met Leu
305                 310                 315                 320

Asn Val Val Ile Ala Gly Leu Ser Leu Gly Gln Ala Ala Pro Asp Ile
                325                 330                 335

Thr Ala Phe Leu Arg Ala Lys Ser Ala Ala Tyr Pro Ile Phe Glu Met
            340                 345                 350

Ile Glu Arg Asp Thr Ile Ser Lys Ile Ser Ser Lys Ser Gly His Gln
        355                 360                 365

Leu Ser Glu Val Asp Gly His Ile Gln Phe Lys Asp Val Cys Phe Ser
370                 375                 380

Tyr Pro Ser Arg Pro Asp Val Val Ile Phe Asp Lys Phe Ser Leu Asp
385                 390                 395                 400

Ile Pro Ser Gly Lys Ile Val Ala Leu Val Gly Ser Gly Ser Gly
                405                 410                 415

Lys Ser Thr Val Ile Ser Leu Ile Glu Arg Phe Tyr Glu Pro Leu Ser
            420                 425                 430

Gly His Ile Leu Leu Asp Gly Ser Asp Ile Arg His Leu Asp Leu Lys
        435                 440                 445

Trp Leu Arg Gln Gln Ile Gly Leu Val Asn Gln Pro Ala Leu Phe
        450                 455                 460

Ala Thr Thr Ile Arg Glu Asn Ile Leu Tyr Gly Lys Ser Asp Ala Ser
465                 470                 475                 480

Leu Glu Asp Ile Ala Arg Ala Ala Lys Leu Ser Glu Ala Met Thr Phe
                485                 490                 495

Ile Asn Asn Leu Pro Asp Arg Leu Glu Thr Gln Val Gly Glu Arg Gly
            500                 505                 510

Val Gln Leu Ser Gly Gly Gln Lys Gln Arg Ile Ala Ile Ser Arg Ala
        515                 520                 525

Ile Val Lys Asn Pro Ser Ile Leu Leu Leu Asp Glu Ala Thr Ser Ala
```

```
              530                 535                 540
Leu Asp Ala Glu Ser Glu Lys Ser Val Gln Asp Ala Leu Asp Arg Val
545                 550                 555                 560

Met Val Gly Arg Thr Thr Val Ile Val Ala His Arg Leu Ser Thr Ile
                565                 570                 575

Arg Asn Val Asp Ile Ile Ala Val Val Asn Asn Gly Lys Ile Val Glu
                580                 585                 590

Thr Arg Ser His Glu Glu Leu Ile Ser Lys Pro Asn Gly Ala Tyr Ala
            595                 600                 605

Ser Leu Val Gln Leu Gln Gln Ala Ala Ser Ser His Leu Gln Glu Pro
            610                 615                 620

Thr Met Gly Arg Pro Leu Ser Ile Arg Tyr Ser Arg Glu Leu Ser Arg
625                 630                 635                 640

Thr Arg Thr Gln Ser His Gly Ala Ser Phe Arg Ser Glu Lys Ser Val
                645                 650                 655

Ser Gly Ile Gly Asp Ala Gly Val Glu Asp Val Lys Glu Pro Asn Ile
                660                 665                 670

Ser Leu Arg Arg Leu Tyr Ser Met Ile Arg Pro Glu Trp His Tyr Gly
            675                 680                 685

Val Ile Gly Thr Ile Ser Ala Phe Ile Ala Gly Ser Gln Met Pro Leu
            690                 695                 700

Phe Ala Leu Gly Val Ser Gln Ala Leu Val Ser Tyr Tyr Met Asp Trp
705                 710                 715                 720

Asp Thr Thr Arg His Glu Val Lys Lys Ile Ser Ile Leu Phe Cys Ile
                725                 730                 735

Gly Ala Val Leu Ser Val Ile Val Tyr Ala Ile Ala His Thr Cys Phe
                740                 745                 750

Gly Ile Ile Gly Ala Arg Leu Thr Leu Arg Val Arg Glu Met Met Phe
            755                 760                 765

Ser Ala Met Leu Arg Asn Glu Ile Gly Trp Phe Asp Glu Met Asn Asn
            770                 775                 780

Ser Ser Ser Ser Leu Ala Ser Arg Leu Glu Ser Asp Ala Thr Leu Leu
785                 790                 795                 800

Arg Thr Val Val Val Asp Arg Ser Thr Ile Leu Leu Gln Asn Val Gly
                805                 810                 815

Leu Val Phe Thr Ser Phe Val Ile Ala Phe Met Leu Asn Trp Arg Leu
                820                 825                 830

Thr Leu Ile Val Met Ala Met Tyr Pro Leu Ile Ile Ser Gly His Ile
            835                 840                 845

Ser Glu Lys Leu Phe Met Ala Gly Phe Gly Gly Asp Leu Ser Lys Ala
850                 855                 860

Tyr Leu Arg Ala Asn Met Phe Ala Gly Glu Ala Val Ser Asn Ile Arg
865                 870                 875                 880

Thr Val Ala Ala Phe Cys Ala Glu Glu Lys Val Thr Asp Leu Tyr Ala
                885                 890                 895

Arg Glu Leu Val Glu Pro Ala Lys Arg Ser Phe Ser Arg Gly Gln Ile
                900                 905                 910

Ala Gly Ile Phe Tyr Gly Val Ser Gln Phe Phe Ile Phe Ser Ser Tyr
            915                 920                 925

Gly Leu Ala Leu Trp Tyr Gly Ser Val Leu Met Gly Lys Glu Leu Thr
            930                 935                 940

Ser Phe Lys Ala Val Met Lys Ser Phe Met Val Leu Ile Val Thr Ala
945                 950                 955                 960
```

```
Leu Ala Met Gly Glu Thr Leu Ala Met Ala Pro Asp Leu Ile Lys Gly
            965                 970                 975

Asn Gln Met Val Ala Ser Val Phe Glu Val Leu Asp Arg Arg Thr Glu
            980                 985                 990

Ile Leu Ala Asp Thr Gly Glu Glu  Val Thr Glu Val Glu  Gly Thr Ile
            995                 1000                1005

Glu Phe  Lys Asp Val Glu  Phe  Cys Tyr Pro Ala Arg  Pro Asp Val
            1010                1015                1020

His Ile  Phe Lys Asp Phe  Asn  Met Arg Val His Ala  Gly Glu Ser
            1025                1030                1035

Met Ala  Ile Val Gly Gln Ser  Gly Ser Gly Lys Ser  Ser Val Leu
            1040                1045                1050

Ala Leu  Ile Leu Arg Phe Tyr  Asp Pro Ile Ser Gly  Lys Val Ile
            1055                1060                1065

Ile Asp  Gly Lys Asp Ile Arg  Lys Leu Lys Leu Lys  Ser Leu Arg
            1070                1075                1080

Lys His  Ile Gly Leu Val Gln  Gln Glu Pro Ala Leu  Phe Ala Thr
            1085                1090                1095

Ser Ile  Tyr Glu Asn Ile Leu  Tyr Gly Lys Glu Gly  Ala Ser Glu
            1100                1105                1110

Ala Glu  Val Ile Asp Ala Ala  Lys Leu Ala Asn Ala  His Asn Phe
            1115                1120                1125

Ile Ser  Ala Leu Pro Asp Gly  Tyr Ser Thr Gln Val  Gly Glu Arg
            1130                1135                1140

Gly Val  Gln Leu Ser Gly Gly  Gln Lys Gln Arg Val  Ala Ile Ala
            1145                1150                1155

Arg Ala  Val Leu Lys Asn Pro  Glu Ile Leu Leu Leu  Asp Glu Ala
            1160                1165                1170

Thr Ser  Ala Leu Asp Val Glu  Ser Glu Arg Ile Val  Gln Gln Ala
            1175                1180                1185

Leu Asp  Arg Leu Met Gln Asn  Arg Thr Thr Val Ile  Val Ala His
            1190                1195                1200

Arg Leu  Ser Thr Ile Arg Asn  Ala Asp Gln Ile Ser  Val Leu Gln
            1205                1210                1215

Asp Gly  Lys Ile Met Glu Gln  Gly Thr His Ser Ala  Leu Val Glu
            1220                1225                1230

Asn Asn  Asp Gly Ala Tyr His  Lys Leu Ile Asn Leu  Gln Gln Gln
            1235                1240                1245

Gln Gln  Gln
            1250

<210> SEQ ID NO 12
<211> LENGTH: 22
<212> TYPE: PRT
<213> ORGANISM: Citrullus lanatus

<400> SEQUENCE: 12

Lys Val Gly Asn Phe Leu His Tyr Ile Ser Arg Phe Ile Ser Gly Phe
1               5                   10                  15

Ile Ile Gly Phe Val Arg
            20

<210> SEQ ID NO 13
<211> LENGTH: 22
<212> TYPE: PRT
```

```
<213> ORGANISM: Solanum lycopersicum

<400> SEQUENCE: 13

Lys Ala Gly Asn Phe Leu His Tyr Ile Ser Arg Phe Leu Ala Gly Phe
1               5                   10                  15

Thr Ile Gly Phe Ile Arg
            20

<210> SEQ ID NO 14
<211> LENGTH: 46
<212> TYPE: DNA
<213> ORGANISM: artificial
<220> FEATURE:
<223> OTHER INFORMATION: Primer FAM(dye)

<400> SEQUENCE: 14
gaaggtgacc aagttcatgc tccctcacaa atccgataat aaaccc              46

<210> SEQ ID NO 15
<211> LENGTH: 47
<212> TYPE: DNA
<213> ORGANISM: artificial
<220> FEATURE:
<223> OTHER INFORMATION: Primer VIC(dye)

<400> SEQUENCE: 15
gaaggtcgga gtcaacggat taccctcaca aatccgataa taaacct             47

<210> SEQ ID NO 16
<211> LENGTH: 29
<212> TYPE: DNA
<213> ORGANISM: artificial
<220> FEATURE:
<223> OTHER INFORMATION: Primer common

<400> SEQUENCE: 16
gggaactttt tgcattatat aagccggtt                                 29
```